(12) United States Patent
Biemans et al.

(10) Patent No.: US 9,676,732 B2
(45) Date of Patent: Jun. 13, 2017

(54) ETHYNYL DERIVATIVES

(71) Applicant: Hoffmann-La Roche Inc., Little Falls, NJ (US)

(72) Inventors: Barbara Biemans, Basel (CH); Wolfgang Guba, Muellheim (DE); Georg Jaeschke, Basel (CH); Antonio Ricci, Birsfelden (CH); Daniel Rueher, Raedersdorf (FR); Eric Vieira, Frenkendorf (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/283,010

(22) Filed: Sep. 30, 2016

(65) Prior Publication Data
US 2017/0114028 A1  Apr. 27, 2017

Related U.S. Application Data

(63) Continuation of application No. 15/081,573, filed on Mar. 25, 2016, which is a continuation of application No. PCT/EP2014/070100, filed on Sep. 22, 2014.

(30) Foreign Application Priority Data

Sep. 25, 2013 (EP) .................... 13185856

(51) Int. Cl.
| | | |
|---|---|---|
| C07D 239/96 | (2006.01) | |
| C07D 487/06 | (2006.01) | |
| C07D 475/04 | (2006.01) | |
| C07D 473/04 | (2006.01) | |
| C07D 401/04 | (2006.01) | |
| C07D 513/04 | (2006.01) | |
| C07D 495/04 | (2006.01) | |
| C07D 239/91 | (2006.01) | |
| C07D 471/04 | (2006.01) | |
| C07D 487/04 | (2006.01) | |
| C07D 405/04 | (2006.01) | |
| C07D 401/10 | (2006.01) | |
| C07D 405/14 | (2006.01) | |
| C07D 475/02 | (2006.01) | |

(52) U.S. Cl.
CPC ......... *C07D 239/96* (2013.01); *C07D 401/04* (2013.01); *C07D 401/10* (2013.01); *C07D 405/04* (2013.01); *C07D 405/14* (2013.01); *C07D 473/04* (2013.01); *C07D 475/02* (2013.01); *C07D 487/04* (2013.01); *C07D 487/06* (2013.01); *C07D 495/04* (2013.01); *C07D 513/04* (2013.01)

(58) Field of Classification Search
None
See application file for complete search history.

(56) References Cited

U.S. PATENT DOCUMENTS 5,935,907 A * 8/1999 Yanagi .............. A01N 43/54
504/239

* cited by examiner

Primary Examiner — Brian J Davis
(74) Attorney, Agent, or Firm — Tamara A. Kale

(57) ABSTRACT

It has been surprisingly been found that the compounds of general formula I are positive allosteric modulators (PAMs) of metabotropic glutamate receptor 4 (mGluR4), useful for the treatment of Parkinson's disease, anxiety, emesis, obsessive compulsive disorder, autism, neuroprotection, cancer, depression and diabetes type 2.

12 Claims, 1 Drawing Sheet

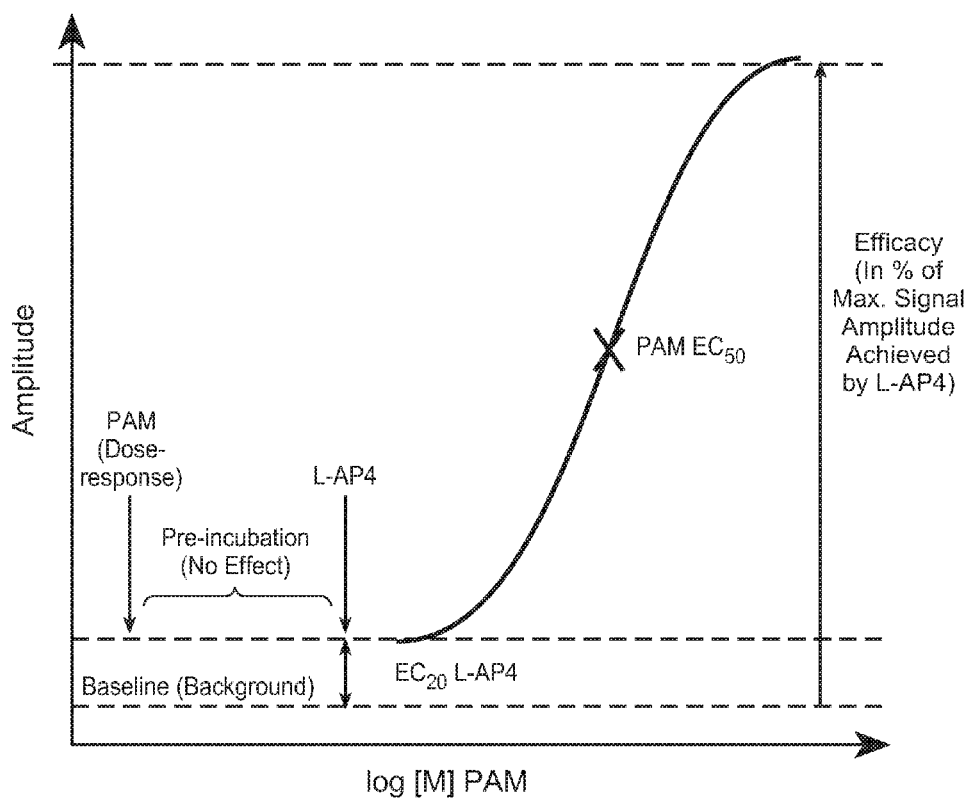

ETHYNYL DERIVATIVES

This application is a continuation of U.S. patent application Ser. No. 15/081,573, filed on Mar. 25, 2016, which is a continuation of International Application No. PCT/EP2014/070100, filed Sep. 22, 2014, which claims priority to European Application No. 13185856.5, filed Sep. 25, 2013, each of which is incorporated herein by reference in its entirety.

The present invention relates to compounds of formula I

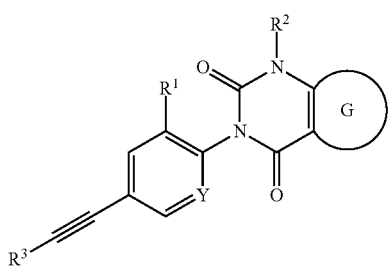

wherein
Y is N or C—R$^{1'}$;
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';
R and R' are independently from each other hydrogen or lower alkyl, or may form together with the N atom to which they are attached a five or six membered saturated heterocyclic group which may contain an additional oxygen, NH, or N-lower alkyl group;
R$^1$ is hydrogen, halogen or lower alkyl substituted by halogen;
R$^{1'}$ is hydrogen, halogen or lower alkyl substituted by halogen;
R$^2$ is hydrogen, lower alkyl, lower alkoxyalkyl, cycloalkyl or heterocycloalkyl;
or R$^2$ may form together with the closest carbon atom in group G a group

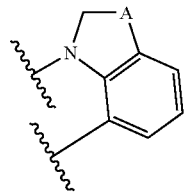

for A being —CH$_2$—, —CH$_2$CH$_2$—, or —C(CH$_3$)$_2$—,
R$^3$ is phenyl or pyridinyl, wherein the N atom in the pyridinyl group may be in different positions;
or to a pharmaceutically acceptable salt or acid addition salt, to a racemic mixture, or to its corresponding enantiomer and/or optical isomer and/or stereoisomer thereof.

It has been surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene.

Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (Celanire S, Campo B, *Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAM is emerging as a promising target for the treatment of motor (and non motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whist attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). Those studies provide preclinical evidence suggesting that mGluR4 activators constitute a strong approach not only for symptomatic treatments of PD, but also potentially as disease modifiers.

The neuroprotective effect of selective mGluR4 was also described in *Neuroreport*, 19(4), 475-8, 2008, *Proc. Natl.*

Acad. Sci, USA, 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (Prediger R, et al. *Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.*, 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology*, 46(2), 151-9, 2004).

In addition, mGluR4 were also shown to be involved in glucagon secretion inhibition (*Diabetes*, 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research*, 11(9)3288-95, 2005). mGluR4 modulators may therefore have also potential role for the treatment of cancers.

Other proposed effects of MgluR4 PAM's can be expected for the treatment of emesis, obsessive compulsive disorder and autism.

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, autism, neuroprotection, cancer, depression and diabetes type 2.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR4 receptor, such as Parkinson's disease, anxiety, emesis, obsessive compulsive disorder, autism, neuroprotection, cancer, depression and diabetes type 2 and to pharmaceutical compositions containing the compounds of formula I.

A further object of the present invention is a method for the treatment or prophylaxis of Parkinson's disease, anxiety, emesis, obsessive compulsive disorder, autism, neuroprotection, cancer, depression and diabetes type 2, which method comprises administering an effective amount of a compound of formula I to a mammal in need.

Furthermore, the invention includes all racemic mixtures, all their corresponding enantiomers and/or optical isomers.

BRIEF DESCRIPTION OF THE FIGURE

FIG. 1 is an illustration of the experimental outline for the mGlu4 PAM Ca2+ mobilization screening assay and the determination of $EC_{50}$ and % Emax values.

The following definitions of the general terms used in the present description apply irrespective of whether the terms in question appear alone or in combination.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked with an O atom.

The term "cycloalkyl" denotes a saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl.

The term heterocycloalkyl" denoted a cycloalkyl ring as defined above, wherein at least one carbon atom is replaced by O, N, or S, for example tetrahydrofuranyl, morpholinyl piperidinyl or oxetanyl.

The term "halogen" denotes chlorine, iodine, fluorine and bromine.

The term "lower alkyl substituted by halogen" denotes a lower alkyl group as defined above, wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$. The preferred "lower alkyl substituted by halogen" group is $CF_3$.

The term "lower alkoxy substituted by halogen" denotes an alkoxy group as defined above, wherein at least one hydrogen atom is replaced by halogen. A preferred group is $OCH_2CHF_2$.

The term "five or six membered saturated heterocyclic group which may contain an additional oxygen, NH or N-lower alkyl group denotes a piperidine group, a piperazine group or a morpholine group.

The term "lower alkoxyalkyl" denotes an alkyl group as defined above and which is linked with an alkoxy group.

The group

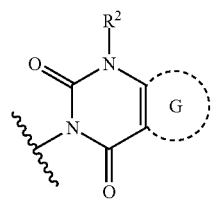

means

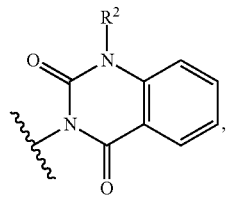 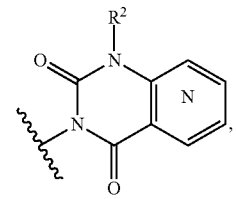

-continued

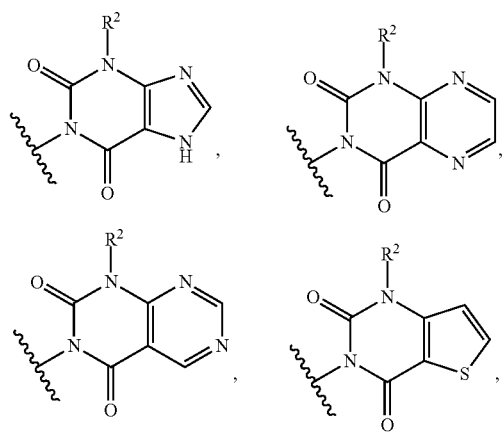

or

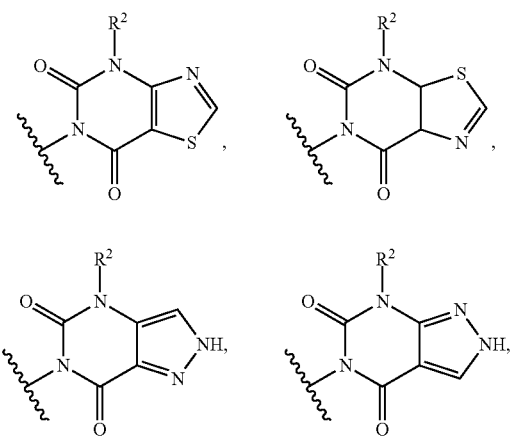

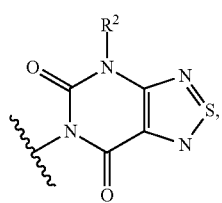

is a pyridine group, wherein the N atom may be in different positions, or means the group

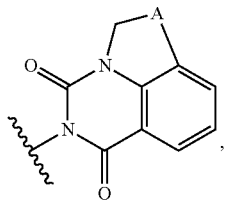

wherein A is as defined above.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention is compounds of formula IA

IA

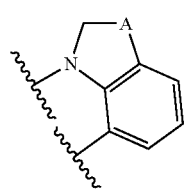

wherein
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';
R and R' are independently from each other hydrogen or lower alkyl, or may form together with the N atom to which they are attached a five or six membered saturated heterocyclic group which may contain an additional oxygen, NH, or N-lower alkyl group;
$R^1$ is hydrogen, halogen or lower alkyl substituted by halogen;
$R^{1'}$ is hydrogen, halogen or lower alkyl substituted by halogen;
$R^2$ is hydrogen, lower alkyl, lower alkoxyalkyl, cycloalkyl or heterocycloalkyl;
or $R^2$ may form together with the closest carbon atom in group G a group wherein these groups may be substituted as described for "G" above, $R^2$ is defined above and for A being —CH$_2$—, —CH$_2$CH$_2$—, or —C(CH$_3$)$_2$—,
or a pharmaceutically acceptable salt or acid addition salt, a racemic mixture, or its corresponding enantiomer and/or optical isomer and/or stereoisomer thereof,
for example the following compounds 3-[2-Chloro-4-(2-phenylethynyl)phenyl]-1-methyl-quinazoline-2,4-dione
3-[2-Chloro-4-(2-phenylethynyl)phenyl]-1,8-dimethyl-quinazoline-2,4-dione
8-Chloro-3-[2-chloro-4-(2-phenylethynyl)phenyl]-1-methyl-quinazoline-2,4-dione
7-Chloro-3-[2-chloro-4-(2-phenylethynyl)phenyl]-1-methyl-quinazoline-2,4-dione
3-[2-Chloro-4-(2-phenylethynyl)phenyl]-1,7-dimethyl-quinazoline-2,4-dione
3-[2-Chloro-4-(2-phenylethynyl)phenyl]-1H-pyrido[2, 3-d]pyrimidine-2,4-dione
3-[2-Chloro-4-(2-phenylethynyl)phenyl]-1-methyl-pyrido[2,3-d]pyrimidine-2,4-dione
3-[2-Chloro-4-(2-phenylethynyl)phenyl]-8-ethyl-1-methyl-quinazoline-2,4-dione
3-[2-Chloro-4-(2-phenylethynyl)phenyl]-1-methyl-pyrido[3,2-d]pyrimidine-2,4-dione
3-[2-Chloro-4-(2-phenylethynyl)phenyl]-1-methyl-pyrido[4,3-d]pyrimidine-2,4-dione
1-[2-Chloro-4-(2-phenylethynyl)phenyl]-3,7-dimethyl-purine-2,6-dione
2-(2-Chloro-4-(phenylethynyl)phenyl)-5,6-dihydro-1H-pyrrolo[3,2,1-ij]quinazoline-1,3(2H)-dione
3-[2-Chloro-4-(2-phenylethynyl)phenyl]-1-isopropyl-quinazoline-2,4-dione
3-[2-Chloro-4-(2-phenylethynyl)phenyl]-1-ethyl-quinazoline-2,4-dione
3-[2-Chloro-4-(2-phenylethynyl)phenyl]-1-methyl-pteridine-2,4-dione
3-[2-Chloro-4-(2-phenylethynyl)phenyl]-1H-pyrimido[4,5-d]pyrimidine-2,4-dione
3-[2-Chloro-4-(2-phenylethynyl)phenyl]-1-methyl-pyrimido[4,5-d]pyrimidine-2,4-dione
3-[2-Chloro-4-(2-phenylethynyl)phenyl]-6-fluoro-1-methyl-quinazoline-2,4-dione
3-[2-Chloro-4-(2-phenylethynyl)phenyl]-7, 8-difluoro-1-methyl-quinazoline-2,4-dione
3-[2-Chloro-4-(2-phenylethynyl)phenyl]-1,7-dimethyl-thieno[3,2-d]pyrimidine-2,4-dione
3-[2-Chloro-4-(2-phenylethynyl)phenyl]-1-isopropyl-pteridine-2,4-dione
3-[2,6-Difluoro-4-(2-phenylethynyl)phenyl]-1-methyl-quinazoline-2,4-dione
3-[2,6-Difluoro-4-(2-phenylethynyl)phenyl]-1,8-dimethyl-quinazoline-2,4-dione
3-(2,6-Difluoro-4-phenylethynyl-phenyl)-1-methyl-1H-pyrido[2,3-d]pyrimidine-2,4-dione
3-[2,6-Difluoro-4-(2-phenylethynyl)phenyl]-1,7-dimethyl-quinazoline-2,4-dione
3-[2,6-Difluoro-4-(2-phenylethynyl)phenyl]-1,7-dimethyl-thieno[3,2-d]pyrimidine-2,4-dione
2-(2,6-Difluoro-4-(phenylethynyl)phenyl)-5,6-dihydro-1H-pyrrolo[3,2,1-ij]quinazoline-1,3(2H)-dione
6-[2,6-Difluoro-4-(2-phenylethynyl)phenyl]-4H-thiazolo[4,5-d]pyrimidine-5,7-dione
6-[2,6-Difluoro-4-(2-phenylethynyl)phenyl]-4-methyl-thiazo[4,5-d]pyrimidine-5,7-dione
6-[2,6-Difluoro-4-(2-phenylethynyl)phenyl]-2,4-dimethyl-pyrazolo[4,3-d]pyrimidine-5,7-dione
6-[2,6-Difluoro-4-(2-phenylethynyl)phenyl]-1,4-dimethyl-pyrazolo[4,3-d]pyrimidine-5,7-dione
6-[2,6-Difluoro-4-(2-phenylethynyl)phenyl]-4-isopropyl-2-methyl-pyrazolo[4,3-d]pyrimidine-5,7-dione
6-[2,6-Difluoro-4-(2-phenylethynyl)phenyl]-4-isopropyl-1-methyl-pyrazolo[4,3-d]pyrimidine-5,7-dione
3-[2,6-Difluoro-4-(2-phenylethynyl)phenyl]-1-isopropyl-pyrido[2,3-d]pyrimidine-2,4-dione
3-[2,6-Difluoro-4-(2-phenylethynyl)phenyl]-1,8-dimethyl-pyrido[3,2-d]pyrimidine-2,4-dione
6-[2,6-Difluoro-4-(2-phenylethynyl)phenyl]-4-methyl-[1,2,5]thiadiazolo[3,4-d]pyrimidine-5,7-dione
6-[2,6-Difluoro-4-(2-phenylethynyl)phenyl]-4-isopropyl-[1,2,5]thiadiazolo[3,4-d]pyrimidine-5,7-dione
3-[2-Chloro-4-(2-phenylethynyl)phenyl]-1,5-dimethyl-quinazoline-2,4-dione
3-[2-Chloro-4-(2-phenylethynyl)phenyl]-1-(2-methoxyethyl)quinazoline-2,4-dione
6-[2-Chloro-4-(2-phenylethynyl)phenyl]-4-methyl-2-morpholino-thiazolo[4,5-d]pyrimidine-5,7-dione
6-(2-Chloro-4-phenylethynyl-phenyl)-4-methyl-4H-thiazolo[4, 5-d]pyrimidine-5,7-dione
3-[2-Chloro-4-(2-phenylethynyl)phenyl]-1-cyclobutyl-quinazoline-2,4-dione
3-[2-Chloro-4-(2-phenylethynyl)phenyl]-8-isopropyl-1-methyl-quinazoline-2,4-dione
8-Chloro-3-[2,6-difluoro-4-(2-phenylethynyl)phenyl]-1-methyl-pyrido[3,2-d]pyrimidine-2,4-dione
5-[2,6-Difluoro-4-(2-phenylethynyl)phenyl]-2,7-dimethyl-pyrazolo[3,4-d]pyrimidine-4,6-dione
5-[2,6-Difluoro-4-(2-phenylethynyl)phenyl]-1,7-dimethyl-pyrazolo[3,4-d]pyrimidine-4,6-dione
5-[2,6-Difluoro-4-(2-phenylethynyl)phenyl]-7-isopropyl-2H-pyrazolo[3,4-d]pyrimidine-4,6-dione
3-[2-Chloro-4-(2-phenylethynyl)phenyl]-8-methoxy-1-methyl-quinazoline-2,4-dione
3-[2,6-Difluoro-4-(2-phenylethynyl)phenyl]-1-(oxetan-3-yl)quinazoline-2,4-dione
6-[2-Chloro-4-(2-phenylethynyl)phenyl]-4-methyl-thiazolo[5,4-d]pyrimidine-5,7-dione
3-[2,6-Difluoro-4-(2-phenylethynyl)phenyl]-1-isopropyl-pteridine-2,4-dione
1-[2,6-Difluoro-4-(2-phenylethynyl)phenyl]-3,7-dimethyl-purine-2,6-dione
3-[2,6-Difluoro-4-(2-phenylethynyl)phenyl]-8-methoxy-1-methyl-quinazoline-2,4-dione
3-[2-Fluoro-4-(2-phenylethynyl)-6-(trifluoromethyl)phenyl]-1-isopropyl-quinazoline-2,4-dione or
8-(2,2-Difluoroethoxy)-3-[2,6-difluoro-4-(2-phenylethynyl)phenyl]-1-methyl-quinazoline-2,4-dione.

One embodiment of the invention is further compounds of formula IB,

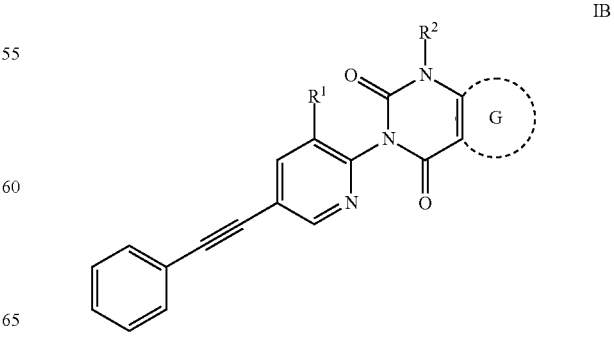

IB wherein

G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

$R^1$ is hydrogen, halogen or lower alkyl substituted by halogen;

$R^2$ is hydrogen, lower alkyl, lower alkoxyalkyl, cycloalkyl or heterocycloalkyl;

or $R^2$ may form together with the closest carbon atom in group G a group

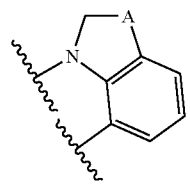

for A being —CH$_2$—, —CH$_2$CH$_2$—, or —C(CH$_3$)$_2$—, or a pharmaceutically acceptable salt or acid addition salt, a racemic mixture, or its corresponding enantiomer and/or optical isomer and/or stereoisomer thereof, for example the following compounds 3-[3-Chloro-5-(2-phenylethynyl)-2-pyridyl]-1-methyl-quinazoline-2,4-dione 3-[3-Chloro-5-(2-phenylethynyl)-2-pyridyl]-1-isopropyl-quinazoline-2,4-dione 3-[3-Chloro-5-(2-phenylethynyl)-2-pyridyl]-1,8-dimethyl-quinazoline-2,4-dione 2-(3-Chloro-5-(phenylethynyl)pyridin-2-yl)-5,6-dihydro-1H-pyrrolo[3,2,1-ij]quinazoline-1,3(2H)-dione 1-Methyl-3-[5-(2-phenylethynyl)-3-(trifluoromethyl)-2-pyridyl]quinazoline-2,4-dione 3-[3-Fluoro-5-(2-phenylethynyl)-2-pyridyl]-1,8-dimethyl-quinazoline-2,4-dione 1-Isopropyl-3-[5-(2-phenylethynyl)-2-pyridyl]quinazoline-2,4-dione 6-[3-Fluoro-5-(2-phenylethynyl)-2-pyridyl]-4-isopropyl-2-methyl-pyrazolo[4,3-d]pyrimidine-5,7-dione or 6-[3-Chloro-5-(2-phenylethynyl)-2-pyridyl]-4-isopropyl-2-methyl-pyrazolo[4,3-d]pyrimidine-5,7-dione.

One embodiment of the invention is compounds of formula IC

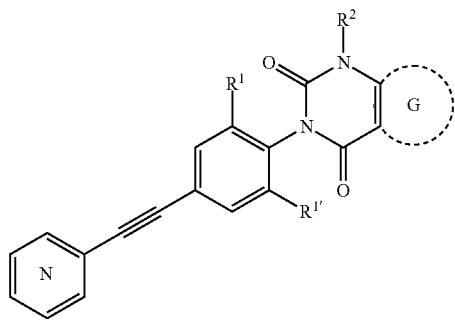

wherein

G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

$R^1$ is hydrogen, halogen or lower alkyl substituted by halogen;

$R^{1'}$ is hydrogen, halogen or lower alkyl substituted by halogen;

$R^2$ is hydrogen, lower alkyl, lower alkoxyalkyl, cycloalkyl or heterocycloalkyl;

or $R^2$ may form together with the closest carbon atom in group G a group

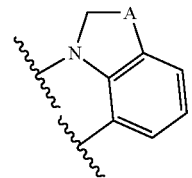

for A being —CH$_2$—, —CH$_2$CH$_2$—, or —C(CH$_3$)$_2$—, or a pharmaceutically acceptable salt or acid addition salt, a racemic mixture, or its corresponding enantiomer and/or optical isomer and/or stereoisomer thereof, for example the following compounds 3-[2-Chloro-4-[2-(3-pyridyl)ethynyl]phenyl]-1-isopropyl-pteridine-2,4-dione 3-[2,6-Difluoro-4-[2-(3-pyridyl)ethynyl]phenyl]-1,7-dimethyl-thieno[3,2-d]pyrimidine-2,4-dione 2-(2,6-Difluoro-4-(pyridin-3-ylethynyl)phenyl)-5,6-dihydro-1H-pyrrolo[3,2,1-ij]quinazoline-1,3(2H)-dione 3-[2-Chloro-6-fluoro-4-[2-(3-pyridyl)ethynyl]phenyl]-1-isopropyl-quinazoline-2,4-dione 3-[2-Chloro-6-fluoro-4-[2-(3-pyridyl)ethynyl]phenyl]-1,8-dimethyl-quinazoline-2,4-dione 6-[2,6-Difluoro-4-[2-(3-pyridyl)ethynyl]phenyl]-4-isopropyl-2-methyl-pyrazolo[4,3-d]pyrimidine-5,7-dione 6-[2-Chloro-6-fluoro-4-[2-(3-pyridyl)ethynyl]phenyl]-4-isopropyl-2-methyl-pyrazolo[4,3-d]pyrimidine-5,7-dione 3-[2-Chloro-6-fluoro-4-[2-(3-pyridyl)ethynyl]phenyl]-1-(oxetan-3-yl)quinazoline-2,4-dione or 3-[2,6-Difluoro-4-[2-(3-pyridyl)ethynyl]phenyl]-1,8-dimethyl-quinazoline-2,4-dione.

One embodiment of the invention is compounds of formula ID,

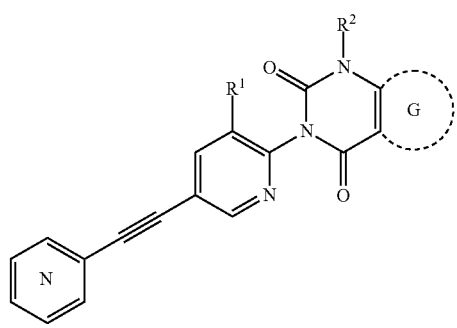

wherein

G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

$R^1$ is hydrogen, halogen or lower alkyl substituted by halogen;

$R^2$ is hydrogen, lower alkyl, lower alkoxyalkyl, cycloalkyl or heterocycloalkyl;

or $R^2$ may form together with the closest carbon atom in group G a group

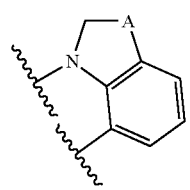

for A being —CH$_2$—, —CH$_2$CH$_2$, or —C(CH$_3$)$_2$—, or a pharmaceutically acceptable salt or acid addition salt, a racemic mixture, or its corresponding enantiomer and/or optical isomer and/or stereoisomer thereof, for example the following compound 6-[3-Chloro-5-[2-(3-pyridyl)ethynyl]-2-pyridyl]-4-isopropyl-2-methyl-pyrazolo[4,3-d]pyrimidine-5,7-dione.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula 2

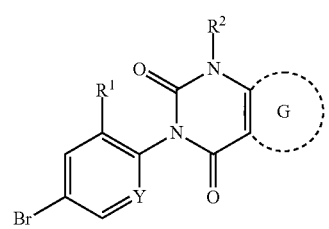

with a compound of formula

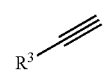

to a compound of formula I

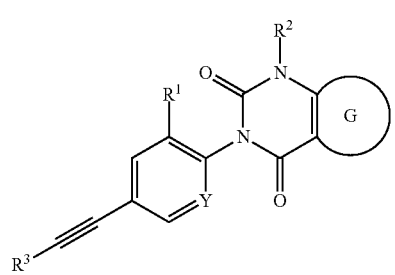

wherein the substituents are described above, or if desired, converting the compounds obtained into pharmaceutically acceptable acid addition salts.

The preparation of compounds of formula I is further described in more detail in scheme 1 and 2 and in examples 1-74.

Scheme 1

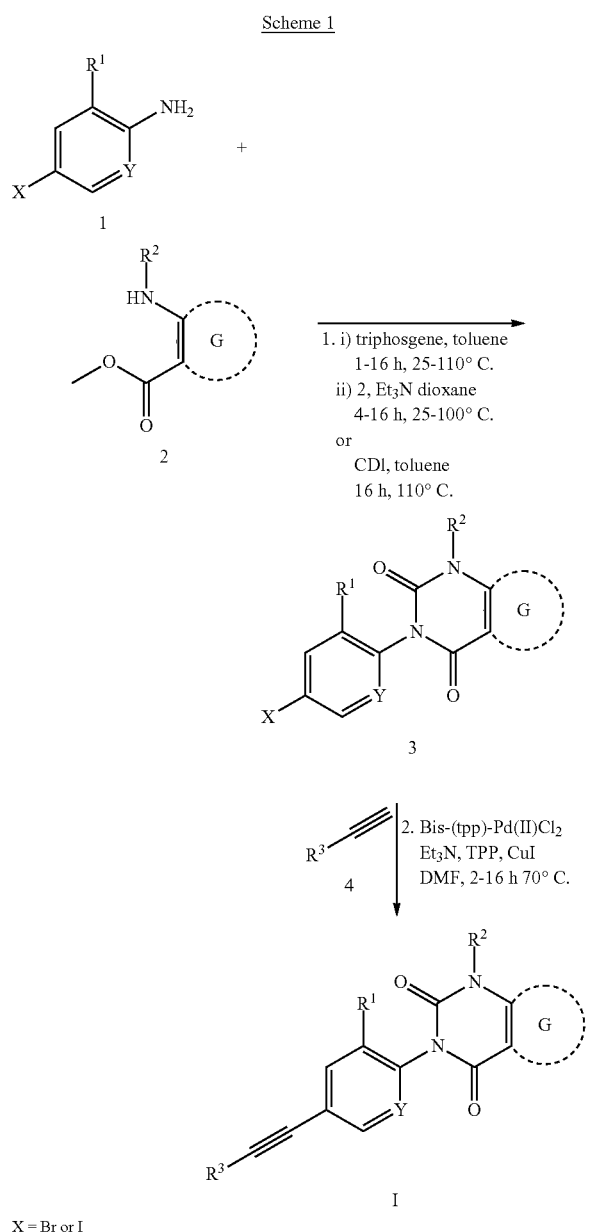

X = Br or I

An ethynyl-phenyl, ethynyl-pyridyl substituted pyrimidinedione compound of formula I can be obtained for example by reacting an appropriately substituted aniline or aminopyridine 1 with an appropriate aromatic or heteroaromatic orthoaminoester 2 with phosgene or a phosgene equivalent such as triphosgene or carbonyldiimidazole (CDI) in presence or absence of a base such as triethylamine in a solvent such as toluene or dioxane to form the corresponding pyrimidine dione of formula 3. Sonogashira coupling of the bromo or iodo-pyrimidinedione 3 with an appropriately substituted arylacetylene 4 yield the desired ethynyl compounds of general formula I (scheme 1). Introduction of the $R^2$ substituent can also be realized at various points in the synthetic sequence via alkylation of the corresponding intermediate where $R^2$=H.

Scheme 2

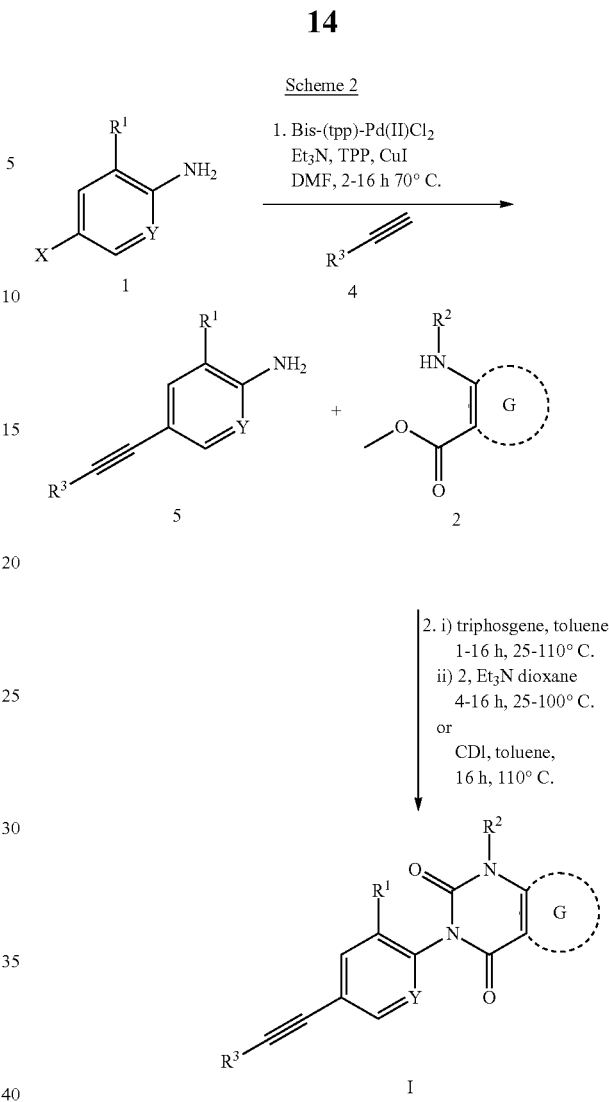

X = Br or I

Generally speaking, the sequence of steps used to synthesize the compounds of formula I can also be modified in certain cases, for example by first running the Sonogashira coupling with an appropriately substituted bromo or iodo aniline or aminopyridine 1 with an appropriately substituted arylacetylene 4 to yield the corresponding ethynyl compounds 5. Reacting 5 with an appropriate aromatic or heteroaromatic orthoaminoester 2 with phosgene or a phosgene equivalent such as triphosgene or carbonyldiimidazole (CDI) in presence or absence of a base such as triethylamine in a solvent such as toluene or dioxane yield the desired ethynyl compounds of general formula I (scheme 2). Introduction of the $R^2$ substituent can also be realized at various points in the synthetic sequence via alkylation of the corresponding intermediate where $R^2$=H.

Biological Assay and Data

Determination of $EC_{50}$ Values Using a Ca2+ Mobilization In Vitro Assay on Recombinant Human mGlu4 Expressed in HEK293 Cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4 was indicative of an inhibitory activity of the test compound.

FIG. 1: Illustration of the experimental outline for mGlu4 PAM Ca2+ mobilization screening assay and the determination of $EC_{50}$ and % Emax values.

List of Examples and data:

| Ex. | Structure | Name | $EC_{50}$ (nM) mGlu4PAM | Eff. (%) |
|---|---|---|---|---|
| 1 | 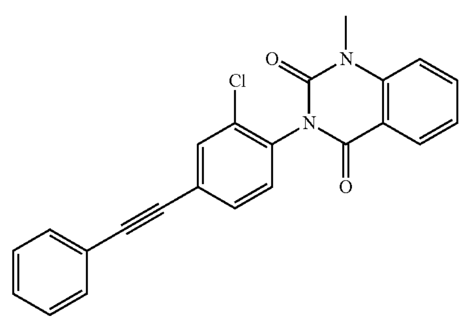 | 3-[2-Chloro-4-(2-phenylethynyl)phenyl]-1-methyl-quinazoline-2,4-dione | 150 | 102 |
| 2 | 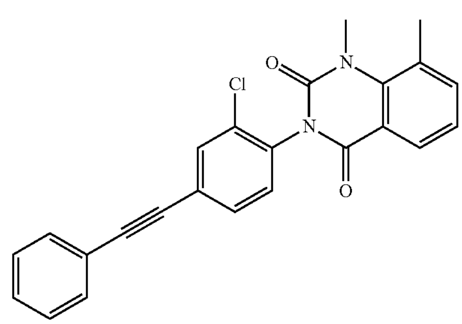 | 3-[2-Chloro-4-(2-phenylethynyl)phenyl]-1,8-dimethyl-quinazoline-2,4-dione | 94 | 99 |

-continued

List of Examples and data:

| Ex. | Structure | Name | EC$_{50}$ (nM) mGlu4PAM | Eff. (%) |
|---|---|---|---|---|
| 3 | 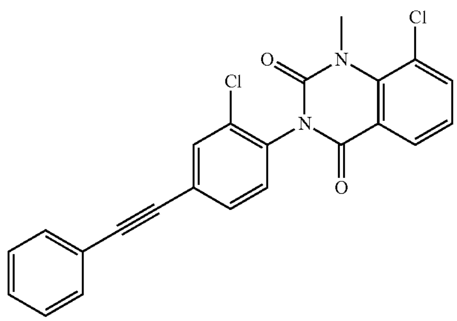 [SMILES: Cn1c(=O)n(-c2ccc(C#Cc3ccccc3)cc2Cl)c(=O)c2cccc(Cl)c21] | 8-Chloro-3-[2-chloro-4-(2-phenylethynyl)phenyl]-1-methyl-quinazoline-2,4-dione | 137 | 93 |
| 4 | 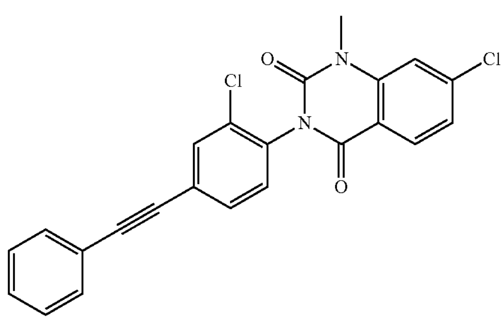 [SMILES: Cn1c(=O)n(-c2ccc(C#Cc3ccccc3)cc2Cl)c(=O)c2ccc(Cl)cc21] | 7-Chloro-3-[2-chloro-4-(2-phenylethynyl)phenyl]-1-methyl-quinazoline-2,4-dione | 220 | 120 |
| 5 | 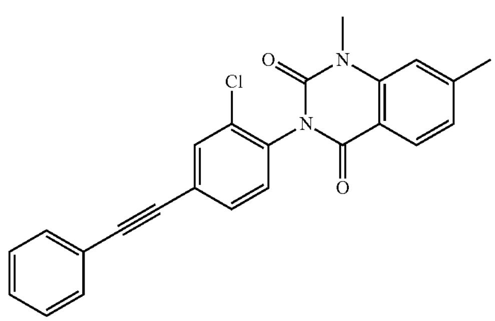 [SMILES: Cc1ccc2c(=O)n(-c3ccc(C#Cc4ccccc4)cc3Cl)c(=O)n(C)c2c1] | 3-[2-Chloro-4-(2-phenylethynyl)phenyl]-1,7-dimethyl-quinazoline-2,4-dione | 93 | 108 |
| 6 | 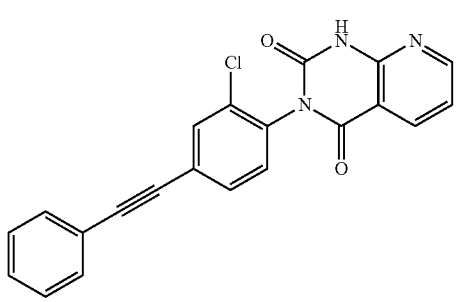 [SMILES: O=c1[nH]c2ncccc2c(=O)n1-c1ccc(C#Cc2ccccc2)cc1Cl] | 3-[2-Chloro-4-(2-phenylethynyl)phenyl]-1H-pyrido[2,3-d]pyrimidine-2,4-dione | 179 | 104 |

-continued

List of Examples and data:

| Ex. | Structure | Name | EC$_{50}$ (nM) mGlu4PAM | Eff. (%) |
|---|---|---|---|---|
| 7 | 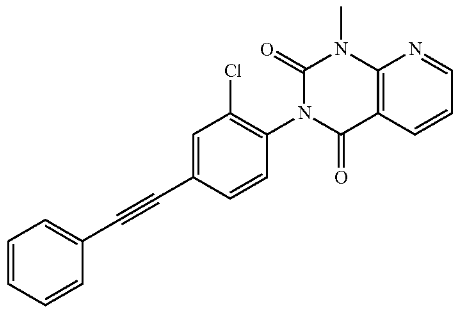 | 3-[2-Chloro-4-(2-phenylethynyl)phenyl]-1-methyl-pyrido[2,3-d]pyrimidine-2,4-dione | 222 | 101 |
| 8 | 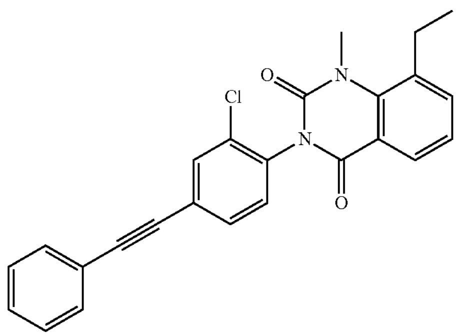 | 3-[2-Chloro-4-(2-phenylethynyl)phenyl]-8 ethyl-1-methyl-quinazoline-2,4-dione | 65 | 100 |
| 9 | 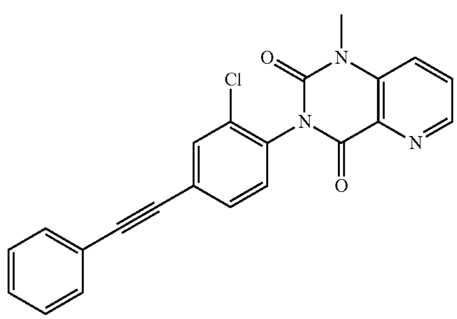 | 3-[2-Chloro-4-(2-phenylethynyl)phenyl]-1-methyl-pyrido[3,2-d]pyrimidine-2,4-dione | 308 | 167 |
| 10 | 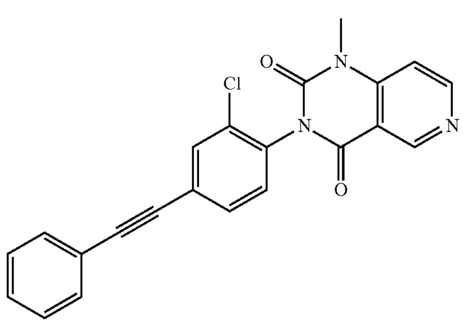 [SMILES: Cn1c(=O)n(-c2ccc(C#Cc3ccccc3)cc2Cl)c(=O)c2cnccc21] | 3-[2-Chloro-4-(2-phenylethynyl)phenyl]-1-methyl-pyrido[4,3-d]pyrimidine-2,4-dione | 399 | 180 |

-continued

List of Examples and data:

| Ex. | Structure | Name | EC$_{50}$ (nM) mGlu4PAM | Eff. (%) |
|---|---|---|---|---|
| 11 | 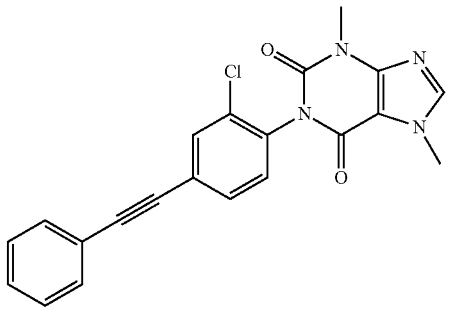 [SMILES: Cn1cnc2c1c(=O)n(-c1ccc(C#Cc3ccccc3)cc1Cl)c(=O)n2C] | 1-[2-Chloro-4-(2-phenylethynyl)phenyl]-3,7-dimethyl-purine-2,6-dione | 175 | 122 |
| 12 | 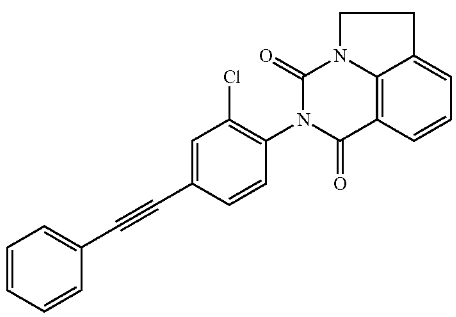 | 2-(2-Chloro-4-(phenylethynyl)phenyl)-5,6-dihydro-1H-pyrrolo[3,2,1-ij]quinazoline-1,3(2H)-dione | 80 | 106 |
| 13 | 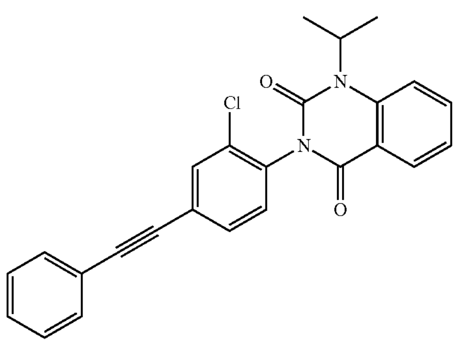 [SMILES: CC(C)n1c(=O)n(-c2ccc(C#Cc3ccccc3)cc2Cl)c(=O)c2ccccc21] | 3-[2-Chloro-4-(2-phenylethynyl)phenyl]-1-isopropyl-quinazoline-2,4-dione | 57 | 115 |
| 14 | 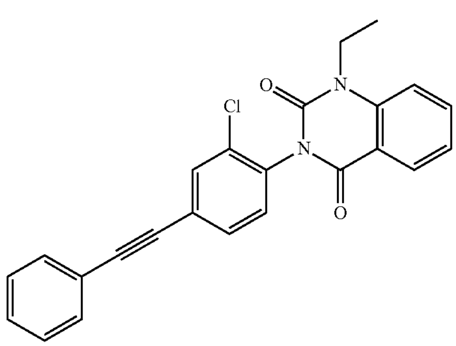 [SMILES: CCn1c(=O)n(-c2ccc(C#Cc3ccccc3)cc2Cl)c(=O)c2ccccc21] | 3-[2-Chloro-4-(2-phenylethynyl)phenyl]-1-ethyl-quinazoline-2,4-dione | 172 | 97 |

-continued

List of Examples and data:

| Ex. | Structure | Name | EC$_{50}$ (nM) mGlu4PAM | Eff. (%) |
|---|---|---|---|---|
| 15 | 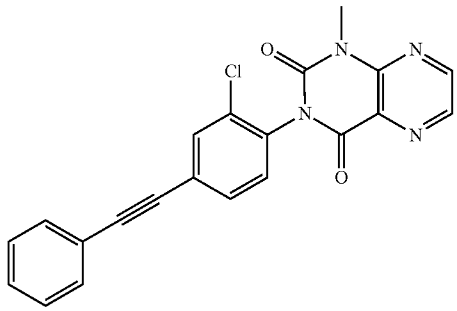 [SMILES: Cn1c(=O)n(-c2ccc(C#Cc3ccccc3)cc2Cl)c(=O)c2nccnc21] | 3-[2-Chloro-4-(2-phenylethynyl)phenyl]-1-methyl-pteridine-2,4-dione | 110 | 111 |
| 16 | 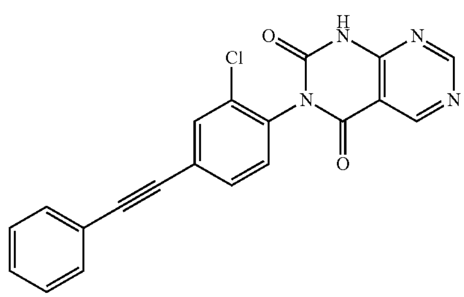 [SMILES: O=c1[nH]c2ncncc2c(=O)n1-c1ccc(C#Cc2ccccc2)cc1Cl] | 3-[2-Chloro-4-(2-phenylethynyl)phenyl]-1H-pyrimido[4,5-d]pyrimidine-2,4-dione | 152 | 98 |
| 17 | 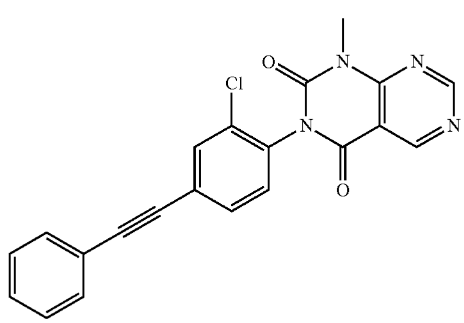 | 3-[2-Chloro-4-(2-phenylethynyl)phenyl]-1-methyl-pyrimido[4,5-d]pyrimidine-2,4-dione | 143 | 101 |
| 18 | 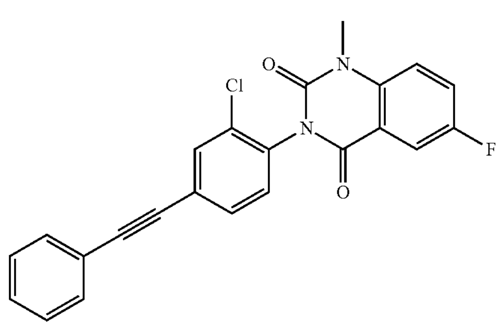 [SMILES: Cn1c(=O)n(-c2ccc(C#Cc3ccccc3)cc2Cl)c(=O)c2cc(F)ccc21] | 3-[2-Chloro-4-(2-phenylethynyl)phenyl]-6-fluoro-1-methyl-quinazoline-2,4-dione | 148 | 86 |

-continued

| Ex. | Structure | Name | EC$_{50}$ (nM) mGlu4PAM | Eff. (%) |
|---|---|---|---|---|
| 19 | 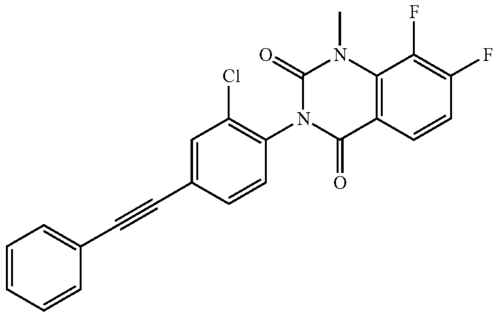 [SMILES: Cn1c(=O)n(-c2ccc(C#Cc3ccccc3)cc2Cl)c(=O)c2ccc(F)c(F)c21] | 3-[2-Chloro-4-(2-phenylethynyl)phenyl]-7,8-difluoro-1-methyl-quinazoline-2,4-dione | 134 | 73 |
| 20 | 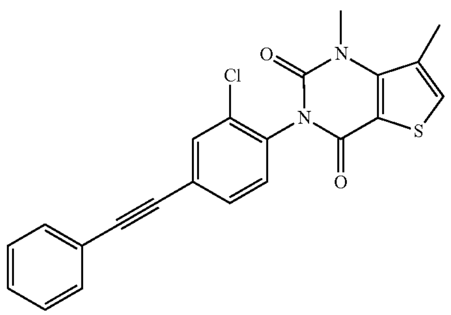 [SMILES: Cc1csc2c(=O)n(-c3ccc(C#Cc4ccccc4)cc3Cl)c(=O)n(C)c12] | 3-[2-Chloro-4-(2-phenylethynyl)phenyl]-1,7-dimethyl-thieno[3,2-d]pyrimidine-2,4-dione | 50 | 74 |
| 21 | 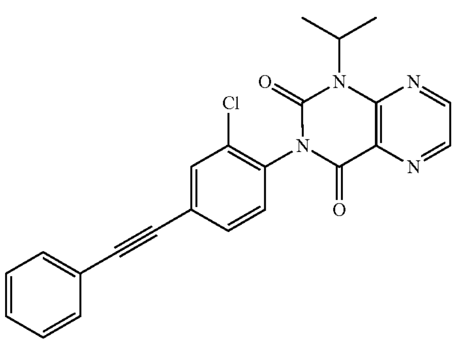 [SMILES: CC(C)n1c(=O)n(-c2ccc(C#Cc3ccccc3)cc2Cl)c(=O)c2nccnc21] | 3-[2-Chloro-4-(2-phenylethynyl)phenyl]-1-isopropyl-pteridine-2,4-dione | 52 | 89 |
| 22 | 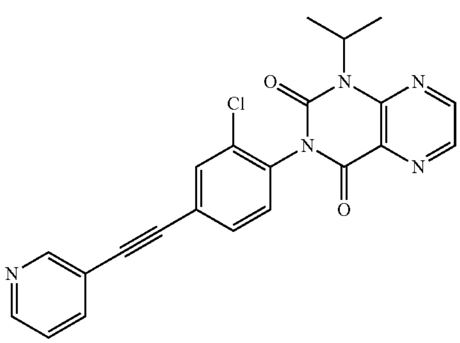 [SMILES: CC(C)n1c(=O)n(-c2ccc(C#Cc3cccnc3)cc2Cl)c(=O)c2nccnc21] | 3-[2-Chloro-4-[2-(3-pyridyl)ethynyl]phenyl]-1-isopropyl-pteridine-2,4-dione | 167 | 88 |

-continued

List of Examples and data:

| Ex. | Structure | Name | EC$_{50}$ (nM) mGlu4PAM | Eff. (%) |
|---|---|---|---|---|
| 23 | 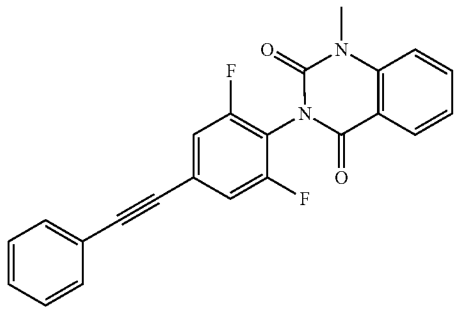 | 3-[2,6-Difluoro-4-(2-phenylethynyl)phenyl]-1-methyl-quinazoline-2,4-dione | 203 | 168 |
| 24 | 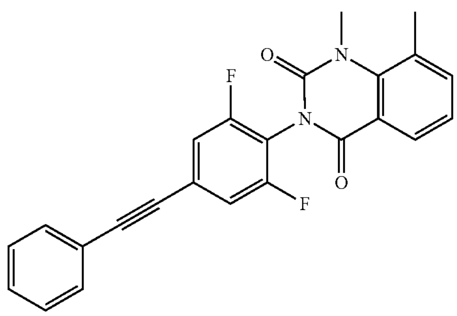 | 3-[2,6-Difluoro-4-(2-phenylethynyl)phenyl]-1,8-dimethyl-quinazoline-2,4-dione | 26 | 101 |
| 25 | 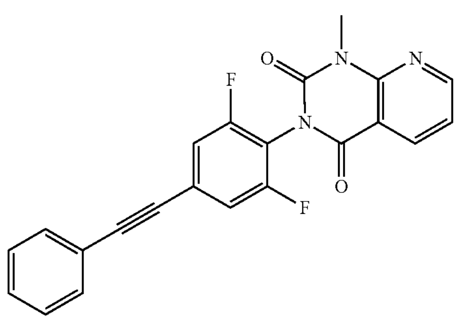 [SMILES: Cn1c(=O)n(-c2c(F)cc(C#Cc3ccccc3)cc2F)c(=O)c2cccnc21] | 3-[2,6-Difluoro-4-(2-phenylethynyl)phenyl]-1-methyl-pyrido[2,3-d]pyrimidine-2,4-dione | 89 | 109 |
| 26 | 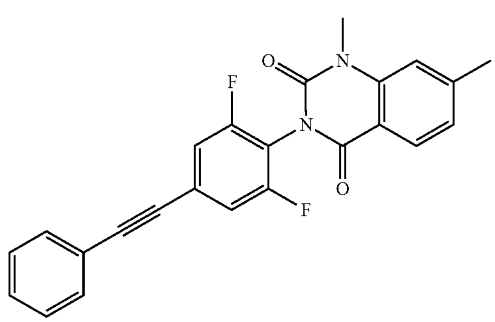 [SMILES: Cc1ccc2c(=O)n(-c3c(F)cc(C#Cc4ccccc4)cc3F)c(=O)n(C)c2c1] | 3-[2,6-Difluoro-4-(2-phenylethynyl)phenyl]-1,7-dimethyl-quinazoline-2,4-dione | 115 | 108 |

| Ex. | Structure | Name | EC$_{50}$ (nM) mGlu4PAM | Eff. (%) |
|---|---|---|---|---|
| 27 | 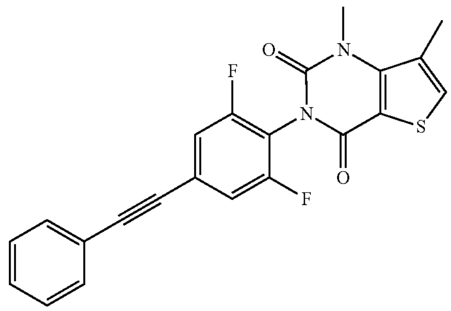 [SMILES: Cc1csc2c(=O)n(-c3c(F)cc(C#Cc4ccccc4)cc3F)c(=O)n(C)c12] | 3-[2,6-Difluoro-4-(2-phenylethynyl)phenyl]-1,7-dimethyl-thieno[3,2-d]pyrimidine-2,4-dione | 16 | 83 |
| 28 | 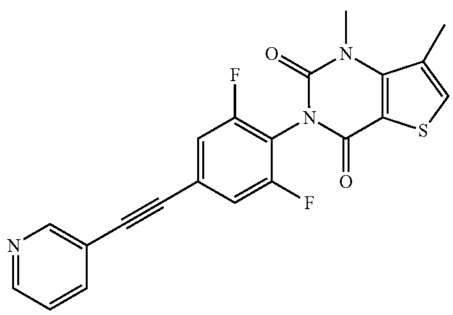 [SMILES: Cc1csc2c(=O)n(-c3c(F)cc(C#Cc4cccnc4)cc3F)c(=O)n(C)c12] | 3-[2,6-Difluoro-4-[2-(3-pyridyl)ethynyl]phenyl]-1,7-dimethyl-thieno[3,2-d]pyrimidine-2,4-dione | 29 | 86 |
| 29 | 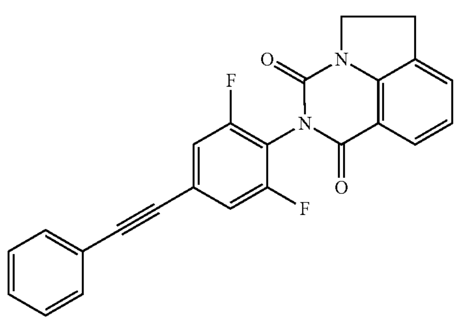 [SMILES: O=c1c2cccc3c2n(c(=O)n1-c1c(F)cc(C#Cc2ccccc2)cc1F)CC3] | 2-(2,6-Difluoro-4-(phenylethynyl)phenyl)-5,6-dihydro-1H-pyrrolo[3,2,1-ij]quinazoline-1,3(2H)-dione | 52 | 78 |
| 30 | 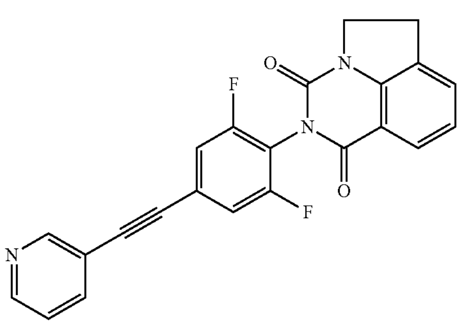 [SMILES: O=c1c2cccc3c2n(c(=O)n1-c1c(F)cc(C#Cc2cccnc2)cc1F)CC3] | 2-(2,6-Difluoro-4-(pyridin-3-ylethynyl)phenyl)-5,6-dihydro-1H-pyrrolo[3,2,1-ij]quinazoline-1,3(2H)-dione | 91 | 89 |

-continued

List of Examples and data:

| Ex. | Structure | Name | EC$_{50}$ (nM) mGlu4PAM | Eff. (%) |
|---|---|---|---|---|
| 31 | 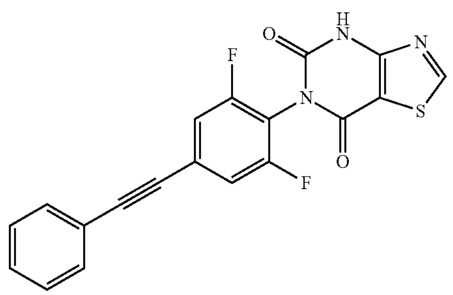 [SMILES: O=c1[nH]c2ncsc2c(=O)n1-c1c(F)cc(C#Cc2ccccc2)cc1F] | 6-[2,6-Difluoro-4-(2-phenylethynyl)phenyl]-4H-thiazolo[4,5-d]pyrimidine-5,7-dione | 187 | 85 |
| 32 | 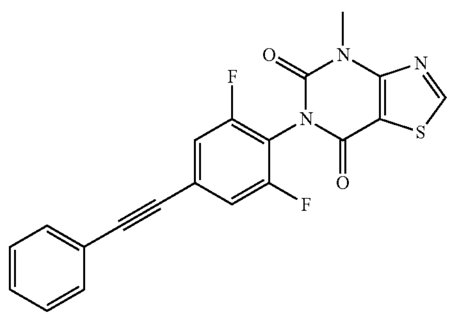 [SMILES: Cn1c(=O)n(-c2c(F)cc(C#Cc3ccccc3)cc2F)c(=O)c2scnc21] | 6-[2,6-Difluoro-4-(2-phenylethynyl)phenyl]-4-methyl-thiazolo[4,5-d]pyrimidine-5,7-dione | 33 | 104 |
| 33 | 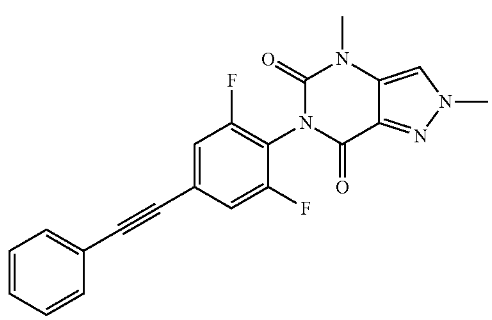 [SMILES: Cn1cc2c(n1)c(=O)n(-c1c(F)cc(C#Cc3ccccc3)cc1F)c(=O)n2C] | 6-[2,6-Difluoro-4-(2-phenylethynyl)phenyl]-2,4-dimethyl-pyrazolo[4,3-d]pyrimidine-5,7-dione | 47 | 86 |
| 34 | 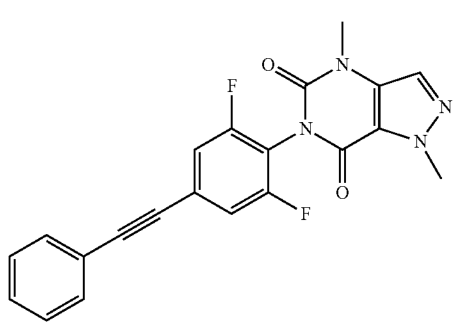 [SMILES: Cn1ncc2c1c(=O)n(-c1c(F)cc(C#Cc3ccccc3)cc1F)c(=O)n2C] | 6-[2,6-Difluoro-4-(2-phenylethynyl)phenyl]-1,4-dimethyl-pyrazolo[4,3-d]pyrimidine-5,7-dione | 74 | 85 |

-continued

| List of Examples and data: | | | | |
|---|---|---|---|---|
| Ex. | Structure | Name | EC$_{50}$ (nM) mGlu4PAM | Eff. (%) |
| 35 | | 6-[2,6-Difluoro-4-(2-phenylethynyl)phenyl]-4-isopropyl-2-methyl-pyrazolo[4,3-d]pyrimidine-5,7-dione | 30 | 89 |
| 36 | | 6-[2,6-Difluoro-4-(2-phenylethynyl)phenyl]-4-isopropyl-1-methyl-pyrazolo[4,3-d]pyrimidine-5,7-dione | 155 | 89 |
| 37 | | 3-[2,6-Difluoro-4-(2-phenylethynyl)phenyl]-1-isopropyl-pyrido[2,3-d]pyrimidine-2,4-dione | 88 | 73 |
| 38 | | 3-[2,6-Difluoro-4-(2-phenylethynyl)phenyl]-1,8-dimethyl-pyrido[3,2-d]pyrimidine-2,4-dione | 108 | 108 |

| Ex. | Structure | Name | EC$_{50}$ (nM) mGlu4PAM | Eff. (%) |
|---|---|---|---|---|
| 39 | 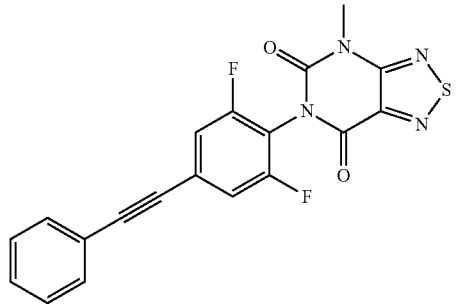 [SMILES: Cn1c(=O)n(-c2c(F)cc(C#Cc3ccccc3)cc2F)c(=O)c2nsnc21] | 6-[2,6-Difluoro-4-(2-phenylethynyl)phenyl]-4-methyl-[1,2,5]thiadiazolo[3,4-d]pyrimidine-5,7-dione | 17 | 107 |
| 40 | 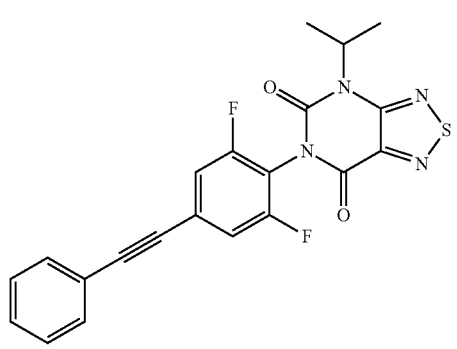 [SMILES: CC(C)n1c(=O)n(-c2c(F)cc(C#Cc3ccccc3)cc2F)c(=O)c2nsnc21] | 6-[2,6-Difluoro-4-(2-phenylethynyl)phenyl]-4-isopropyl-[1,2,5]thiadiazolo[3,4-d]pyrimidine-5,7-dione | 23 | 104 |
| 41 | 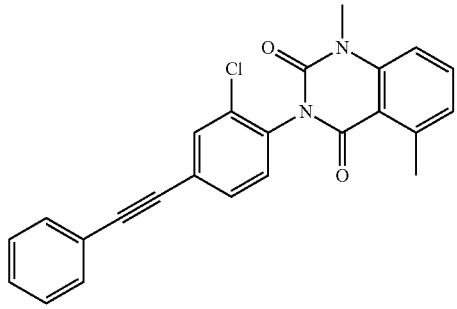 [SMILES: Cc1cccc2c1c(=O)n(-c1ccc(C#Cc3ccccc3)cc1Cl)c(=O)n2C] | 3-[2-Chloro-4-(2-phenylethynyl)phenyl]-1,5-dimethyl-quinazoline-2,4-dione | 231 | 98 |
| 42 | 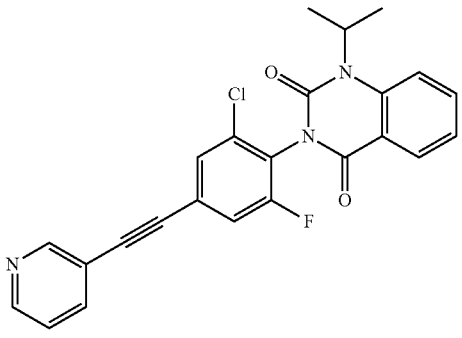 [SMILES: CC(C)n1c(=O)n(-c2c(F)cc(C#Cc3cccnc3)cc2Cl)c(=O)c2ccccc21] | 3-[2-Chloro-6-fluoro-4-[2-(3-pyridyl)ethynyl]phenyl]-1-isopropyl-quinazoline-2,4-dione | 83 | 80 |

-continued

List of Examples and data:

| Ex. | Structure | Name | EC$_{50}$ (nM) mGlu4PAM | Eff. (%) |
|---|---|---|---|---|
| 43 | 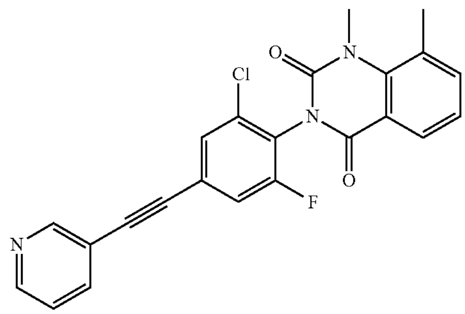 | 3-[2-Chloro-6-fluoro-4-[2-(3-pyridyl)ethynyl]phenyl]-1,8-dimethyl-quinazoline-2,4-dione | 74 | 107 |
| 44 | 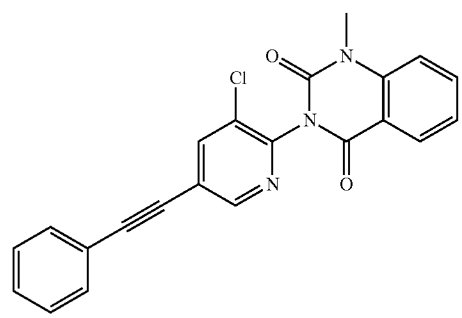 [SMILES: Cn1c(=O)n(-c2ncc(C#Cc3ccccc3)cc2Cl)c(=O)c2ccccc21] | 3-[3-Chloro-5-(2-phenylethynyl)-2-pyridyl]-1-methyl-quinazoline-2,4-dione | 372 | 180 |
| 45 | 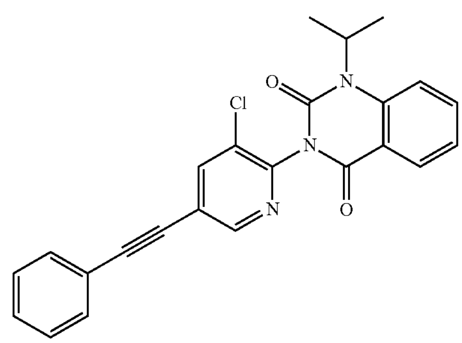 [SMILES: CC(C)n1c(=O)n(-c2ncc(C#Cc3ccccc3)cc2Cl)c(=O)c2ccccc21] | 3-[3-Chloro-5-(2-phenylethynyl)-2-pyridyl]-1-isopropyl-quinazoline-2,4-dione | 137 | 92 |
| 46 | 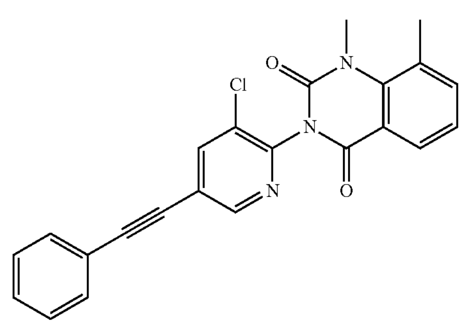 | 3-[3-Chloro-5-(2-phenylethynyl)-2-pyridyl]-1,8-dimethyl-quinazoline-2,4-dione | 141 | 113 |

-continued

List of Examples and data:

| Ex. | Structure | Name | EC$_{50}$ (nM) mGlu4PAM | Eff. (%) |
|---|---|---|---|---|
| 47 | 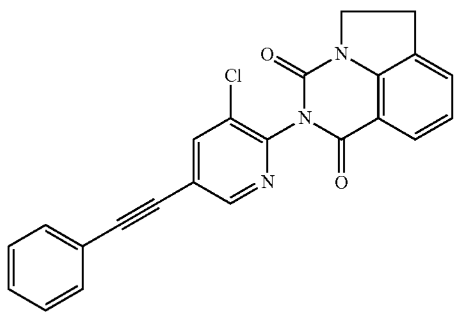 [SMILES: O=c1c2cccc3c2n(c(=O)n1-c1ncc(C#Cc2ccccc2)cc1Cl)CC3] | 2-(3-Chloro-5-(phenylethynyl)pyridin-2-yl)-5,6-dihydro-1H-pyrrolo[3,2,1-ij]quinazoline-1,3(2H)-dione | 187 | 110 |
| 48 | 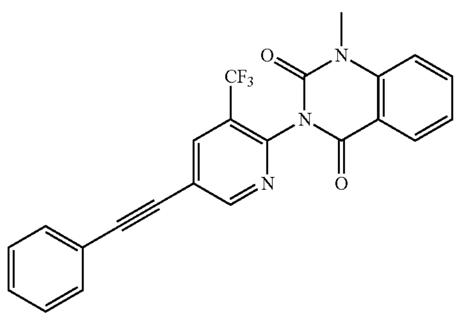 | 1-Methyl-3-[5-(2-phenylethynyl)-3-(trifluoromethyl)-2-pyridyl]quinazoline-2,4-dione | 175 | 95 |
| 49 | 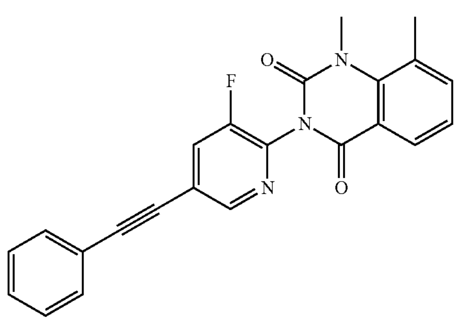 [SMILES: Cc1cccc2c(=O)n(-c3ncc(C#Cc4ccccc4)cc3F)c(=O)n(C)c12] | 3-[3-Fluoro-5-(2-phenylethynyl)-2-pyridyl]-1,8-dimethyl-quinazoline-2,4-dione | 302 | 111 |
| 50 | 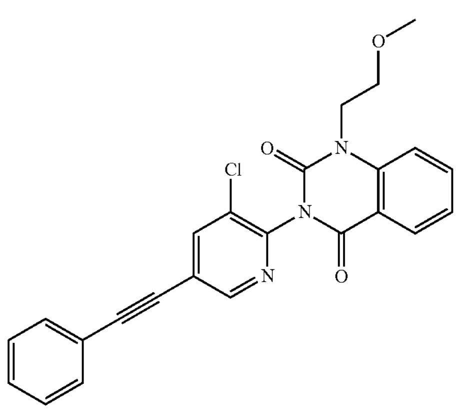 [SMILES: COCCn1c(=O)n(-c2ncc(C#Cc3ccccc3)cc2Cl)c(=O)c2ccccc21] | 3-[2-(Chloro-4-(2-phenylethynyl)phenyl]-1-(2-methoxyethyl)quinazoline-2,4-dione | 499 | 110 |

-continued

List of Examples and data:

| Ex. | Structure | Name | EC$_{50}$ (nM) mGlu4PAM | Eff. (%) |
|---|---|---|---|---|
| 51 | 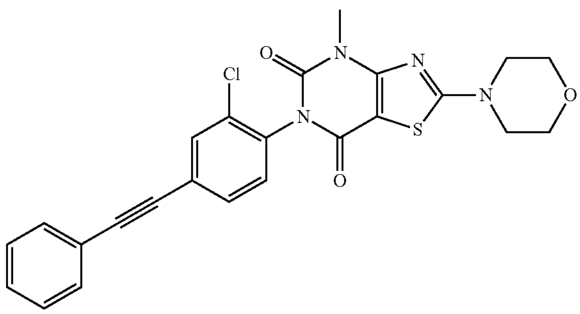 [SMILES: Cn1c(=O)n(-c2ccc(C#Cc3ccccc3)cc2Cl)c(=O)c2sc(N3CCOCC3)nc21] | 6-[2-Chloro-4-(2-phenylethynyl)phenyl]-4-methyl-2-morpholino-thiazolo[4,5-d]pyrimidine-5,7-dione | 164 | 127 |
| 52 | 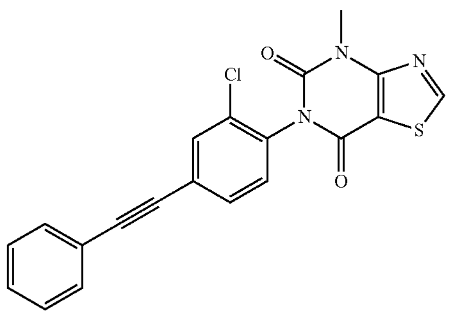 [SMILES: Cn1c(=O)n(-c2ccc(C#Cc3ccccc3)cc2Cl)c(=O)c2scnc21] | 6-[2-Chloro-4-(2-phenylethynyl)phenyl]-4-methyl-thiazolo[4,5-d]pyrimidine-5,7-dione | 200 | 110 |
| 53 | 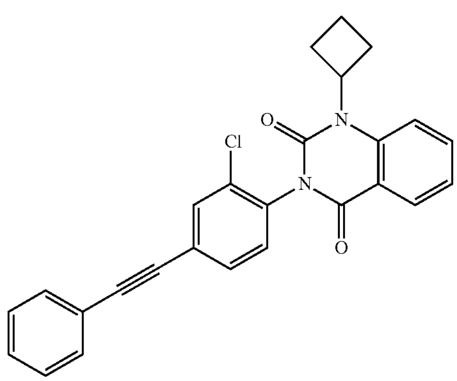 [SMILES: O=c1c2ccccc2n(C2CCC2)c(=O)n1-c1ccc(C#Cc2ccccc2)cc1Cl] | 3-[2-Chloro-4-(2-phenylethynyl)phenyl]-1-cyclobutyl-quinazoline-2,4-dione | 102 | 123 |
| 54 | 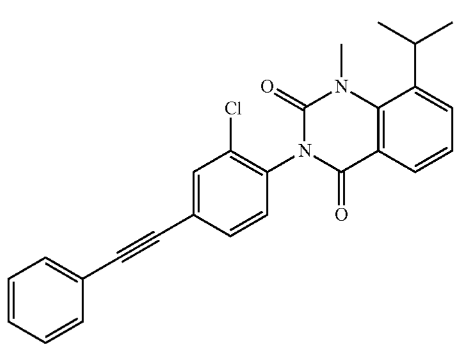 [SMILES: CC(C)c1cccc2c(=O)n(-c3ccc(C#Cc4ccccc4)cc3Cl)c(=O)n(C)c12] | 3-[2-Chloro-4-(2-phenylethynyl)phenyl]-8-isopropyl-1-methyl-quinazoline-2,4-dione | 179 | 97 |

-continued

List of Examples and data:

| Ex. | Structure | Name | EC$_{50}$ (nM) mGlu4PAM | Eff. (%) |
|---|---|---|---|---|
| 55 | 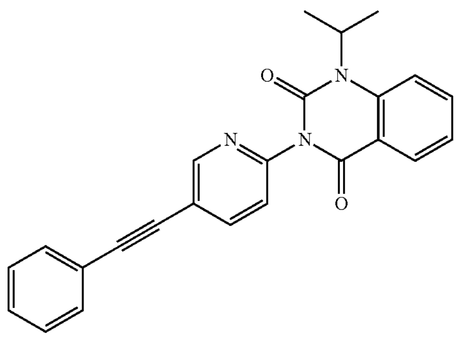 [SMILES: CC(C)n1c(=O)n(-c2ccc(C#Cc3ccccc3)cn2)c(=O)c2ccccc21] | 1-Isopropyl-3-[5-(2-phenylethynyl)-2-pyridyl]quinazoline-2,4-dione | 766 | 123 |
| 56 | 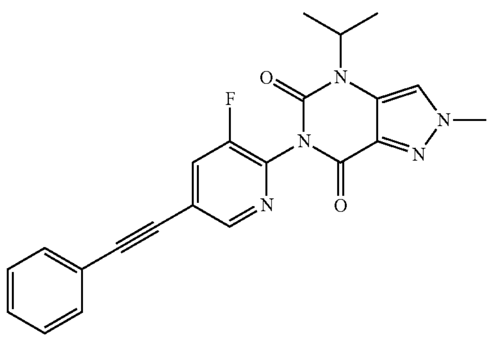 [SMILES: CC(C)n1c(=O)n(-c2ncc(C#Cc3ccccc3)cc2F)c(=O)c2nn(C)cc21] | 6-[3-Fluoro-5-(2-phenylethynyl)-2-pyridyl]-4-isopropyl-2-methyl-pyrazolo[4,3-d]pyrimidine-5,7-dione | 121 | 120 |
| 57 | 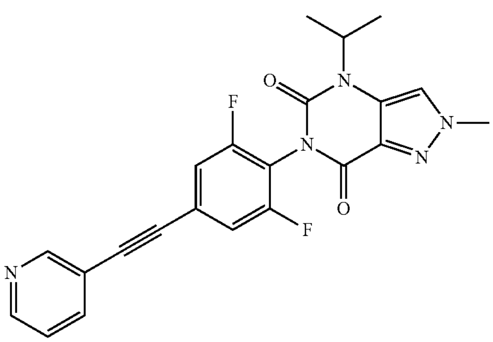 [SMILES: CC(C)n1c(=O)n(-c2c(F)cc(C#Cc3cccnc3)cc2F)c(=O)c2nn(C)cc21] | 6-[2,6-Difluoro-4-[2-(3-pyridyl)ethynyl]phenyl]-4-isopropyl-2-methyl-pyrazolo[4,3-d]pyrimidine-5,7-dione | 65 | 134 |
| 58 | 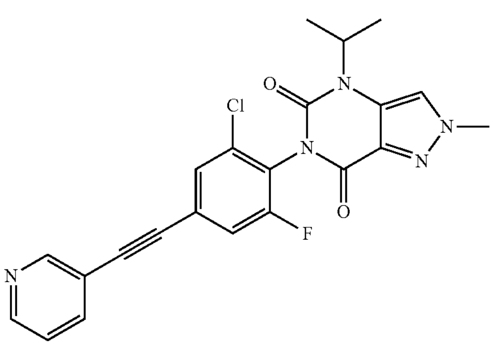 | 6-[2-Chloro-6-fluoro-4-[2-(3-pyridyl)ethynyl]phenyl]-4-isopropyl-2-methyl-pyrazolo[4,3-d]pyrimidine-5,7-dione | 37 | 120 |

-continued

| Ex. | Structure | Name | EC$_{50}$ (nM) mGlu4PAM | Eff. (%) |
|---|---|---|---|---|
| 59 | 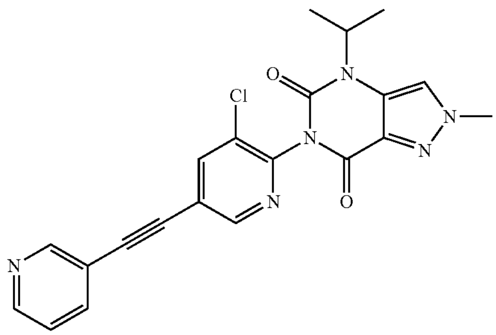 [SMILES: CC(C)n1c(=O)n(-c2ncc(C#Cc3cccnc3)cc2Cl)c(=O)c2nn(C)cc21] | 6-[3-Chloro-5-[2-(3-pyridyl)ethynyl]-2-pyridyl]-4-isopropyl-2-methyl-pyrazolo[4,3-d]pyrimidine-5,7-dione | 169 | 146 |
| 60 | 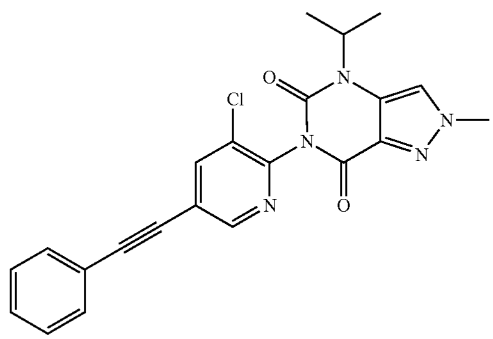 | 6-[3-Chloro-5-(2-phenylethynyl)-2-pyridyl]-4-isopropyl-2-methyl-pyrazolo[4,3-d]pyrimidine-5,7-dione | 189 | 150 |
| 61 | 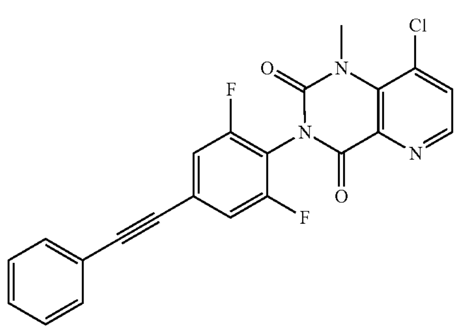 [SMILES: Cn1c(=O)n(-c2c(F)cc(C#Cc3ccccc3)cc2F)c(=O)c2nccc(Cl)c21] | 8-Chloro-3-[2,6-difluoro-4-(2-phenylethynyl)phenyl]-1-methyl-pyrido[3,2-d]pyrimidine-2,4-dione | 91 | 129 |
| 62 | 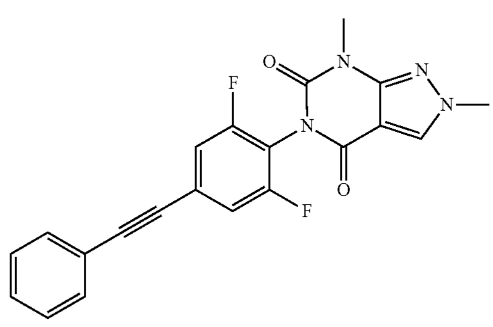 | 5-[2,6-Difluoro-4-(2-phenylethynyl)phenyl]-2,7-dimethyl-pyrazolo[3,4-d]pyrimidine-4,6-dione | 137 | 145 |

-continued

| | List of Examples and data: | | | |
|---|---|---|---|---|
| Ex. | Structure | Name | EC$_{50}$ (nM) mGlu4PAM | Eff. (%) |
| 63 | | 5-[2,6-Difluoro-4-(2-phenylethynyl)phenyl]-1,7-dimethyl-pyrazolo[3,4-d]pyrimidine-4,6-dione | 26 | 146 |
| 64 | | 5-[2,6-Difluoro-4-(2-phenylethynyl)phenyl]-7-isopropyl-2H-pyrazolo[3,4-d]pyrimidine-4,6-dione | 121 | 120 |
| 65 | | 3-[2-Chloro-4-(2-phenylethynyl)phenyl]-8-methoxy-1-methyl-quinazoline-2,4-dione | 32 | 97 |
| 66 | | 3-[2,6-Difluoro-4-(2-phenylethynyl)phenyl]-1-(oxetan-3-yl)quinazoline-2,4-dione | 75 | 184 |

-continued

List of Examples and data:

| Ex. | Structure | Name | EC$_{50}$ (nM) mGlu4PAM | Eff. (%) |
|---|---|---|---|---|
| 67 | 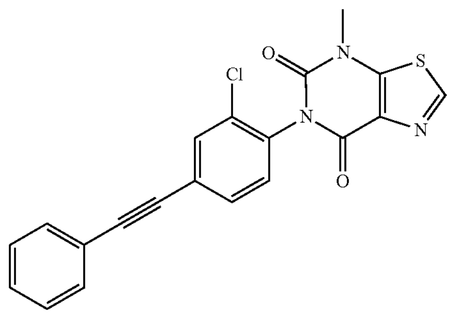 [SMILES: Cn1c(=O)n(-c2ccc(C#Cc3ccccc3)cc2Cl)c(=O)c2ncsc21] | 6-[2-(Chloro-4-(2-phenylethynyl)phenyl]-4-methyl-thiazolo[5,4-d]pyrimidine-5,7-dione | 246 | 188 |
| 68 | 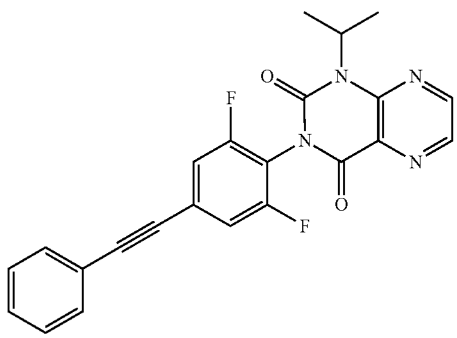 [SMILES: CC(C)n1c(=O)n(-c2c(F)cc(C#Cc3ccccc3)cc2F)c(=O)c2nccnc21] | 3-[2,6-Difluoro-4-(2-phenylethynyl)phenyl]-1-isopropyl-pteridine-2,4-dione | 48 | 225 |
| 69 | 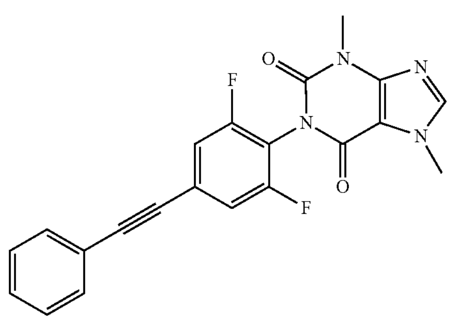 [SMILES: Cn1cnc2c1c(=O)n(-c1c(F)cc(C#Cc3ccccc3)cc1F)c(=O)n2C] | 1-[2,6-Difluoro-4-(2-phenylethynyl)phenyl]-3,7-dimethyl-purine-2,6-dione | 50 | 113 |
| 70 | 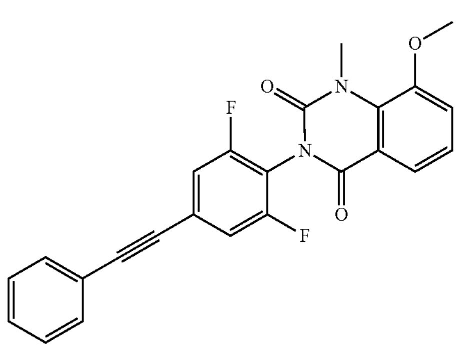 [SMILES: COc1cccc2c(=O)n(-c3c(F)cc(C#Cc4ccccc4)cc3F)c(=O)n(C)c12] | 3-[2,6-Difluoro-4-(2-phenylethynyl)phenyl]-8-methoxy-1-methyl-quinazoline-2,4-dione | 38 | 152 |

-continued

List of Examples and data:

| Ex. | Structure | Name | EC$_{50}$ (nM) mGlu4PAM | Eff. (%) |
|---|---|---|---|---|
| 71 | 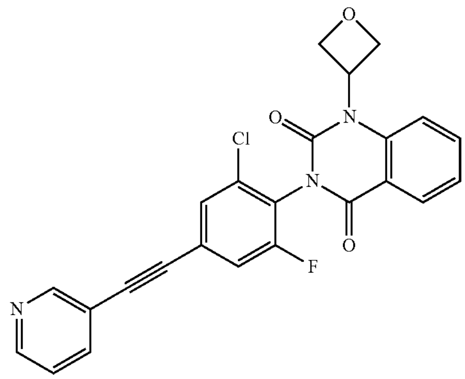 [SMILES: O=c1c2ccccc2n(C2COC2)c(=O)n1-c1c(F)cc(C#Cc2cccnc2)cc1Cl] | 3-[2-Chloro-6-fluoro-4-[2-(3-pyridyl)ethynyl]phenyl]-1-(oxetan-3-yl)quinazoline-2,4-dione | 86 | 103 |
| 72 | 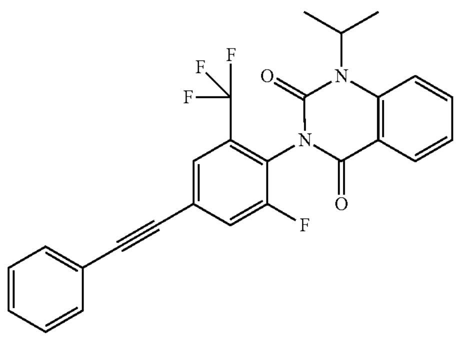 [SMILES: CC(C)n1c(=O)n(-c2c(F)cc(C#Cc3ccccc3)cc2C(F)(F)F)c(=O)c2ccccc21] | 3-[2-Fluoro-4-(2-phenylethynyl)-6-(trifluoromethyl)phenyl]-1-isopropyl-quinazoline-2,4-dione | 63 | 134 |
| 73 | 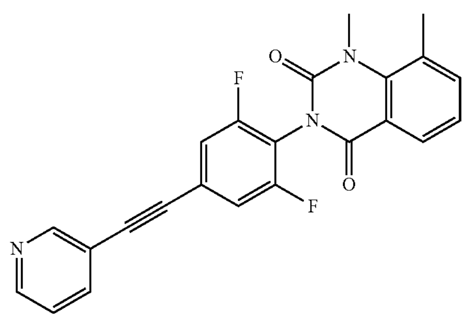 | 3-[2,6-Difluoro-4-[2-(3-pyridyl)ethynyl]phenyl]-1,8-dimethyl-quinazoline-2,4-dione | 154 | 197 |
| 74 | 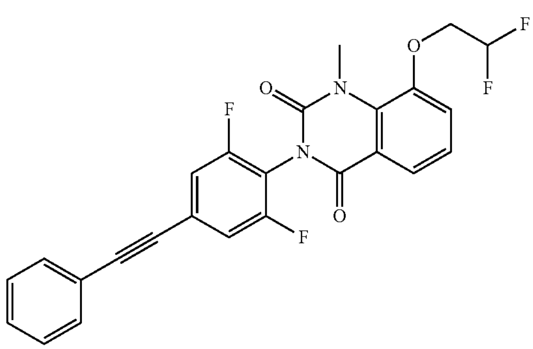 [SMILES: Cn1c(=O)n(-c2c(F)cc(C#Cc3ccccc3)cc2F)c(=O)c2cccc(OCC(F)F)c21] | 8-(2,2-Difluoroethoxy)-3-[2,6-difluoro-4-(2-phenylethynyl)phenyl]-1-methyl-quinazoline-2,4-dione | 60 | 122 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethyl starch | 10 |
| Magnesium stearate | 2 |
| Tablet weight | 250 |

EXPERIMENTAL SECTION

Example 1

3-[2-Chloro-4-(2-phenylethynyl)phenyl]-1-methyl-quinazoline-2,4-dione

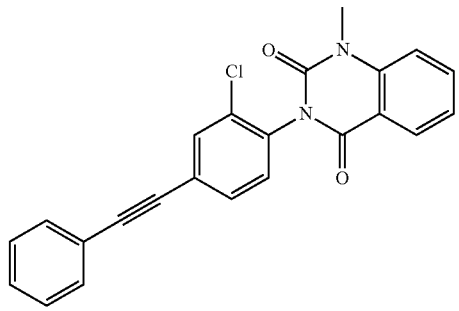

Step 1: 2-Chloro-4-iodo-1-isocyanato-benzene

2-Chloro-4-iodoaniline (500 mg, 1.97 mmol) was dissolved in toluene (5 ml) and bis(trichloromethyl) carbonate (234 mg, 0.79 mmol, 0.4 equiv.) was added at room temperature. The mixture was stirred for 16 hours at 110° C. The reaction mixture was evaporated and the residue was suspended in 5 ml heptane. The suspension was filtered and the filtrate evaporated to dryness. The desired 2-chloro-4-iodo-1-isocyanato-benzene (400 mg, 73% yield) was obtained as a light yellow solid and used in the next step without further characterization.

Step 2: 3-(2-Chloro-4-iodo-phenyl)-1H-quinazoline-2,4-dione

Methyl 2-aminobenzoate (100 mg, 0.66 mmol) was dissolved in dioxane (1.5 ml) and 2-chloro-4-iodo-1-isocyanato-benzene (Example 1, step 1) (203 mg, 0.73 mmol, 1.1 equiv.) and triethylamine (250 µl, 1.79 mmol, 2.7 equiv.) were added at room temperature. The mixture was stirred for 16 hours at 85° C. The reaction mixture was evaporated and the residue was crystallized from heptane and ethyl acetate to yield the desired 3-(2-chloro-4-iodo-phenyl)-1H-quinazoline-2,4-dione (155 mg, 59% yield) as a white solid, MS: m/e=399.0/401.0 (M+H$^+$).

Step 3: 3-[2-Chloro-4-(2-phenylethynyl)phenyl]-1H-quinazoline-2,4-dione

Bis-(triphenylphosphine)-palladium(II)dichloride (8 mg, 11.7 µmol, 0.03 equiv.) was dissolved in 2 ml DMF. (155 mg, 389 µmol) 3-(2-Chloro-4-iodo-phenyl)-1H-quinazoline-2,4-dione (Example 1, step 2) and phenylacetylene (79 mg, 85 µl, 0.778 mmol, 2 equiv.) were added at room temperature. Triethylamine (157 mg, 217 µl, 1.56 mmol, 4 equiv.), triphenylphosphine (6 mg, 23.4 µmol, 0.06 equiv.) and copper(I)iodide (2 mg, 7.8 µmol, 0.02 equiv.) were added and the mixture was stirred for 2 hours at 50° C. The reaction mixture was cooled and extracted with saturated NaHCO$_3$ solution and two times with ethyl acetate. The organic layers were washed three times with water, dried over sodium sulfate and evaporated to dryness. The crude product was purified by flash chromatography on a silica gel column eluting with an ethyl acetate:heptane gradient 0:100 to 50:50. The desired 3-[2-chloro-4-(2-phenylethynyl)phenyl]-1H-quinazoline-2,4-dione (135 mg, 93% yield) was obtained as a light yellow solid, MS: m/e=373.1/375.1 (M+H$^+$).

Step 4: 3-[2-Chloro-4-(2-phenylethynyl)phenyl]-1-methyl-quinazoline-2,4-dione (110 mg, 295 µmol) 3-[2-Chloro-4-(2-phenylethynyl)phenyl]-1H-quinazoline-2,4-dione (Example 1, step 3) was dissolved in acetone (3 ml) and potassium carbonate (82 mg, 0.59 mmol, 2 equiv.) and iodomethane (251 mg, 111 µl, 1.77 mmol, 6 equiv.) were added at room temperature. The mixture was stirred for 16 hours at room temperature. The reaction mixture was evaporated to dryness and the crude product was purified directly by flash chromatography on a silica gel column eluting with an ethyl acetate:heptane gradient 0:100 to 50:50. The desired 3-[2-chloro-4-(2-phenylethynyl)phenyl]-1-methyl-quinazoline-2,4-dione (92 mg, 81% yield) was obtained as a light yellow solid, MS: m/e=387.1/389.2 (M+H$^+$).

Example 2

3-[2-Chloro-4-(2-phenylethynyl)phenyl]-1,8-dimethyl-quinazoline-2,4-dione

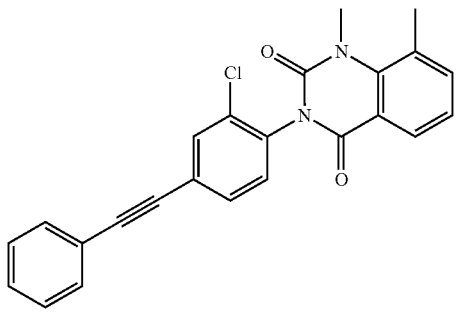 [SMILES: Cc1cccc2c(=O)n(-c3ccc(C#Cc4ccccc4)cc3Cl)c(=O)n(C)c12]

Step 1: 3-(2-Chloro-4-iodo-phenyl)-8-methyl-1H-quinazoline-2,4-dione

The title compound was obtained as a white solid, MS: m/e=413.0/415.0 (M+H$^+$), using chemistry similar to that described in Example 1, step 2 from 2-chloro-4-iodo-1-isocyanato-benzene (Example 1, step 1) and methyl 2-amino-3-methylbenzoate.

Step 2: 3-[2-chloro-4-(2-phenylethynyl)phenyl]-8-methyl-1H-quinazoline-2,4-dione The title compound was obtained as a light brown solid, MS: m/e=387.1/389.1 (M+H$^+$), using chemistry similar to that described in Example 1, step 3 from 3-(2-chloro-4-iodo-phenyl)-8-methyl-1H-quinazoline-2,4-dione (Example 2, step 1) and phenylacetylene.

Step 3: 3-[2-Chloro-4-(2-phenylethynyl)phenyl]-1,8-dimethyl-quinazoline-2,4-dione The title compound was obtained as a light brown solid, MS: m/e=401.1/403.2 (M+H$^+$), using chemistry similar to that described in Example 1, step 4 from 3-[2-chloro-4-(2-phenylethynyl)phenyl]-8-methyl-1H-quinazoline-2,4-dione (Example 2, step 2) and iodomethane.

Example 3

8-Chloro-3-[2-chloro-4-(2-phenylethynyl)phenyl]-1-methyl-quinazoline-2,4-dione

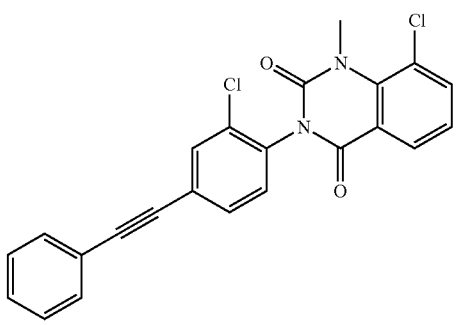 [SMILES: Cn1c(=O)n(-c2ccc(C#Cc3ccccc3)cc2Cl)c(=O)c2cccc(Cl)c21]

Step 1: 8-Chloro-3-(2-chloro-4-iodo-phenyl)-1H-quinazoline-2,4-dione

The title compound was obtained as a light yellow solid, MS: m/e=433.0/435.0 (M+H$^+$), using chemistry similar to that described in Example 1, step 2 from 2-chloro-4-iodo-1-isocyanato-benzene (Example 1, step 1) and methyl 2-amino-3-chlorobenzoate.

Step 2: 8-Chloro-3-[2-chloro-4-(2-phenylethynyl)phenyl]-1H-quinazoline-2,4-dione The title compound was obtained as a light yellow solid, MS: m/e=405.2/407.2 (M–H$^+$), using chemistry similar to that described in Example 1, step 3 from 8-chloro-3-(2-chloro-4-iodo-phenyl)-1H-quinazoline-2,4-dione (Example 3, step 1) and phenylacetylene.

Step 3: 8-Chloro-3-[2-chloro-4-(2-phenylethynyl)phenyl]-1-methyl-quinazoline-2,4-dione The title compound was obtained as a light brown solid, MS: m/e=421.1/423.1 (M+H$^+$), using chemistry similar to that described in Example 1, step 4 from 8-chloro-3-[2-chloro-4-(2-phenylethynyl)phenyl]-1H-quinazoline-2,4-dione (Example 3, step 2) and iodomethane.

Example 4

7-Chloro-3-[2-chloro-4-(2-phenylethynyl)phenyl]-1-methyl-quinazoline-2,4-dione

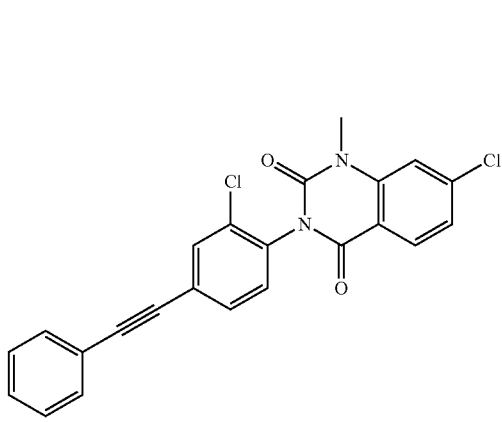 [SMILES: Cn1c(=O)n(-c2ccc(C#Cc3ccccc3)cc2Cl)c(=O)c2ccc(Cl)cc21]

Step 1: 2-Chloro-4-(2-phenylethynyl)aniline

The title compound was obtained as a yellow solid, MS: m/e=228.1/230.1 (M+H$^+$), using chemistry similar to that described in Example 1, step 3 from 2-chloro-4-iodoaniline and phenylacetylene.

Step 2: 2-Chloro-1-isocyanato-4-(2-phenylethynyl)benzene

The title compound was obtained as a dark brown waxy solid, using chemistry similar to that described in Example 1, step 1 from 2-chloro-4-(2-phenylethynyl)aniline (Example 4, step 1).

Step 3: 7-Chloro-3-[2-chloro-4-(2-phenylethynyl)phenyl]-1H-quinazoline-2,4-dione The title compound was obtained as a yellow solid, MS: m/e=405.2/407.2 (M−H$^+$), using chemistry similar to that described in Example 1, step 2 from 2-chloro-1-isocyanato-4-(2-phenylethynyl)benzene (Example 4, step 2) and methyl 2-amino-4-chlorobenzoate.

Step 3: 7-Chloro-3-[2-chloro-4-(2-phenylethynyl)phenyl]-1-methyl-quinazoline-2,4-dione The title compound was obtained as a yellow solid, MS: m/e=421.1/423.1 (M+H$^+$), using chemistry similar to that described in Example 1, step 4 from 7-chloro-3-[2-chloro-4-(2-phenylethynyl)phenyl]-1H-quinazoline-2,4-dione (Example 4, step 3) and iodomethane.

Example 5

3-[2-Chloro-4-(2-phenylethynyl)phenyl]-1,7-dimethyl-quinazoline-2,4-dione

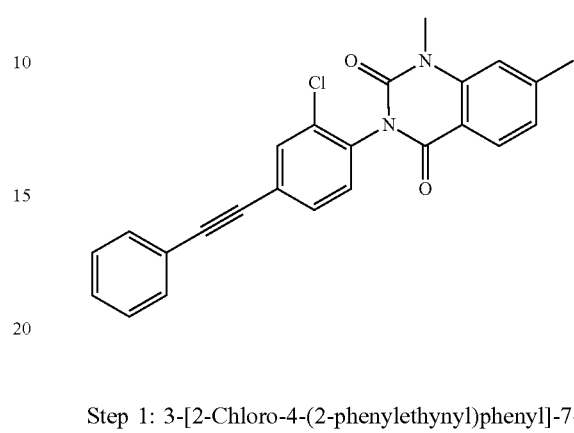

Step 1: 3-[2-Chloro-4-(2-phenylethynyl)phenyl]-7-methyl-1H-quinazoline-2,4-dione The title compound was obtained as a white solid, MS: m/e=387.1/389.2 (M+H$^+$), using chemistry similar to that described in Example 1, step 2 from 2-chloro-1-isocyanato-4-(2-phenylethynyl)benzene (Example 4, step 2) and methyl 2-amino-4-methylbenzoate.

Step 2: 3-[2-Chloro-4-(2-phenylethynyl)phenyl]-1,7-dimethyl-quinazoline-2,4-dione The title compound was obtained as a light yellow solid, MS: m/e=401.1/403.2 (M+H$^+$), using chemistry similar to that described in Example 1, step 4 from 3-[2-chloro-4-(2-phenylethynyl)phenyl]-7-methyl-1H-quinazoline-2,4-dione (Example 5, step 1) and iodomethane.

Example 6

3-[2-Chloro-4-(2-phenylethynyl)phenyl]-1H-pyrido[2,3-d]pyrimidine-2,4-dione

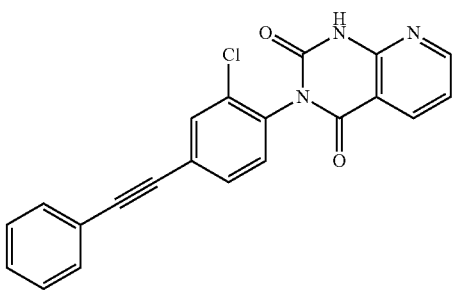 [SMILES: O=c1[nH]c2ncccc2c(=O)n1-c1ccc(C#Cc2ccccc2)cc1Cl]

The title compound was obtained as a light brown solid, MS: m/e=374.1/376.1 (M+H$^+$), using chemistry similar to that described in Example 1, step 2 from 2-chloro-1-isocyanato-4-(2-phenylethynyl)benzene (Example 4, step 2) and methyl 2-aminonicotinateethyl.

Example 7

3-[2-Chloro-4-(2-phenylethynyl)phenyl]-1-methyl-pyrido[2,3-d]pyrimidine-2,4-dione

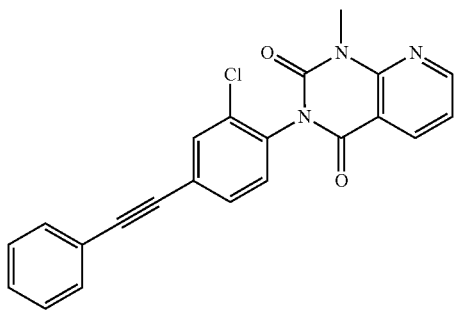 [SMILES: Cn1c(=O)n(-c2ccc(C#Cc3ccccc3)cc2Cl)c(=O)c2cccnc21]

The title compound was obtained as a light yellow solid, MS: m/e=388.1/390.1 (M+H$^+$), using chemistry similar to that described in Example 1, step 4 from 3-[2-chloro-4-(2-phenylethynyl)phenyl]-1H-pyrido[2,3-d]pyrimidine-2,4-dione (Example 6) and iodomethane.

Example 8

3-[2-Chloro-4-(2-phenylethynyl)phenyl]-8-ethyl-1-methyl-quinazoline-2,4-dione

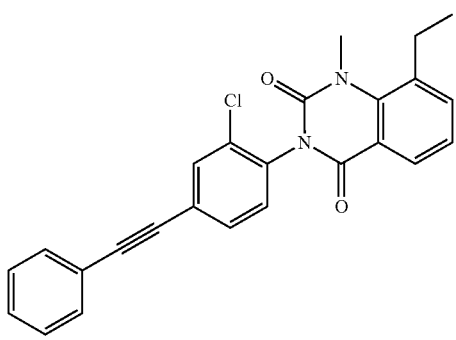

Step 1: 3-[2-Chloro-4-(2-phenylethynyl)phenyl]-8-ethyl-1H-quinazoline-2,4-dione The title compound was obtained as a brown solid, MS: m/e=401.2/403.3 (M+H$^+$), using chemistry similar to that described in Example 1, step 2 from 2-chloro-1-isocyanato-4-(2-phenylethynyl)benzene (Example 4, step 2) and methyl 2-amino-3-ethylbenzoate.

Step 2: 3-[2-Chloro-4-(2-phenylethynyl)phenyl]-8-ethyl-1-methyl-quinazoline-2,4-dione The title compound was obtained as a light brown solid, MS: m/e=415.1/417.2 (M+H$^+$), using chemistry similar to that described in Example 1, step 4 from 3-[2-chloro-4-(2-phenylethynyl)phenyl]-8-ethyl-1H-quinazoline-2,4-dione (Example 8, step 1) and iodomethane.

Example 9

3-[2-Chloro-4-(2-phenylethynyl)phenyl]-1-methyl-pyrido[3,2-d]pyrimidine-2,4-dione

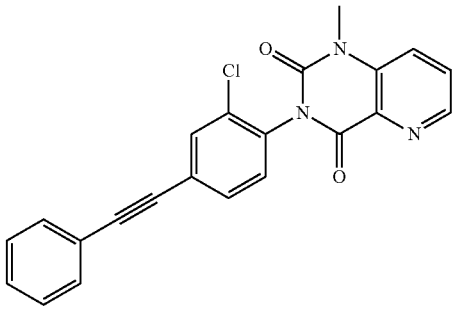 [SMILES: Cn1c(=O)n(-c2ccc(C#Cc3ccccc3)cc2Cl)c(=O)c2ncccc21]

Step 1: 3-[2-Chloro-4-(2-phenylethynyl)phenyl]-1H-pyrido[3,2-d]pyrimidine-2,4-dione The title compound was obtained as a light brown solid, MS: m/e=374.3/376.3 (M+H$^+$), using chemistry similar to that described in Example 1, step 2 from 2-chloro-1-isocyanato-4-(2-phenylethynyl)benzene (Example 4, step 2) and ethyl 3-aminopicolinate.

Step 2: 3-[2-Chloro-4-(2-phenylethynyl)phenyl]-1-methyl-pyrido[3,2-d]pyrimidine-2,4-dione The title compound was obtained as a light yellow solid, MS: m/e=388.2/390.3 (M+H$^+$), using chemistry similar to that described in Example 1, step 4 from 3-[2-chloro-4-(2-phenylethynyl)phenyl]-1H-pyrido[3,2-d]pyrimidine-2,4-dione (Example 9, step 1) and iodomethane.

Example 10

3-[2-Chloro-4-(2-phenylethynyl)phenyl]-1-methyl-pyrido[4,3-d]pyrimidine-2,4-dione

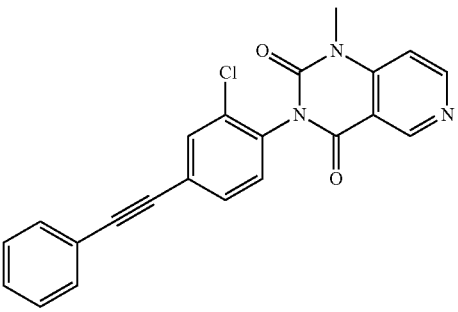 [SMILES: Cn1c(=O)n(-c2ccc(C#Cc3ccccc3)cc2Cl)c(=O)c2cnccc21]

Step 1: 3-(2-Chloro-4-iodo-phenyl)-1H-pyrido[4,3-d]pyrimidine-2,4-dione

2-Chloro-4-iodoaniline (200 mg, 0.79 mmol) was dissolved in toluene (2.0 ml) and methyl 4-aminonicotinate (120 mg, 0.79 mmol, 1.0 equiv.) and CDI (154 mg, 0.95 mmol, 1.2 equiv.) were added at room temperature. The mixture was stirred for 16 hours at 110° C. The reaction mixture was loaded directly onto a silica gel column. The crude product was purified by flash chromatography eluting with an ethyl acetate:heptane gradient 0:100 to 100:0. The desired 3-(2-chloro-4-iodo-phenyl)-1H-pyrido[4,3-d]pyrimidine-2,4-dione (110 mg, 35% yield) was obtained as a white solid, MS: m/e=400.0/402.0 (M+H⁺).

Step 2: 3-[2-Chloro-4-(2-phenylethynyl)phenyl]-1H-pyrido[4,3-d]pyrimidine-2,4-dione The title compound was obtained as a yellow solid, MS: m/e=374.1/376.1 (M+H⁺), using chemistry similar to that described in Example 1, step 3 from 3-(2-chloro-4-iodo-phenyl)-1H-pyrido[4,3-d]pyrimidine-2,4-dione (Example 10, step 1) and phenylacetylene.

Step 3: 3-[2-Chloro-4-(2-phenylethynyl)phenyl]-1-methyl-pyrido[4,3-d]pyrimidine-2,4-dione The title compound was obtained as a light yellow solid, MS: m/e=388.1/390.2 (M+H⁺), using chemistry similar to that described in Example 1, step 4 from 3-[2-chloro-4-(2-phenylethynyl)phenyl]-1H-pyrido[4,3-d]pyrimidine-2,4-dione (Example 10, step 2) and iodomethane.

Example 11

1-[2-Chloro-4-(2-phenylethynyl)phenyl]-3,7-dimethyl-purine-2,6-dione

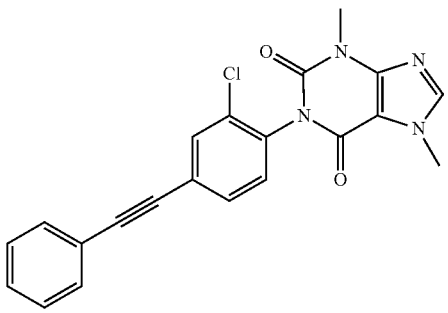 [SMILES: Cn1cnc2c1c(=O)n(-c1ccc(C#Cc3ccccc3)cc1Cl)c(=O)n2C]

Step 1: Ethyl 5-[(2-chloro-4-iodo-phenyl)carbamoylamino]-3-methyl-imidazole-4-carboxylate The title compound was obtained as a white solid, MS: m/e=449.1/451.1 (M–H⁺), using chemistry similar to that described in Example 10, step 1 from 2-chloro-4-iodoaniline and ethyl 4-amino-1-methyl-1H-imidazole-5-carboxylate.

Step 2: 1-(2-Chloro-4-iodo-phenyl)-7-methyl-3H-purine-2,6-dione

Ethyl 5-[(2-chloro-4-iodo-phenyl)carbamoylamino]-3-methyl-imidazole-4-carboxylate (Example 11, step 1) (330 mg, 0.74 mmol) was dissolved in THF (5.0 ml) and KOtBu (124 mg, 1.1 mmol, 1.5 equiv.) was added at room temperature. The mixture was stirred for 16 hours at room temperature. The reaction mixture was extracted with saturated NaHCO₃ solution and two times with ethyl acetate. The organic layers were washed with saturated NaCl solution, dried over sodium sulfate and evaporated to dryness. The desired 1-(2-chloro-4-iodo-phenyl)-7-methyl-3H-purine-2,6-dione (220 mg, 74% yield) was obtained as a light yellow solid, MS: m/e=403.0/405.0 (M+H⁺).

Step 3: 1-[2-Chloro-4-(2-phenylethynyl)phenyl]-7-methyl-3H-purine-2,6-dione

The title compound was obtained as a light yellow solid, MS: m/e=377.1/379.0 (M+H⁺), using chemistry similar to that described in Example 1, step 3 from 1-(2-chloro-4-iodo-phenyl)-7-methyl-3H-purine-2,6-dione (Example 11, step 2) and phenylacetylene.

Step 4: 1-[2-Chloro-4-(2-phenylethynyl)phenyl]-3,7-dimethyl-purine-2,6-dione

The title compound was obtained as a yellow solid, MS: m/e=391.1/393.1 (M+H⁺), using chemistry similar to that described in Example 1, step 4 from 1-[2-chloro-4-(2-phenylethynyl)phenyl]-7-methyl-3H-purine-2,6-dione (Example 11, step 3) and iodomethane.

Example 12

2-(2-Chloro-4-(phenylethynyl)phenyl)-5,6-dihydro-H-pyrrolo[3,2,1-ij]quinazoline-1,3(2H)-dione

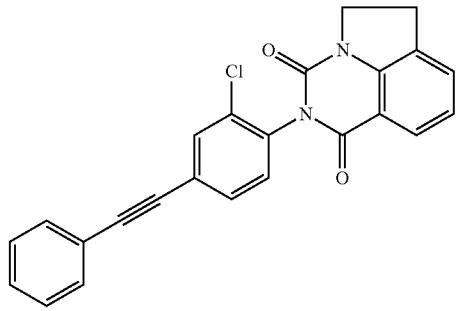 [SMILES: O=c1c2cccc3c2n(c(=O)n1-c1ccc(C#Cc2ccccc2)cc1Cl)CCC3]

The title compound was obtained as a white solid, MS: m/e=399.1/401.0 (M+H⁺), using chemistry similar to that described in Example 1, step 2 from 2-chloro-1-isocyanato-4-(2-phenylethynyl)benzene (Example 4, step 2) and methyl indoline-7-carboxylate.

Example 13

3-[2-Chloro-4-(2-phenylethynyl)phenyl]-1-isopropyl-quinazoline-2,4-dione

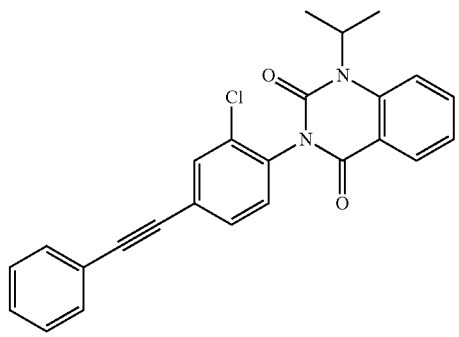

The title compound was obtained as a yellow oil, MS: m/e=415.2/417.1 (M+H+), using chemistry similar to that described in Example 1, step 4 from 3-[2-chloro-4-(2-phenylethynyl)phenyl]-1H-quinazoline-2,4-dione (Example 1, step 3) and 2-iodopropane.

Example 14

3-[2-Chloro-4-(2-phenylethynyl)phenyl]-1-ethyl-quinazoline-2,4-dione

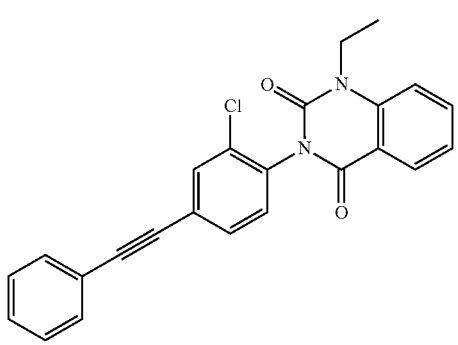 [SMILES: CCn1c(=O)n(-c2ccc(C#Cc3ccccc3)cc2Cl)c(=O)c2ccccc21]

The title compound was obtained as a yellow oil, MS: m/e=401.2/403.3 (M+H+), using chemistry similar to that described in Example 1, step 4 from 3-[2-chloro-4-(2-phenylethynyl)phenyl]-1H-quinazoline-2,4-dione (Example 1, step 3) and iodoethane.

Example 15

3-[2-Chloro-4-(2-phenylethynyl)phenyl]-1-methyl-pteridine-2,4-dione

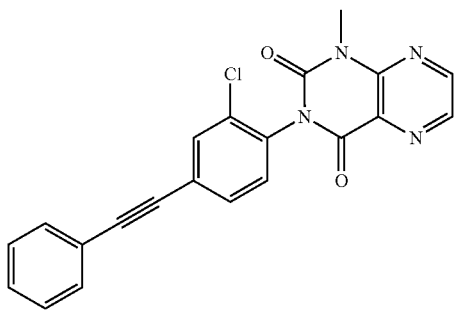 [SMILES: Cn1c(=O)n(-c2ccc(C#Cc3ccccc3)cc2Cl)c(=O)c2nccnc21]

Step 1: 3-[2-Chloro-4-(2-phenylethynyl)phenyl]-1H-pteridine-2,4-dione

The title compound was obtained as a light yellow solid, MS: m/e=375.2/377.2 (M−H+), using chemistry similar to that described in Example 10, step 1 from 2-chloro-4-(2-phenylethynyl)aniline (Example 4, step 1) and methyl 3-aminopyrazine-2-carboxylate.

Step 2: 3-[2-Chloro-4-(2-phenylethynyl)phenyl]-1-methyl-pteridine-2,4-dione

The title compound was obtained as a light yellow solid, MS: m/e=389.1/391.1 (M+H+), using chemistry similar to that described in Example 1, step 4 from 3-[2-chloro-4-(2-phenylethynyl)phenyl]-1H-pteridine-2,4-dione (Example 15, step 1) and iodomethane.

Example 16

3-[2-Chloro-4-(2-phenylethynyl)phenyl]-1H-pyrimido[4,5-d]pyrimidine-2,4-dione

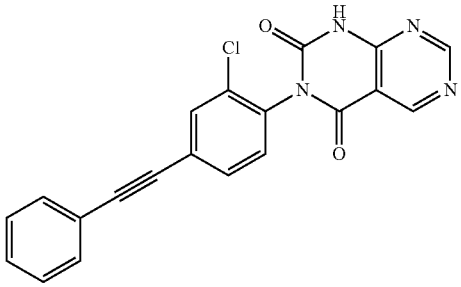 [SMILES: O=c1[nH]c2ncncc2c(=O)n1-c1ccc(C#Cc2ccccc2)cc1Cl]

The title compound was obtained as a yellow solid, MS: m/e=375.2/377.1 (M−H+), using chemistry similar to that described in Example 10, step 1 from 2-chloro-4-(2-phenylethynyl)aniline (Example 4, step 1) and methyl 4-aminopyrimidine-5-carboxylate.

Example 17

3-[2-Chloro-4-(2-phenylethynyl)phenyl]-1-methyl-pyrimido[4,5-d]pyrimidine-2,4-dione

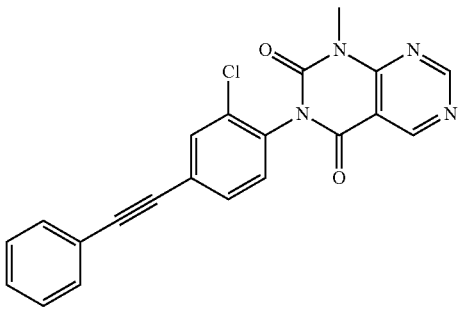 [SMILES: Cn1c(=O)n(-c2ccc(C#Cc3ccccc3)cc2Cl)c(=O)c2cncnc21]

The title compound was obtained as a light yellow solid, MS: m/e=389.2/391.1 (M+H+), using chemistry similar to that described in Example 1, step 4 from 3-[2-chloro-4-(2-phenylethynyl)phenyl]-1H-pyrimido[4,5-d]pyrimidine-2,4-dione (Example 16) and iodomethane.

Example 18

3-[2-Chloro-4-(2-phenylethynyl)phenyl]-6-fluoro-1-methyl-quinazoline-2,4-dione

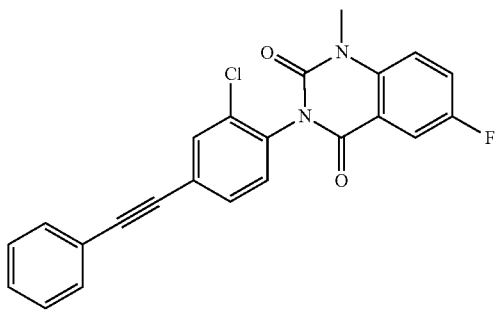 [SMILES: Cn1c(=O)n(-c2ccc(C#Cc3ccccc3)cc2Cl)c(=O)c2cc(F)ccc21]

Step 1: 3-[2-Chloro-4-(2-phenylethynyl)phenyl]-6-fluoro-1H-quinazoline-2,4-dione The title compound was obtained as a light brown solid, MS: m/e=391.1/393.1 (M+H$^+$), using chemistry similar to that described in Example 1, step 2 from 2-chloro-1-isocyanato-4-(2-phenylethynyl)benzene (Example 4, step 2) and methyl 2-amino-5-fluorobenzoate.

Step 2: 3-[2-Chloro-4-(2-phenylethynyl)phenyl]-6-fluoro-1-methyl-quinazoline-2,4-dione The title compound was obtained as a light yellow solid, MS: m/e=405.1/407.1 (M+H$^+$), using chemistry similar to that described in Example 1, step 4 from 3-[2-chloro-4-(2-phenylethynyl)phenyl]-6-fluoro-1H-quinazoline-2,4-dione (Example 18, step 1) and iodomethane.

Example 19

3-[2-Chloro-4-(2-phenylethynyl)phenyl]-7,8-difluoro-1-methyl-quinazoline-2,4-dione

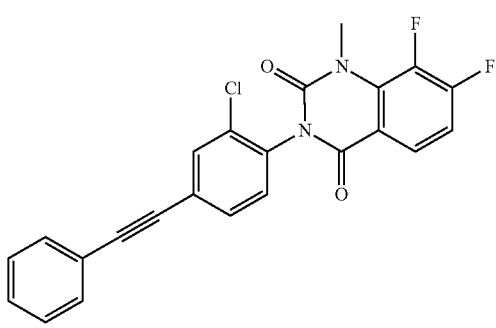 [SMILES: Cn1c(=O)n(-c2ccc(C#Cc3ccccc3)cc2Cl)c(=O)c2ccc(F)c(F)c21]

Step 1: 3-[2-Chloro-4-(2-phenylethynyl)phenyl]-7,8-difluoro-1H-quinazoline-2,4-dione The title compound was obtained as a yellow solid, MS: m/e=407.2/409.2 (M−H$^+$), using chemistry similar to that described in Example 10, step 1 from 2-chloro-4-(2-phenylethynyl)aniline (Example 4, step 1) and methyl 2-amino-3,4-difluorobenzoate.

Step 2: 3-[2-Chloro-4-(2-phenylethynyl)phenyl]-7,8-difluoro-1-methyl-quinazoline-2,4-dione The title compound was obtained as a light yellow solid, MS: m/e=423.2/425.2 (M+H$^+$), using chemistry similar to that described in Example 1, step 4 from 3-[2-chloro-4-(2-phenylethynyl)phenyl]-7,8-difluoro-H-quinazoline-2,4-dione (Example 19, step 1) and iodomethane.

Example 20

3-[2-Chloro-4-(2-phenylethynyl)phenyl]-1,7-dimethyl-thieno[3,2-d]pyrimidine-2,4-dione

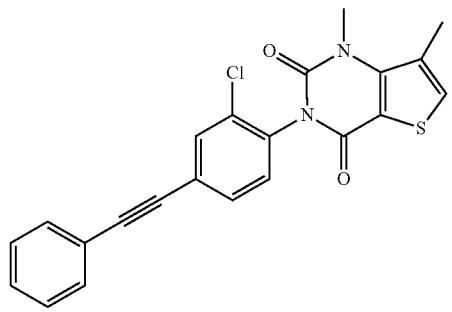 [SMILES: Cc1csc2c(=O)n(-c3ccc(C#Cc4ccccc4)cc3Cl)c(=O)n(C)c12]

Step 1: 3-(2-Chloro-4-phenylethynyl-phenyl)-7-methyl-1H-thieno[3,2-d]pyrimidine-2,4-dione The title compound was obtained as a light brown solid, MS: m/e=391.1/393.1 (M+H$^+$), using chemistry similar to that described in Example 10, step 1 from 2-chloro-4-(2-phenylethynyl)aniline (Example 4, step 1) and methyl 3-amino-4-methylthiophene-2-carboxylate.

Step 2: 3-[2-Chloro-4-(2-phenylethynyl)phenyl]-1,7-dimethyl-thieno[3,2-d]pyrimidine-2,4-dione The title compound was obtained as an off-white solid, MS: m/e=407.2/409.1 (M+H$^+$), using chemistry similar to that described in Example 1, step 4 from 3-(2-chloro-4-phenylethynyl-phenyl)-7-methyl-1H-thieno[3,2-d]pyrimidine-2,4-dione (Example 20, step 1) and iodomethane.

Example 21

3-[2-Chloro-4-(2-phenylethynyl)phenyl]-1-isopropyl-pteridine-2,4-dione

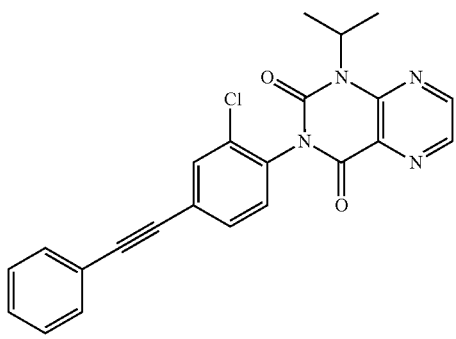

Step 1: 3-(2-Chloro-4-iodo-phenyl)-1H-pteridine-2,4-dione

The title compound was obtained as a yellow solid, MS: m/e=401.1/403.1 (M−H+), using chemistry similar to that described in Example 10, step 1 from 2-chloro-4-iodoaniline and methyl 3-aminopyrazine-2-carboxylate.

Step 2: 3-(2-Chloro-4-iodo-phenyl)-1-isopropyl-pteridine-2,4-dione

The title compound was obtained as a light yellow solid, MS: m/e=443.2/445.1 (M+H+), using chemistry similar to that described in Example 1, step 4 from 3-(2-chloro-4-iodo-phenyl)-1H-pteridine-2,4-dione (Example 21, step 1) and 2-iodopropane.

Step 3: 3-[2-Chloro-4-(2-phenylethynyl)phenyl]-1-isopropyl-pteridine-2,4-dione The title compound was obtained as a purple solid, MS: m/e=417.3/419.3 (M+H+), using chemistry similar to that described in Example 1, step 3 from 3-(2-chloro-4-iodo-phenyl)-1-isopropyl-pteridine-2,4-dione (Example 21, step 2) and phenylacetylene.

Example 22

3-[2-Chloro-4-[2-(3-pyridyl)ethynyl]phenyl]-1-isopropyl-pteridine-2,4-dione

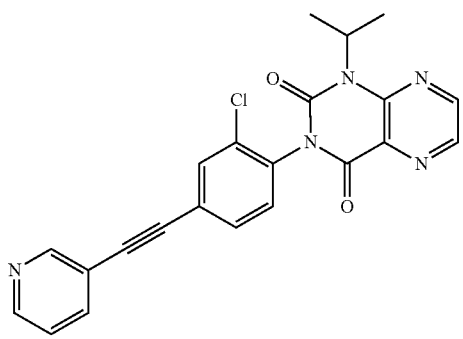 [SMILES: CC(C)n1c(=O)n(-c2ccc(C#Cc3cccnc3)cc2Cl)c(=O)c2nccnc21]

The title compound was obtained as a white solid, MS: m/e=418.3/420.3 (M+H+), using chemistry similar to that described in Example 1, step 3 from 3-(2-chloro-4-iodo-phenyl)-1-isopropyl-pteridine-2,4-dione (Example 21, step 2) and 3-ethynylpyridine.

Example 23

3-[2,6-Difluoro-4-(2-phenylethynyl)phenyl]-1-methyl-quinazoline-2,4-dione

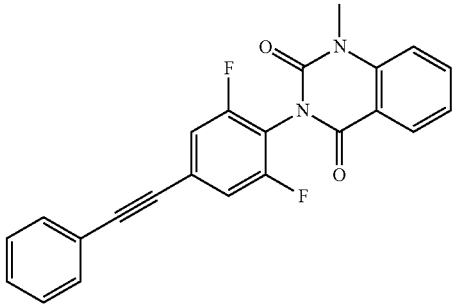 [SMILES: Cn1c(=O)n(-c2c(F)cc(C#Cc3ccccc3)cc2F)c(=O)c2ccccc21]

Step 1: 3-(2,6-Difluoro-4-iodo-phenyl)-1H-quinazoline-2,4-dione

The title compound was obtained as an off-white solid, MS: m/e=401.0 (M+H+), using chemistry similar to that described in Example 10, step 1 from 2,6-difluoro-4-iodoaniline and methyl 2-aminobenzoate.

Step 2: 3-[2,6-Difluoro-4-(2-phenylethynyl)phenyl]-1H-quinazoline-2,4-dione

The title compound was obtained as a light brown solid, MS: m/e=375.1 (M+H+), using chemistry similar to that described in Example 1, step 3 from 3-(2,6-difluoro-4-iodo-phenyl)-1H-quinazoline-2,4-dione (Example 23, step 1) and phenylacetylene.

Step 3: 3-[2,6-Difluoro-4-(2-phenylethynyl)phenyl]-1-methyl-quinazoline-2,4-dione The title compound was obtained as a light brown solid, MS: m/e=389.2 (M+H+), using chemistry similar to that described in Example 1, step 4 from 3-[2,6-difluoro-4-(2-phenylethynyl)phenyl]-1H-quinazoline-2,4-dione (Example 23, step 2) and iodomethane.

Example 24

3-[2,6-Difluoro-4-(2-phenylethynyl)phenyl]-1,8-dimethyl-quinazoline-2,4-dione

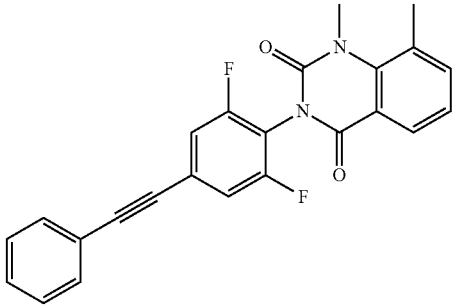 [SMILES: Cc1cccc2c(=O)n(-c3c(F)cc(C#Cc4ccccc4)cc3F)c(=O)n(C)c12]

Step 1: 3-(2,6-Difluoro-4-iodo-phenyl)-8-methyl-1H-quinazoline-2,4-dione

The title compound was obtained as an off-white solid, MS: m/e=415.1 (M+H⁺), using chemistry similar to that described in Example 10, step 1 from 2,6-difluoro-4-iodoaniline and methyl 2-amino-3-methylbenzoate.

Step 2: 3-(2,6-Difluoro-4-phenylethynyl-phenyl)-8-methyl-1H-quinazoline-2,4-dione The title compound was obtained as a light brown solid, MS: m/e=389.2 (M+H⁺), using chemistry similar to that described in Example 1, step 3 from 3-(2,6-difluoro-4-phenylethynyl-phenyl)-8-methyl-1H-quinazoline-2,4-dione (Example 24, step 1) and phenylacetylene.

Step 3: 3-[2,6-Difluoro-4-(2-phenylethynyl)phenyl]-1,8-dimethyl-quinazoline-2,4-dione The title compound was obtained as a white solid, MS: m/e=403.1 (M+H⁺), using chemistry similar to that described in Example 1, step 4 from 3-(2,6-difluoro-4-phenylethynyl-phenyl)-8-methyl-1H-quinazoline-2,4-dione (Example 24, step 2) and iodomethane.

Example 25

3-(2,6-Difluoro-4-phenylethynyl-phenyl)-1-methyl-1H-pyrido[2,3-d]pyrimidine-2,4-dione

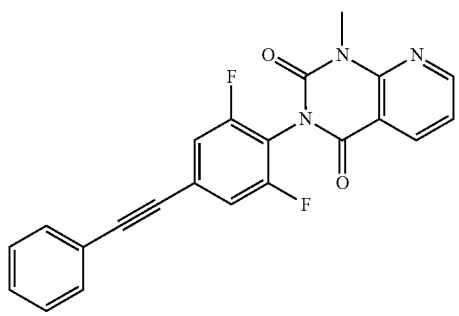 [SMILES: Cn1c(=O)n(-c2c(F)cc(C#Cc3ccccc3)cc2F)c(=O)c2cccnc21]

Step 1: 2,6-Difluoro-4-phenylethynyl-phenylamine

The title compound was obtained as a light brown solid, MS: m/e=230.1 (M+H⁺), using chemistry similar to that described in Example 1, step 3 from 2,6-difluoro-4-iodoaniline and phenylacetylene.

Step 2: 3-(2,6-Difluoro-4-phenylethynyl-phenyl)-1H-pyrido[2,3-d]pyrimidine-2,4-dione The title compound was obtained as an off-white solid, MS: m/e=376.2 (M+H⁺), using chemistry similar to that described in Example 10, step 1 from 2,6-difluoro-4-phenylethynyl-phenylamine and methyl 2-aminonicotinate.

Step 3: 3-(2,6-Difluoro-4-phenylethynyl-phenyl)-1-methyl-1H-pyrido[2,3-d]pyrimidine-2,4-dione The title compound was obtained as an off-white solid, MS: m/e=390.1 (M+H⁺), using chemistry similar to that described in Example 1, step 4 from 3-(2,6-difluoro-4-phenylethynyl-phenyl)-1H-pyrido[2,3-d]pyrimidine-2,4-dione (Example 25, step 2) and iodomethane.

Example 26

3-[2,6-Difluoro-4-(2-phenylethynyl)phenyl]-1,7-dimethyl-quinazoline-2,4-dione

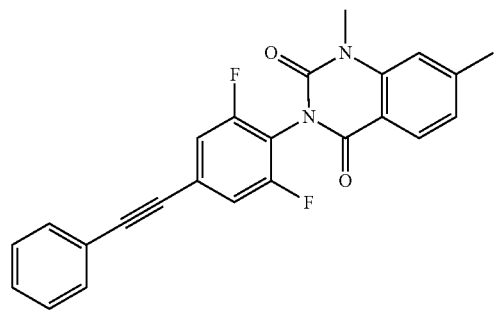 [SMILES: Cc1ccc2c(=O)n(-c3c(F)cc(C#Cc4ccccc4)cc3F)c(=O)n(C)c2c1]

Step 1: 3-(2,6-Difluoro-4-phenylethynyl-phenyl)-7-methyl-1H-quinazoline-2,4-dione The title compound was obtained as an off-white solid, MS: m/e=389.1 (M+H⁺), using chemistry similar to that described in Example 10, step 1 from 2,6-difluoro-4-phenylethynyl-phenylamine (Example 25, step 1) and methyl 2-amino-4-methylbenzoate.

Step 2: 3-[2,6-Difluoro-4-(2-phenylethynyl)phenyl]-1,7-dimethyl-quinazoline-2,4-dione The title compound was obtained as an off-white solid, MS: m/e=403.2 (M+H⁺), using chemistry similar to that described in Example 1, step 4 from 3-(2,6-difluoro-4-phenylethynyl-phenyl)-7-methyl-1H-quinazoline-2,4-dione (Example 26, step 1) and iodomethane.

Example 27

3-[2,6-Difluoro-4-(2-phenylethynyl)phenyl]-1,7-dimethyl-thieno[3,2-d]pyrimidine-2,4-dione

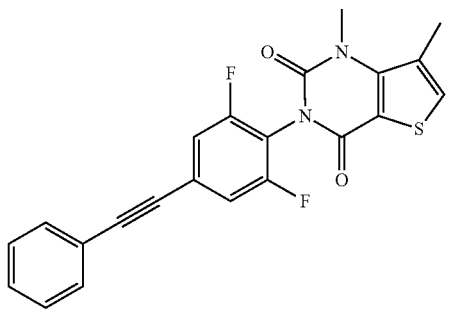 [SMILES: Cc1csc2c(=O)n(-c3c(F)cc(C#Cc4ccccc4)cc3F)c(=O)n(C)c12]

Step 1: 3-(2,6-Difluoro-4-phenylethynyl-phenyl)-7-methyl-1H-thieno[3,2-d]pyrimidine-2,4-dione The title compound was obtained as an off-white solid, MS: m/e=395.0 (M+H⁺), using chemistry similar to that described in Example 10, step 1 from 2,6-difluoro-4-phenylethynyl-phenylamine (Example 25, step 1) and methyl 3-amino-4-methylthiophene-2-carboxylate.

Step 2: 3-[2,6-Difluoro-4-(2-phenylethynyl)phenyl]-1,7-dimethyl-thieno[3,2-d]pyrimidine-2,4-dione The title compound was obtained as an off-white solid, MS: m/e=409.2 (M+H⁺), using chemistry similar to that described in Example 1, step 4 from 3-(2,6-difluoro-4-phenylethynyl-phenyl)-7-methyl-1H-thieno[3,2-d]pyrimidine-2,4-dione (Example 27, step 1) and iodomethane.

Example 28

3-[2,6-Difluoro-4-[2-(3-pyridyl)ethynyl]phenyl]-1,7-dimethyl-thieno[3,2-d]pyrimidine-2,4-dione

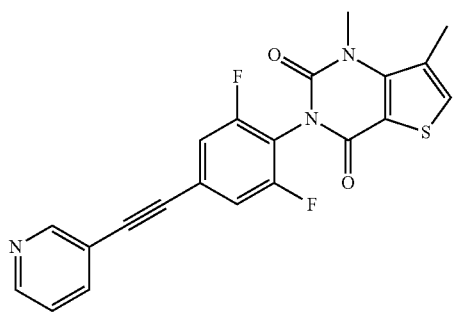 [SMILES: Cc1csc2c(=O)n(-c3c(F)cc(C#Cc4cccnc4)cc3F)c(=O)n(C)c12]

Step 1: 2,6-Difluoro-4-pyridin-3-ylethynyl-phenylamine

The title compound was obtained as a light brown solid, MS: m/e=231.1 (M+H⁺), using chemistry similar to that described in Example 1, step 3 from 2,6-difluoro-4-iodoaniline and 3-ethynylpyridine.

Step 2: 3-(2,6-Difluoro-4-pyridin-3-ylethynyl-phenyl)-7-methyl-1H-thieno[3,2-d]pyrimidine-2,4-dione The title compound was obtained as an off-white solid, MS: m/e=396.2 (M+H⁺), using chemistry similar to that described in Example 10, step 1 from 2,6-difluoro-4-pyridin-3-ylethynyl-phenylamine (Example 28, step 1) and methyl 3-amino-4-methylthiophene-2-carboxylate.

Step 3: 3-[2,6-Difluoro-4-[2-(3-pyridyl)ethynyl]phenyl]-1,7-dimethyl-thieno[3,2d]pyrimidine-2,4-dione The title compound was obtained as an off-white solid, MS: m/e=410.2 (M+H⁺), using chemistry similar to that described in Example 1, step 4 from 3-(2,6-difluoro-4-pyridin-3-ylethynyl-phenyl)-7-methyl-1H-thieno[3,2-d]pyrimidine-2,4-dione (Example 28, step 2) and iodomethane.

Example 29

2-(2,6-Difluoro-4-(phenylethynyl)phenyl)-5,6-dihydro-1H-pyrrolo[3,2,1-ij]quinazoline-1,3(2H)-dione

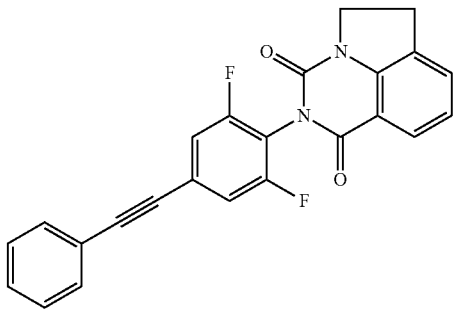 [SMILES: O=c1c2cccc3c2n(c(=O)n1-c1c(F)cc(C#Cc2ccccc2)cc1F)CC3]

The title compound was obtained as an off-white solid, MS: m/e=401.2 (M+H⁺), using chemistry similar to that described in Example 10, step 1 from 2,6-difluoro-4-phenylethynyl-phenylamine (Example 25, step 1) and methyl indoline-7-carboxylate.

Example 30

2-(2,6-Difluoro-4-(pyridin-3-ylethynyl)phenyl)-5,6-dihydro-1H-pyrrolo[3,2,1-ij]quinazoline-1,3(2H)-dione

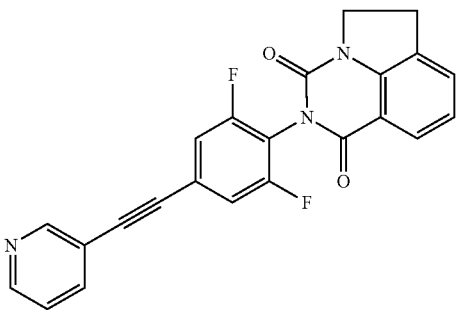 [SMILES: O=c1c2cccc3c2n(c(=O)n1-c1c(F)cc(C#Cc2cccnc2)cc1F)CC3]

The title compound was obtained as an off-white solid, MS: m/e=402.2 (M+H⁺), using chemistry similar to that described in Example 10, step 1 from 2,6-difluoro-4-pyridin-3-ylethynyl-phenylamine (Example 28, step 1) and methyl indoline-7-carboxylate.

Example 31

6-[2,6-Difluoro-4-(2-phenylethynyl)phenyl]-4H-thiazolo[4,5-d]pyrimidine-5,7-dione

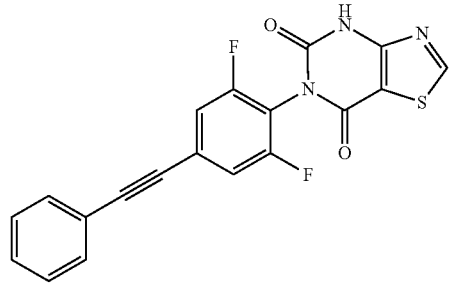 [SMILES: O=c1[nH]c2ncsc2c(=O)n1-c1c(F)cc(C#Cc2ccccc2)cc1F]

The title compound was obtained as an off-white solid, MS: m/e=380.1 (M+H⁺), using chemistry similar to that described in Example 10, step 1 from 2,6-difluoro-4-phenylethynyl-phenylamine (Example 25, step 1) and methyl 4-aminothiazole-5-carboxylate.

Example 32

6-[2,6-Difluoro-4-(2-phenylethynyl)phenyl]-4-methyl-thiazolo[4,5-d]pyrimidine-5,7-dione

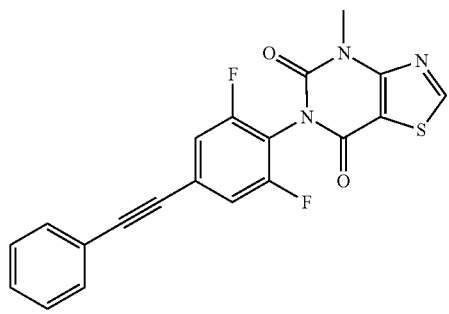 [SMILES: Cn1c(=O)n(-c2c(F)cc(C#Cc3ccccc3)cc2F)c(=O)c2scnc21]

The title compound was obtained as a white solid, MS: m/e=396.2 (M+H⁺), using chemistry similar to that described in Example 1, step 4 from 6-[2,6-difluoro-4-(2 phenylethynyl)-phenyl]-4H-thiazolo[4,5-d]pyrimidine-5,7-dione (Example 31) and iodomethane.

Example 33

6-[2,6-Difluoro-4-(2-phenylethynyl)phenyl]-2,4-dimethyl-pyrazolo[4,3-d]pyrimidine-5,7-dione

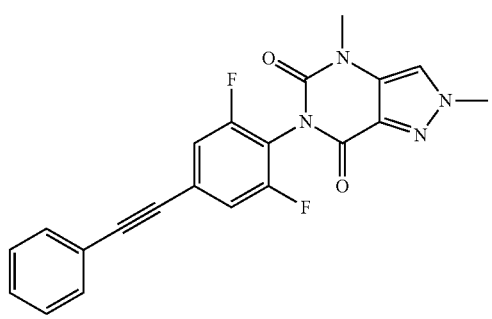 [SMILES: Cn1cc2c(n1)c(=O)n(-c1c(F)cc(C#Cc3ccccc3)cc1F)c(=O)n2C]

Step 1: Methyl 4-[[2,6-difluoro-4-(2-phenylethynyl) phenyl]carbamolamino]-1-methyl-pyrazole-3-carboxylate 2,6-Difluoro-4-phenylethynyl-phenylamine (Example 25, step 1) (200 mg, 0.87 mmol) was dissolved in toluene (6.0 ml) and bis(trichloromethyl) carbonate (104 mg, 0.35 mmol, 0.4 equiv.) was added at room temperature. The mixture was stirred for 1 hour at 110° C. The mixture was cooled to room temperature and Et₃N (440 mg, 0.61 ml, 4.36 mmol, 5 equiv.) and methyl 4-amino-1-methyl-1H-pyrazole-3-carboxylate (135 mg, 0.87 mmol, 1.0 equiv.) were added at room temperature. The mixture was stirred for 16 hours at 110° C. The reaction mixture was loaded directly onto a silica gel column. The crude product was purified by flash chromatography eluting with an ethyl acetate:heptane gradient 5:95 to 100:0. The desired methyl 4-[[2,6-difluoro-4-(2-phenylethynyl)phenyl]carbamoylamino]-1-methyl-pyrazole-3-carboxylate (223 mg, 65% yield) was obtained as a light yellow solid, MS: m/e=409.4 (M+H⁺).

Step 2: 6-[2,6-Difluoro-4-(2-phenylethynyl)phenyl]-2-methyl-4H-pyrazolo[4,3-d]pyrimidine-5,7-dione The title compound was obtained as a white solid, MS: m/e=377.3 (M–H⁺), using chemistry similar to that described in Example 11, step 2 from methyl 4-[[2,6-difluoro-4-(2-phenylethynyl)phenyl]carbamoylamino]-1-methyl-pyrazole-3-carboxylate (Example 33, step 1).

Step 3: 6-[2,6-Difluoro-4-(2-phenylethynyl)phenyl]-2,4-dimethyl-pyrazolo[4,3-d]pyrimidine-5,7-dione The title compound was obtained as a yellow solid, MS: m/e=393.2 (M+H⁺), using chemistry similar to that described in Example 1, step 4 from 6-[2,6-difluoro-4-(2-phenylethynyl)phenyl]-2-methyl-4H-pyrazolo[4,3-d]pyrimidine-5,7-dione (Example 33, step 2) and iodomethane.

Example 34

6-[2,6-Difluoro-4-(2-phenylethynyl)phenyl]-1,4-dimethyl-pyrazolo[4,3-d]pyrimidine-5,7-dione

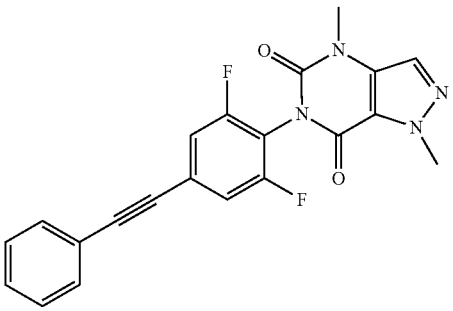 [SMILES: Cn1ncc2c1c(=O)n(-c1c(F)cc(C#Cc3ccccc3)cc1F)c(=O)n2C]

Step 1: 6-[2,6-Difluoro-4-(2-phenylethynyl)phenyl]-1-methyl-4H-pyrazolo[4,3-d]pyrimidine-5,7-dione The title compound was obtained as a white solid, MS: m/e=379.2 (M+H⁺), using chemistry similar to that described in Example 33, step 1 and step 2 starting from 2,6-difluoro-4-phenylethynyl-phenylamine (Example 25, step 1) and methyl 4-amino-1-methyl-1H-pyrazole-5-carboxylate.

Step 2: 6-[2,6-Difluoro-4-(2-phenylethynyl)phenyl]-1,4-dimethyl-pyrazolo[4,3-d]pyrimidine-5,7-dione The title compound was obtained as a white solid, MS: m/e=393.3 (M+H$^+$), using chemistry similar to that described in Example 1, step 4 from 6-[2,6-difluoro-4-(2-phenylethynyl)phenyl]-1-methyl-4H-pyrazolo[4,3-d]pyrimidine-5,7-dione (Example 34, step 1) and iodomethane.

Example 35

6-[2,6-Difluoro-4-(2-phenylethynyl)phenyl]-4-isopropyl-2-methyl-pyrazolo[4,3-d]pyrimidine-5,7-dione

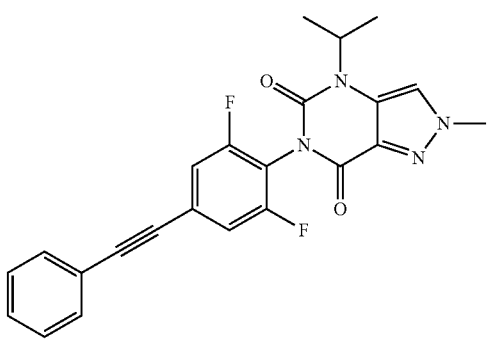 [SMILES: CC(C)n1c(=O)n(-c2c(F)cc(C#Cc3ccccc3)cc2F)c(=O)c2nn(C)cc21]

The title compound was obtained as a white solid, MS: m/e=421.3 (M+H$^+$), using chemistry similar to that described in Example 1, step 4 from 6-[2,6-difluoro-4-(2-phenylethynyl)phenyl]-2-methyl-4H-pyrazolo[4,3-d]pyrimidine-5,7-dione (Example 33, step 2) and 2-iodopropane.

Example 36

6-[2,6-Difluoro-4-(2-phenylethynyl)phenyl]-4-isopropyl-1-methyl-pyrazolo[4,3-d]pyrimidine-5,7-dione

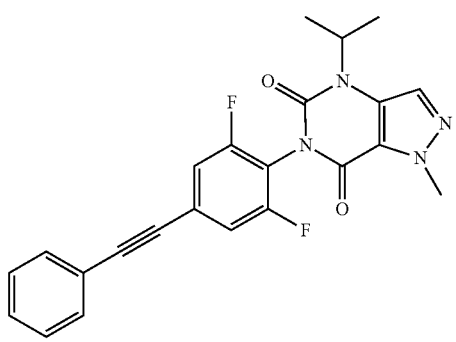 [SMILES: CC(C)n1c(=O)n(-c2c(F)cc(C#Cc3ccccc3)cc2F)c(=O)c2c1cnn2C]

The title compound was obtained as a yellow solid, MS: m/e=421.3 (M+H$^+$), using chemistry similar to that described in Example 1, step 4 from 6-[2,6-difluoro-4-(2-phenylethynyl)phenyl]-1-methyl-4H-pyrazolo[4,3-d]pyrimidine-5,7-dione (Example 34, step 1) and 2-iodopropane.

Example 37

3-[2,6-Difluoro-4-(2-phenylethynyl)phenyl]-1-isopropyl-pyrido[2,3-d]pyrimidine-2,4-dione

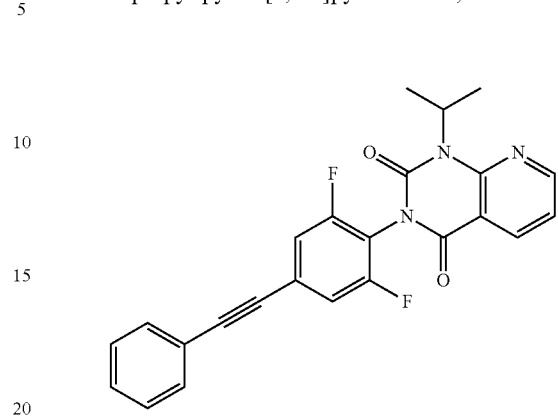

The title compound was obtained as a white solid, MS: m/e=418.3 (M+H$^+$), using chemistry similar to that described in Example 1, step 4 from 3-(2,6-difluoro-4-phenylethynyl-phenyl)-1H-pyrido[2,3-d]pyrimidine-2,4-dione (Example 25, step 2) and 2-iodopropane.

Example 38

3-[2,6-Difluoro-4-(2-phenylethynyl)phenyl]-1,8-dimethyl-pyrido[3,2-d]pyrimidine-2,4-dione

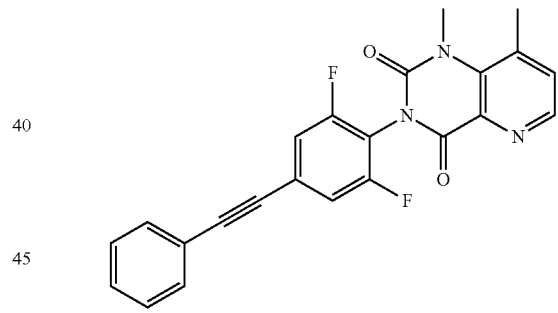

Step 1: 3-[2,6-Difluoro-4-(2-phenylethynyl)phenyl]-8-methyl-1H-pyrido[3,2-d]pyrimidine-2,4-dione The title compound was obtained as a yellow solid, MS: m/e=388.3 (M+H$^+$), using chemistry similar to that described in Example 10, step 1 from 2,6-difluoro-4-phenylethynyl-phenylamine (Example 25, step 1) and 3-amino-4-methylpicolinic acid.

Step 2: 3-[2,6-Difluoro-4-(2-phenylethynyl)phenyl]-1,8-dimethyl-pyrido[3,2-d]pyrimidine-2,4-dione The title compound was obtained as a light yellow solid, MS: m/e=404.2 (M+H$^+$), using chemistry similar to that described in Example 1, step 4 from 3-[2,6-difluoro-4-(2-phenylethynyl)phenyl]-8-methyl-1H-pyrido[3,2-d]pyrimidine-2,4-dione (Example 38, step 1) and iodomethane.

Example 39

6-[2,6-Difluoro-4-(2-phenylethynyl)phenyl]-4-methyl-[1,2,5]thiadiazolo[3,4-d]pyrimidine-5,7-dione

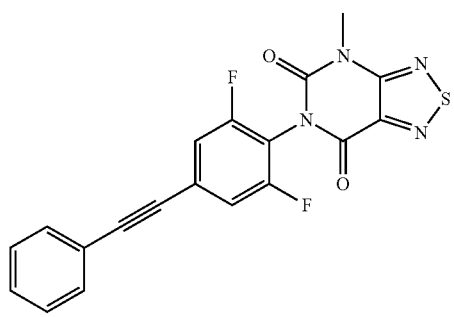 [SMILES: Cn1c(=O)n(-c2c(F)cc(C#Cc3ccccc3)cc2F)c(=O)c2nsnc21]

Step 1: 6-[2,6-difluoro-4-(2-phenylethynyl)phenyl]-4H-[1,2,5]thiadiazolo[3,4-d]pyrimidine-5,7-dione The title compound was obtained as a yellow solid, MS: m/e=381.2 (M+H$^+$), using chemistry similar to that described in Example 10, step 1 from 2,6-difluoro-4-phenylethynyl-phenylamine (Example 25, step 1) and 4-amino-1,2,5-thiadiazole-3-carboxylic acid.

Step 2: 6-[2,6-Difluoro-4-(2-phenylethynyl)phenyl]-4-methyl-[1,2,5]thiadiazolo[3,4-d]pyrimidine-5,7-dione The title compound was obtained as a white solid, MS: m/e=397.2 (M+H$^+$), using chemistry similar to that described in Example 1, step 4 from 6-[2,6-difluoro-4-(2-phenylethynyl)phenyl]-4-H-[1,2,5]thiadiazolo[3,4-d]pyrimidine-5,7-dione (Example 39, step 1) and iodomethane.

Example 40

6-[2,6-Difluoro-4-(2-phenylethynyl)phenyl]-4-isopropyl-[1,2,5]thiadiazolo[3,4-d]pyrimidine-5,7-dione

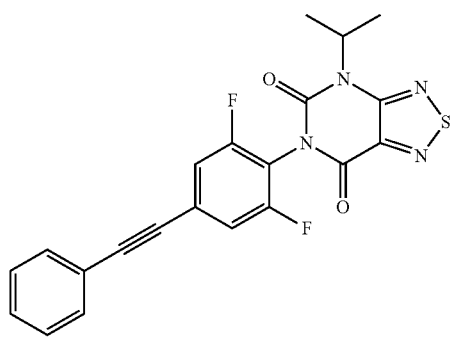 [SMILES: CC(C)n1c(=O)n(-c2c(F)cc(C#Cc3ccccc3)cc2F)c(=O)c2nsnc21]

The title compound was obtained as a white solid, MS: m/e=425.2 (M+H$^+$), using chemistry similar to that described in Example 1, step 4 from 6-[2,6-difluoro-4-(2-phenylethynyl)phenyl]-4-H-[1,2,5]thiadiazolo[3,4-d]pyrimidine-5,7-dione (Example 39, step 1) and 2-iodopropane.

Example 41

3-[2-Chloro-4-(2-phenylethynyl)phenyl]-1,5-dimethyl-quinazoline-2,4-dione

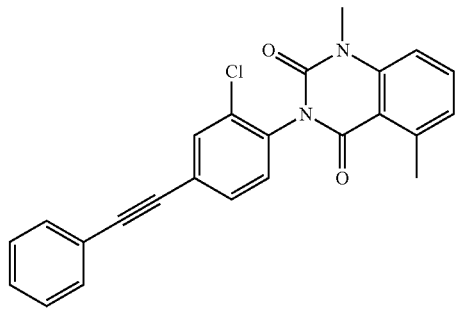 [SMILES: Cc1cccc2c1c(=O)n(-c1ccc(C#Cc3ccccc3)cc1Cl)c(=O)n2C]

Step 1: 3-[2-Chloro-4-(2-phenylethynyl)phenyl]-5-methyl-1H-quinazoline-2,4-dione The title compound was obtained as a yellow solid, MS: m/e=387.1/389.2 (M+H$^+$), using chemistry similar to that described in Example 10, step 1 from 2-chloro-4-(2-phenylethynyl)aniline (Example 4, step 1) and methyl 2-amino-6-methylbenzoate.

Step 2: 3-[2-Chloro-4-(2-phenylethynyl)phenyl]-1,5-dimethyl-quinazoline-2,4-dione The title compound was obtained as a light yellow solid, MS: m/e=401.2/403.2 (M+H$^+$), using chemistry similar to that described in Example 1, step 4 from 3-[2-chloro-4-(2-phenylethynyl)phenyl]-5-methyl-1H-quinazoline-2,4-dione (Example 41, step 1) and iodomethane.

Example 42

3-[2-Chloro-6-fluoro-4-[2-(3-pyridyl)ethynyl]phenyl]-1-isopropyl-quinazoline-2,4-dione

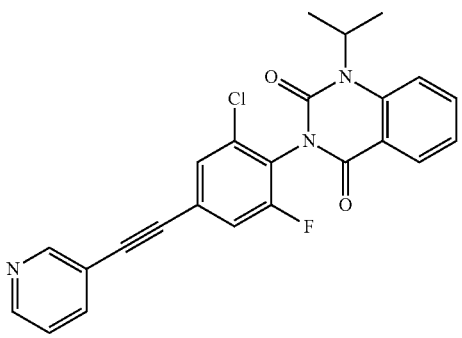 [SMILES: CC(C)n1c(=O)n(-c2c(F)cc(C#Cc3cccnc3)cc2Cl)c(=O)c2ccccc21]

Step 1: 2-Chloro-6-fluoro-4-[2-(3-pyridyl)ethynyl]aniline

The title compound was obtained as an orange solid, MS: m/e=247.1/249.1 (M+H$^+$), using chemistry similar to that described in Example 1, step 3 from 2,6-difluoro-4-iodoaniline and 3-ethynylpyridine.

Step 2: Methyl 2-(isopropylamino)benzoate

Methyl 2-aminobenzoate (2 g, 13.2 mmol) was dissolved in dichloromethane (6.0 ml) and trifluoroacetic acid (2.0 ml, 26.5 mmol, 2.0 equiv.), acetone (2.91 ml, 39.7 mmol, 3 equiv.) and tetramethylammonium triacetoxyborohydride (5.22 g, 19.8 mmol, 1.5 equiv.) were added at room temperature. The mixture was stirred for 16 hour at room temperature. The reaction mixture was extracted with saturated NaHCO$_3$ solution and twice with dichloromethane. The organic layers were combined and evaporated to dryness. The crude product was purified by flash chromatography on a silica gel column eluting with an ethyl acetate: heptane gradient 0:100 to 20:80. The desired methyl 2-(isopropylamino)benzoate (2.43 g, 90% yield) was obtained as a colorless oil, MS: m/e=194.2 (M+H$^+$).

Step 3: 3-[2-Chloro-6-fluoro-4-[2-(3-pyridyl)ethynyl]phenyl]-1-isopropyl-quinazoline-2,4-dione The title compound was obtained as a white solid, MS: m/e=434.3 (M+H$^+$), using chemistry similar to that described in Example 10, step 1 from 2-chloro-6-fluoro-4-[2-(3-pyridyl)ethynyl]aniline (Example 42, step 1) and methyl 2-(isopropylamino)benzoate (Example 42, step 2).

Example 43

3-[2-Chloro-6-fluoro-4-[2-(3-pyridyl)ethynyl]phenyl]-1,8-dimethyl-quinazoline-2,4-dione

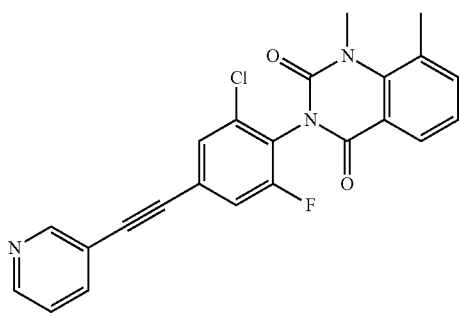

Step 1: 3-[2-Chloro-6-fluoro-4-[2-(3-pyridyl)ethynyl]phenyl]-8-methyl-1H-quinazoline-2,4-dione The title compound was obtained as a white solid, MS: m/e=406.2/408.2 (M+H$^+$), using chemistry similar to that described in Example 10, step 1 from 2-chloro-6-fluoro-4-[2-(3-pyridyl)ethynyl]aniline (Example 42, step 1) and methyl 2-amino-3-methylbenzoate.

Step 2: 3-[2-Chloro-6-fluoro-4-[2-(3-pyridyl)ethynyl]phenyl]-1,8-dimethyl-quinazoline-2,4-dione The title compound was obtained as a light yellow solid, MS: m/e=420.2/422.2 (M+H$^+$), using chemistry similar to that described in Example 1, step 4 from 3-[2-chloro-6-fluoro-4-[2-(3-pyridyl)ethynyl]phenyl]-8-methyl-1H-quinazoline-2,4-dione (Example 43, step 1) and iodomethane.

Example 44

3-[3-Chloro-5-(2-phenylethynyl)-2-pyridyl]-1-methyl-quinazoline-2,4-dione

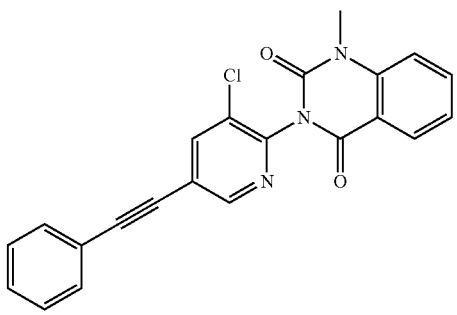 [SMILES: Cn1c(=O)n(-c2ncc(C#Cc3ccccc3)cc2Cl)c(=O)c2ccccc21]

Step 1: 3-Chloro-5-(2-phenylethynyl)pyridin-2-amine

The title compound was obtained as a yellow solid, MS: m/e=229.1/231.1 (M+H$^+$), using chemistry similar to that described in Example 1, step 3 from 5-bromo-3-chloropyridin-2-amine and phenylacetylene.

Step 2: 3-[3-Chloro-5-(2-phenylethynyl)-2-pyridyl]-1H-quinazoline-2,4-dione

The title compound was obtained as a white solid, MS: m/e=374.2/376.2 (M+H$^+$), using chemistry similar to that described in Example 10, step 1 from 3-chloro-5-(2-phenylethynyl)pyridin-2-amine (Example 44, step 1) and methyl 2-aminobenzoate.

Step 3: 3-[3-Chloro-5-(2-phenylethynyl)-2-pyridyl]-1-methyl-quinazoline-2,4-dione The title compound was obtained as a light yellow solid, MS: m/e=388.2/390.3 (M+H$^+$), using chemistry similar to that described in Example 1, step 4 from 3-[3-chloro-5-(2-phenylethynyl)-2-pyridyl]-1H-quinazoline-2,4-dione (Example 44, step 1) and iodomethane.

Example 45

3-[3-Chloro-5-(2-phenylethynyl)-2-pyridyl]-1-isopropyl-quinazoline-2,4-dione

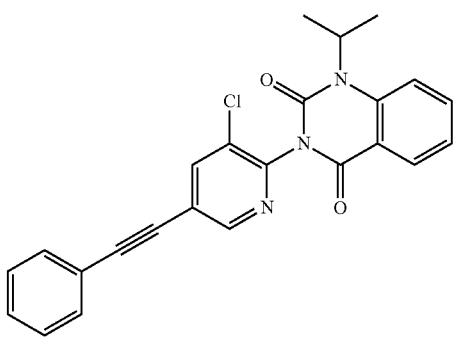

The title compound was obtained as a white solid, MS: m/e=416.3/418.3 (M+H⁺), using chemistry similar to that described in Example 10, step 1 from 3-chloro-5-(2-phenylethynyl)pyridin-2-amine (Example 44, step 1) and 2-(isopropylamino)benzoate (Example 42, step 2).

Example 46

3-[3-Chloro-5-(2-phenylethynyl)-2-pyridyl]-1,8-dimethyl-quinazoline-2,4-dione

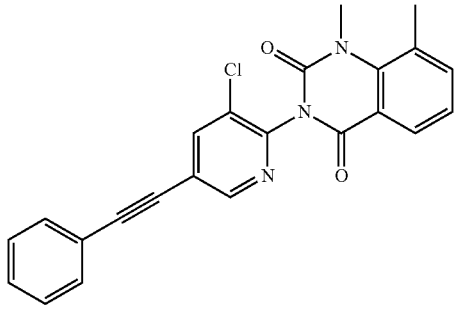

Step 1: 3-[3-Chloro-5-(2-phenylethynyl)-2-pyridyl]-8-methyl-1H-quinazoline-2,4-dione The title compound was obtained as a light yellow solid, MS: m/e=388.3/390.3 (M+H⁺), using chemistry similar to that described in Example 10, step 1 from 3-chloro-5-(2-phenylethynyl)pyridin-2-amine (Example 44, step 1) and methyl 2-amino-3-methylbenzoate.

Step 3: 3-[3-Chloro-5-(2-phenylethynyl)-2-pyridyl]-1,8-dimethyl-quinazoline-2,4-dione The title compound was obtained as a light yellow solid, MS: m/e=402.2/404.2 (M+H⁺), using chemistry similar to that described in Example 1, step 4 from 3-[3-chloro-5-(2-phenylethynyl)-2-pyridyl]-8-methyl-1H-quinazoline-2,4-dione (Example 46, step 1) and iodomethane.

Example 47

2-(3-Chloro-5-(phenylethynyl)pyridin-2-yl)-5,6-dihydro-1H-pyrrolo[3,2,1-ij]quinazoline-1,3(2H)-dione

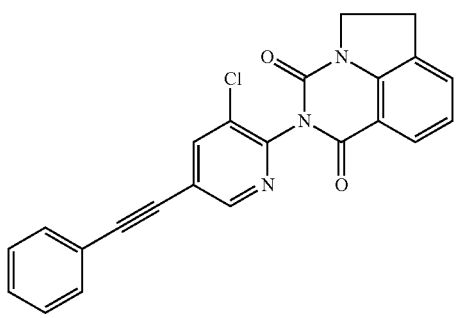

Example 48

1-Methyl-3-[5-(2-phenylethynyl)-3-(trifluoromethyl)-2-pyridyl]quinazoline-2,4-dione

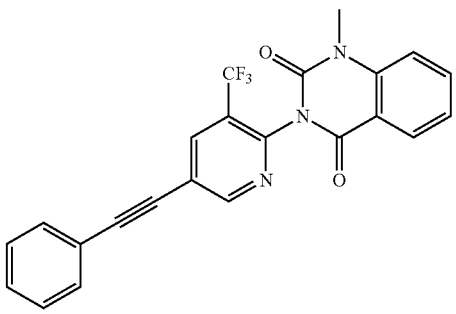

Step 1: 3-[5-Bromo-3-(trifluoromethyl)-2-pyridyl]-1H-quinazoline-2,4-dione

The title compound was obtained as a white solid, MS: m/e=386.1/388.1 (M−H⁺), using chemistry similar to that described in Example 10, step 1 from 5-bromo-3-(trifluoromethyl)pyridin-2-amine and methyl 2-aminobenzoate.

Step 2: 3-[5-(2-Phenylethynyl)-3-(trifluoromethyl)-2-pyridyl]-1H-quinazoline-2,4-dione The title compound was obtained as a light yellow solid, MS: m/e=408.2 (M+H⁺), using chemistry similar to that described in Example 1, step 3 from 3-[5-bromo-3-(trifluoromethyl)-2-pyridyl]-1H-quinazoline-2,4-dione (Example 48, step 1) and phenylacetylene.

Step 2: 1-Methyl-3-[5-(2-phenylethynyl)-3-(trifluoromethyl)-2-pyridyl]quinazoline-2,4-dione The title compound was obtained as a white solid, MS: m/e=422.3 (M+H⁺), using chemistry similar to that described in Example 1, step 4 from 3-[5-(2-phenylethynyl)-3-(trifluoromethyl)-2-pyridyl]-1H-quinazoline-2,4-dione (Example 48, step 2) and iodomethane.

Example 49

3-[3-Fluoro-5-(2-phenylethynyl)-2-pyridyl]-1,8-dimethyl-quinazoline-2,4-dione

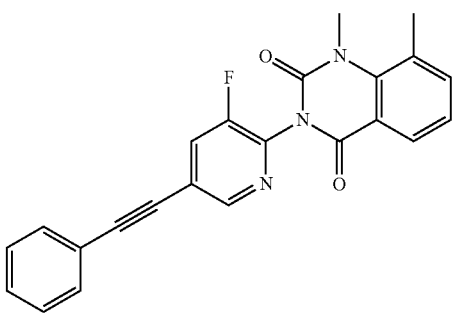 [SMILES: Cc1cccc2c(=O)n(-c3ncc(C#Cc4ccccc4)cc3F)c(=O)n(C)c12]

Step 1: 3-Fluoro-5-(2-phenylethynyl)pyridin-2-amine

The title compound was obtained as a brown solid, MS: m/e=213.2 (M+H⁺), using chemistry similar to that described in Example 1, step 3 from 5-bromo-3-fluoropyridin-2-amine and phenylacetylene.

Step 2: 3-[3-Fluoro-5-(2-phenylethynyl)-2-pyridyl]-8-methyl-1H-quinazoline-2,4-dione The title compound was obtained as a light yellow solid, MS: m/e=372.2 (M+H⁺), using chemistry similar to that described in Example 10, step 1 from 3-fluoro-5-(2-phenylethynyl)pyridin-2-amine (Example 49, step 1) and methyl 2-amino-3-methylbenzoate.

Step 3: 3-[3-Fluoro-5-(2-phenylethynyl)-2-pyridyl]-1,8-dimethyl-quinazoline-2,4-dione The title compound was obtained as a colorless oil, MS: m/e=386.2 (M+H⁺), using chemistry similar to that described in Example 1, step 4 from 3-[3-fluoro-5-(2-phenylethynyl)-2-pyridyl]-8-methyl-1H-quinazoline-2,4-dione (Example 49, step 1) and iodomethane.

Example 50

3-[2-Chloro-4-(2-phenylethynyl)phenyl]-1-(2-methoxyethyl)quinazoline-2,4-dione

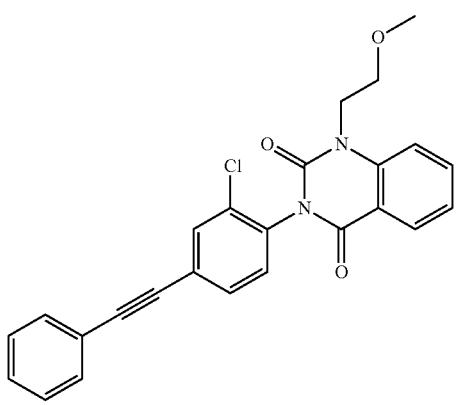 [SMILES: COCCn1c(=O)n(-c2ccc(C#Cc3ccccc3)cc2Cl)c(=O)c2ccccc21]

The title compound was obtained as a yellow solid, MS: m/e=431.2/433.1 (M+H⁺), using chemistry similar to that described in Example 1, step 4 from 3-[2-chloro-4-(2-phenylethynyl)phenyl]-1H-quinazoline-2,4-dione (Example 1, step 3) and 1-bromo-2-methoxyethane.

Example 51

6-[2-Chloro-4-(2-phenylethynyl)phenyl]-4-methyl-2-morpholino-thiazolo[4,5-d]pyrimidine-5,7-dione

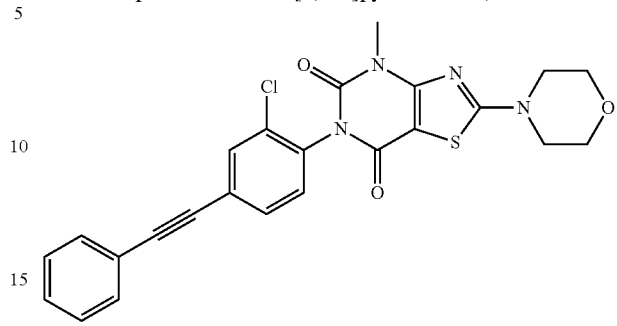

Step 1: Methyl 4-[[2-chloro-4-(2-phenylethynyl)phenyl]carbamoylamino]-2-morpholino-thiazole-5-carboxylate The title compound was obtained as a yellow solid, MS: m/e=497.3/499.3 (M−H⁺), using chemistry similar to that described in Example 10, step 1 from 2-chloro-4-(2-phenylethynyl)aniline (Example 4, step 1) and methyl 4-amino-2-morpholinothiazole-5-carboxylate.

Step 2: 6-[2-Chloro-4-(2-phenylethynyl)phenyl]-2-morpholino-4H-thiazolo[4,5-d]pyrimidine-5,7-dione The title compound was obtained as a light yellow solid, MS: m/e=463.3/465.3 (M+H⁺), using chemistry similar to that described in Example 11, step 2 from methyl 4-[[2-chloro-4-(2-phenylethynyl)phenyl]carbamoylamino]-2-morpholino-thiazole-5-carboxylate (Example 51, step 1).

Step 3: 6-[2-Chloro-4-(2-phenylethynyl)phenyl]-4-methyl-2-morpholino-thiazolo[4,5-d]pyrimidine-5,7-dione The title compound was obtained as a white solid, MS: m/e=479.2/481.2 (M+H⁺), using chemistry similar to that described in Example 1, step 4 from 6-[2-chloro-4-(2-phenylethynyl)phenyl]-2-morpholino-4H-thiazolo[4,5-d]pyrimidine-5,7-dione (Example 51, step 2) and iodomethane.

Example 52

6-(2-Chloro-4-phenylethynyl-phenyl)-4-methyl-4H-thiazolo[4,5-d]pyrimidine-5,7-dione

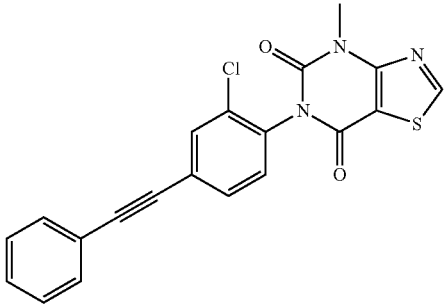 [SMILES: Cn1c(=O)n(-c2ccc(C#Cc3ccccc3)cc2Cl)c(=O)c2scnc21]

Step 1: 6-(2-Chloro-4-phenylethynyl-phenyl)-4H-thiazolo[4,5-d]pyrimidine-5,7-dione The title compound was obtained as a light yellow solid, MS: m/e=378.2/380.2 (M+H$^+$), using chemistry similar to that described in Example 10, step 1 from 2-chloro-4-(phenylethynyl)-aniline (Example 4, step 1) and methyl 4-aminothiazole-5-carboxylate.

Step 2: 6-(2-Chloro-4-phenylethynyl-phenyl)-4-methyl-4H-thiazolo[4,5-d]pyrimidine-5,7-dione The title compound was obtained as an off-white solid, MS: m/e=394.1/396.1 (M+H$^+$), using chemistry similar to that described in Example 1, step 4 from 6-(2-chloro-4-phenylethynyl-phenyl)-4H-thiazolo[4,5-d]pyrimidine-5,7-dione (Example 52, step 1) and iodomethane.

Example 53

3-[2-Chloro-4-(2-phenylethynyl)phenyl]-1-cyclobutyl-quinazoline-2,4-dione

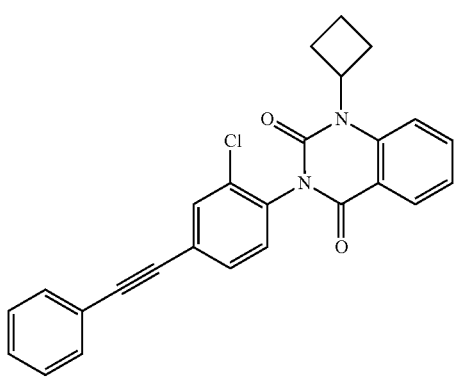 [SMILES: O=c1c2ccccc2n(C2CCC2)c(=O)n1-c1ccc(C#Cc2ccccc2)cc1Cl]

The title compound was obtained as a white foam, MS: m/e=427.2/429.2 (M+H$^+$), using chemistry similar to that described in Example 10, step 1 from 2-chloro-4-(2-phenylethynyl)aniline (Example 4, step 1) and methyl 2-(cyclobutylamino)benzoate.

Example 54

3-[2-Chloro-4-(2-phenylethynyl)phenyl]-8-isopropyl-1-methyl-quinazoline-2,4-dione

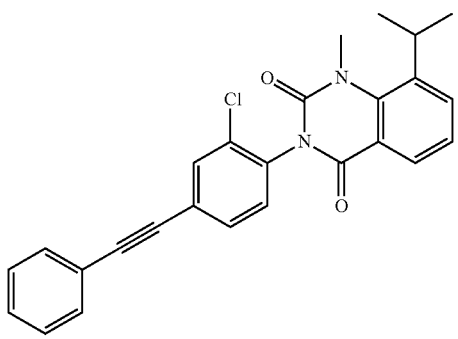

Step 1: 3-[2-Chloro-4-(2-phenylethynyl)phenyl]-8-isopropyl-1H-quinazoline-2,4-dione The title compound was obtained as a yellow solid, MS: m/e=415.2/417.1 (M+H$^+$), using chemistry similar to that described in Example 10, step 1 from 2-chloro-4-(2-phenylethynyl)aniline (Example 4, step 1) and methyl 2-amino-3-isopropylbenzoate.

Step 2: 3-[2-Chloro-4-(2-phenylethynyl)phenyl]-8-isopropyl-1-methyl-quinazoline-2,4-dione The title compound was obtained as a light yellow solid, MS: m/e=429.2/431.2 (M+H$^+$), using chemistry similar to that described in Example 1, step 4 from 3-[2-chloro-4-(2-phenylethynyl)phenyl]-8-isopropyl-1H-quinazoline-2,4-dione (Example 54, step 1) and iodomethane.

Example 55

1-Isopropyl-3-[5-(2-phenylethynyl)-2-pyridyl]quinazoline-2,4-dione

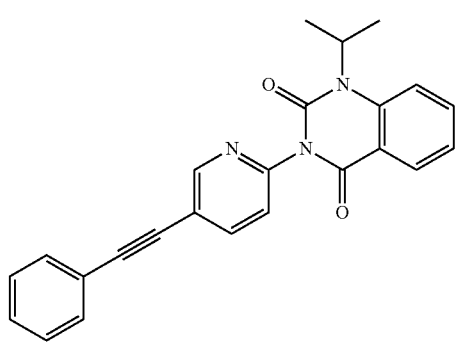 [SMILES: CC(C)n1c(=O)n(-c2ccc(C#Cc3ccccc3)cn2)c(=O)c2ccccc21]

Step 1: 3-(5-Bromo-2-pyridyl)-1-isopropyl-quinazoline-2,4-dione

The title compound was obtained as a white solid, MS: m/e=360.1/362.1 (M+H$^+$), using chemistry similar to that described in Example 10, step 1 from 5-bromopyridin-2-amine and methyl 2-(isopropylamino)benzoate (Example 42, step 2).

Step 2: 1-Isopropyl-3-[5-(2-phenylethynyl)-2-pyridyl]quinazoline-2,4-dione

The title compound was obtained as a yellow solid, MS: m/e=382.3 (M+H$^+$), using chemistry similar to that described in Example 1, step 3 from 3-(5-bromo-2-pyridyl)-1-isopropyl-quinazoline-2,4-dione (Example 55, step 1) and phenylacetylene.

Example 56

6-[3-Fluoro-5-(2-phenylethynyl)-2-pyridyl]-4-isopropyl-2-methyl-pyrazolo[4,3-d]pyrimidine-5,7-dione

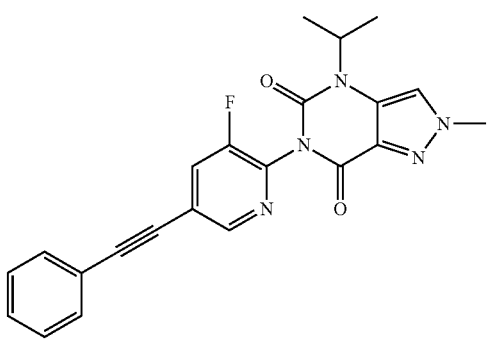 [SMILES: CC(C)n1c(=O)n(-c2ncc(C#Cc3ccccc3)cc2F)c(=O)c2nn(C)cc21]

Step 1: Methyl 4-(isopropylamino)-1-methyl-pyrazole-3-carboxylate

The title compound was obtained as a light blue oil, MS: m/e=198.2 (M+H$^+$), using chemistry similar to that described in Example 42, step 2 from methyl 4-amino-1-methyl-1H-pyrazole-3-carboxylate.

Step 2: 6-[3-Fluoro-5-(2-phenylethynyl)-2-pyridyl]-4-isopropyl-2-methyl-pyrazolo[4,3-d]pyrimidine-5,7-dione The title compound was obtained as a white solid, MS: m/e=404.3 (M+H$^+$), using chemistry similar to that described in Example 10, step 1 from 3-fluoro-5-(2-phenylethynyl)pyridin-2-amine (Example 49, step 1) and methyl 4-(isopropylamino)-1-methyl-pyrazole-3-carboxylate (Example 56, step 1).

Example 57

6-[2,6-Difluoro-4-[2-(3-pyridyl)ethynyl]phenyl]-4-isopropyl-2-methyl-pyrazolo[4,3-d]pyrimidine-5,7-dione

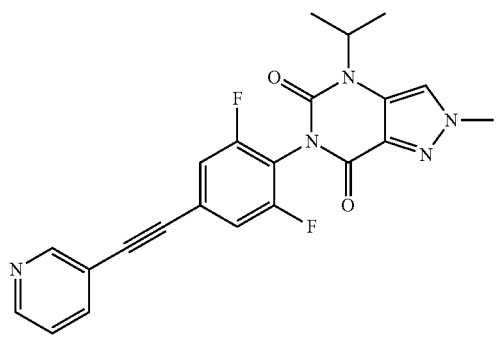

Step 1: 2,6-Difluoro-4-[2-(3-pyridyl)ethynyl]aniline

The title compound was obtained as a yellow solid, MS: m/e=231.2 (M+H$^+$), using chemistry similar to that described in Example 1, step 3 from 2,6-difluoro-4-iodoaniline and 3-ethynylpyridine.

Step 2: 6-[2,6-Difluoro-4-[2-(3-pyridyl)ethynyl]phenyl]-4-isopropyl-2-methyl-pyrazolo[4,3-d]pyrimidine-5,7-dione The title compound was obtained as a white solid, MS: m/e=422.3 (M+H$^+$), using chemistry similar to that described in Example 10, step 1 from 2,6-difluoro-4-[2-(3-pyridyl)ethynyl]aniline (Example 57, step 1) and methyl 4-(isopropylamino)-1-methyl-pyrazole-3-carboxylate (Example 56, step 1).

Example 58

6-[2-Chloro-6-fluoro-4-[2-(3-pyridyl)ethynyl]phenyl]-4-isopropyl-2-methyl-pyrazolo[4,3-d]pyrimidine-5,7-dione

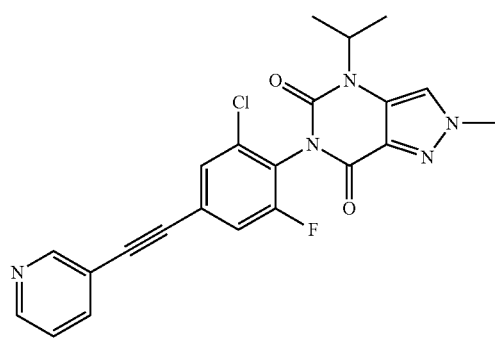

The title compound was obtained as a white solid, MS: m/e=438.3/440.3 (M+H$^+$), using chemistry similar to that described in Example 10, step 1 from 2-chloro-6-fluoro-4-[2-(3-pyridyl)ethynyl]aniline (Example 42, step 1) and 4-(isopropyl amino)-1-methyl-pyrazole-3-carboxylate (Example 56, step 1).

Example 59

6-[3-Chloro-5-[2-(3-pyridyl)ethynyl]-2-pyridyl]-4-isopropyl-2-methyl-pyrazolo[4,3-d]pyrimidine-5,7-dione

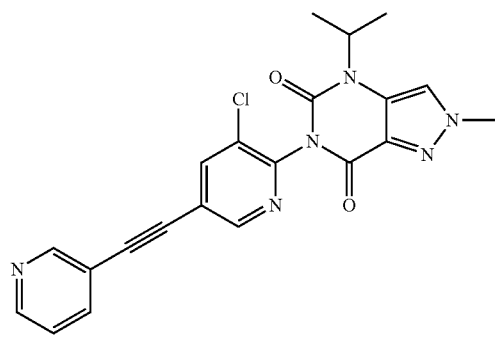 [SMILES: CC(C)n1c(=O)n(-c2ncc(C#Cc3cccnc3)cc2Cl)c(=O)c2nn(C)cc21]

Step 1: 6-(5-bromo-3-chloro-2-pyridyl)-4-isopropyl-2-methyl-pyrazolo[4,3-d]pyrimidine-5,7-dione The title compound was obtained as a white solid, MS: m/e=398.1/400.1 (M+H⁺), using chemistry similar to that described in Example 10, step 1 from 5-bromo-3-chloro-pyridin-2-amine and 4-(isopropylamino)-1-methyl-pyrazole-3-carboxylate (Example 56, step 1).

Step 2: 6-[3-Chloro-5-[2-(3-pyridyl)ethynyl]-2-pyridyl]-4-isopropyl-2-methyl-pyrazolo[4,3-d]pyrimidine-5,7-dione The title compound was obtained as a light brown solid, MS: m/e=421.2/423.2 (M+H⁺), using chemistry similar to that described in Example 1, step 3 from 6-(5-bromo-3-chloro-2-pyridyl)-4-isopropyl-2-methyl-pyrazolo[4,3-d]pyrimidine-5,7-dione (Example 59, step 1) and 3-ethynylpyridine.

Example 60

6-[3-Chloro-5-(2-phenylethynyl)-2-pyridyl]-4-isopropyl-2-methyl-pyrazolo[4,3-d]pyrimidine-5,7-dione

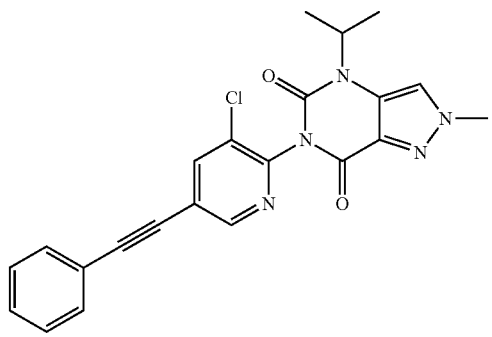 [SMILES: CC(C)n1c(=O)n(-c2ncc(C#Cc3ccccc3)cc2Cl)c(=O)c2nn(C)cc21]

The title compound was obtained as a light brown solid, MS: m/e=420.3/422.3 (M+H⁺), using chemistry similar to that described in Example 1, step 3 from 6-(5-bromo-3-chloro-2-pyridyl)-4-isopropyl-2-methyl-pyrazolo[4, 3-d]pyrimidine-5,7-dione (Example 59, step 1) and phenylacetylene.

Example 61

8-Chloro-3-[2,6-difluoro-4-(2-phenylethynyl)phenyl]-1-methyl-pyrido[3,2-d]pyrimidine-2,4-dione

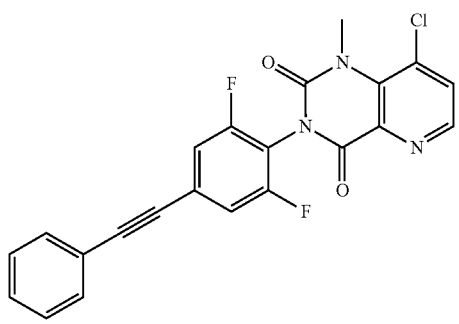

Step 1: 8-Chloro-3-[2,6-difluoro-4-(2-phenylethynyl)phenyl]-1H-pyrido[3,2-d]pyrimidine-2,4-dione The title compound was obtained as a white solid, MS: m/e=410.3/412.3 (M+H⁺), using chemistry similar to that described in Example 10, step 1 from 2,6-difluoro-4-phenylethynyl-phenylamine (Example 25, step 1) and 3-amino-4-chloropicolinic acid.

Step 2: 8-Chloro-3-[2,6-difluoro-4-(2-phenylethynyl)phenyl]-1-methyl-pyrido[3,2-d]pyrimidine-2,4-dione The title compound was obtained as a white solid, MS: m/e=424.2/426.2 (M+H⁺), using chemistry similar to that described in Example 1, step 4 from 8-chloro-3-[2,6-difluoro-4-(2-phenylethynyl)phenyl]-1H-pyrido[3,2-d]pyrimidine-2,4-dione (Example 61, step 1) and iodomethane.

Example 62

5-[2,6-Difluoro-4-(2-phenylethynyl)phenyl]-2,7-dimethyl-pyrazolo[3,4-d]pyrimidine-4,6-dione

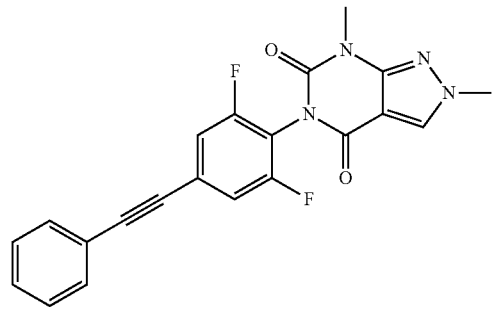

Step 1: Methyl 3-[[2,6-difluoro-4-(2-phenylethynyl)phenyl]carbamoylamino]-1-methyl-pyrazole-4-carboxylate The title compound was obtained as a light yellow solid, MS: m/e=411.3 (M−H⁺), using chemistry similar to that described in Example 10, step 1 from 2,6-difluoro-4-phenylethynyl-phenylamine (Example 25, step 1) and methyl 3-amino-1-methyl-1H-pyrazole-4-carboxylate.

Step 2: 5-[2,6-Difluoro-4-(2-phenylethynyl)phenyl]-2-methyl-7H-pyrazolo[3,4-d]pyrimidine-4,6-dione The title compound was obtained as a white solid, MS: m/e=379.3 (M+H⁺), using chemistry similar to that described in Example 11, step 2 from methyl 3-[[2,6-difluoro-4-(2-phenylethynyl)phenyl]carbamoylamino]-1-methyl-pyrazole-4-carboxylate (Example 62, step 1).

Step 3: 5-[2,6-Difluoro-4-(2-phenylethynyl)phenyl]-2,7-dimethyl-pyrazolo[3,4-d]pyrimidine-4,6-dione The title compound was obtained as a white solid, MS: m/e=393.2 (M+H⁺), using chemistry similar to that described in Example 1, step 4 from 5-[2,6-difluoro-4-(2-phenylethynyl)phenyl]-2-methyl-7H-pyrazolo[3,4-d]pyrimidine-4,6-dione (Example 62, step 2) and iodomethane.

Example 63

5-[2,6-Difluoro-4-(2-phenylethynyl)phenyl]-1,7-dimethyl-pyrazolo[3,4-d]pyrimidine-4,6-dione

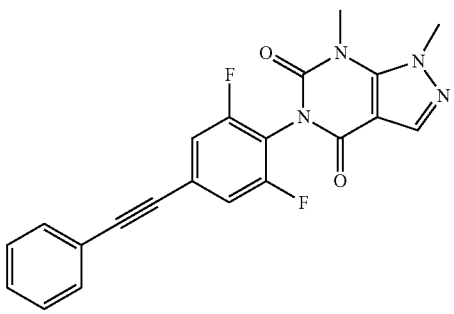 [SMILES: Cn1ncc2c(=O)n(-c3c(F)cc(C#Cc4ccccc4)cc3F)c(=O)n(C)c21]

Step 1: Methyl 5-[[2,6-difluoro-4-(2-phenylethynyl)phenyl]carbamoylamino]-1-methyl-pyrazole-4-carboxylate The title compound was obtained as a light yellow solid, MS: m/e=411.3 (M–H$^+$), using chemistry similar to that described in Example 10, step 1 from 2,6-difluoro-4-phenylethynyl-phenylamine (Example 25, step 1) and methyl 5-amino-1-methyl-1H-pyrazole-4-carboxylate.

Step 2: 5-[2,6-Difluoro-4-(2-phenylethynyl)phenyl]-1-methyl-7H-pyrazolo[3,4-d]pyrimidine-4,6-dione The title compound was obtained as a white solid, MS: m/e=379.3 (M+H$^+$), using chemistry similar to that described in Example 11, step 2 from methyl 5-[[2,6-difluoro-4-(2-phenylethynyl)phenyl]carbamoylamino]-1-methyl-pyrazole-4-carboxylate (Example 63, step 1).

Step 3: 5-[2,6-Difluoro-4-(2-phenylethynyl)phenyl]-1,7-dimethyl-pyrazolo[3,4-d]pyrimidine-4,6-dione The title compound was obtained as a white solid, MS: m/e=393.2 (M+H$^+$), using chemistry similar to that described in Example 1, step 4 from 5-[2,6-difluoro-4-(2-phenylethynyl)phenyl]-1-methyl-7H-pyrazolo[3,4-d]pyrimidine-4,6-dione (Example 63, step 2) and iodomethane.

Example 64

5-[2,6-Difluoro-4-(2-phenylethynyl)phenyl]-7-isopropyl-2H-pyrazolo[3,4-d]pyrimidine-4,6-dione

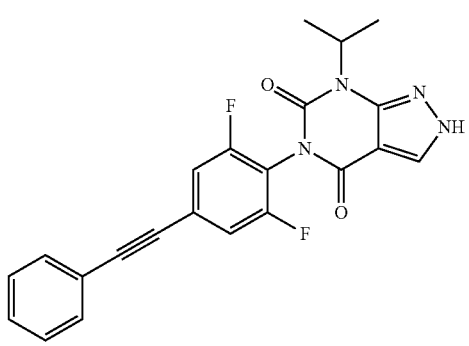 [SMILES: CC(C)n1c(=O)n(-c2c(F)cc(C#Cc3ccccc3)cc2F)c(=O)c2c[nH]nc21]

Step 1: Methyl 3-(isopropylamino)-1H-pyrazole-4-carboxylate

The title compound was obtained as a light blue oil, MS: m/e=184.2 (M+H$^+$), using chemistry similar to that described in Example 42, step 2 from methyl 3-amino-1H-pyrazole-4-carboxylate.

Step 2: 5-[2,6-Difluoro-4-(2-phenylethynyl)phenyl]-7-isopropyl-2H-pyrazolo[3,4-d]pyrimidine-4,6-dione The title compound was obtained as a white solid, MS: m/e=407.5 (M+H$^+$), using chemistry similar to that described in Example 10, step 1 from 2,6-difluoro-4-phenylethynyl-phenylamine (Example 25, step 1) and methyl 3-(isopropylamino)-1H-pyrazole-4-carboxylate (Example 64, step 1).

Example 65

3-[2-Chloro-4-(2-phenylethynyl)phenyl]-8-methoxy-1-methyl-quinazoline-2,4-dione

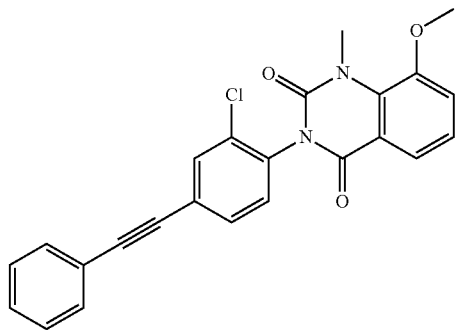 [SMILES: COc1cccc2c(=O)n(-c3ccc(C#Cc4ccccc4)cc3Cl)c(=O)n(C)c12]

Step 1: 3-[2-Chloro-4-(2-phenylethynyl)phenyl]-8-methoxy-1H-quinazoline-2,4-dione The title compound was obtained as a yellow solid, MS: m/e=403.2/405.1 (M+H$^+$), using chemistry similar to that described in Example 10, step 1 from 2-chloro-4-(2-phenylethynyl)aniline (Example 4, step 1) and methyl 2-amino-3-methoxybenzoate.

Step 2: 3-[2-Chloro-4-(2-phenylethynyl)phenyl]-8-methoxy-1-methyl-quinazoline-2,4-dione The title compound was obtained as a light yellow solid, MS: m/e=417.2/419.1 (M+H$^+$), using chemistry similar to that described in Example 1, step 4 from 3-[2-chloro-4-(2-phenylethynyl)phenyl]-8-methoxy-1H-quinazoline-2,4-dione (Example 65, step 1) and iodomethane.

Example 66

3-[2,6-Difluoro-4-(2-phenylethynyl)phenyl]-1-(oxetan-3-yl)quinazoline-2,4-dione

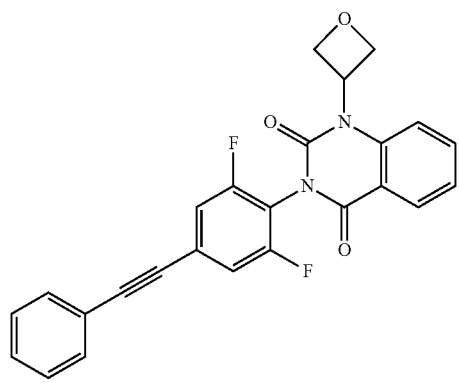 [SMILES: O=c1c2ccccc2n(C2COC2)c(=O)n1-c1c(F)cc(C#Cc2ccccc2)cc1F]

Step 1: Methyl 2-(oxetan-3-ylamino)benzoate

The title compound was obtained as a colorless oil, MS: m/e=208.2 (M+H$^+$), using chemistry similar to that described in Example 42, step 2 from methyl 2-aminobenzoate and oxetan-3-one.

Step 2: 3-[2,6-Difluoro-4-(2-phenylethynyl)phenyl]-1-(oxetan-3-yl)quinazoline-2,4-dione The title compound was obtained as a white solid, MS: m/e=431.3 (M+H$^+$), using chemistry similar to that described in Example 10, step 1 from 2,6-difluoro-4-phenylethynyl-phenylamine (Example 25, step 1) and methyl 2-(oxetan-3-ylamino)benzoate (Example 65, step 1).

Example 67

6-[2-Chloro-4-(2-phenylethynyl)phenyl]-4-methyl-thiazolo[5,4-d]pyrimidine-5,7-dione

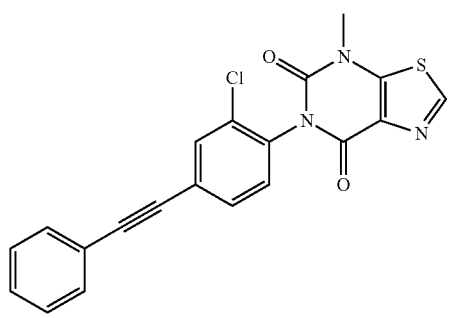 [SMILES: Cn1c(=O)n(-c2ccc(C#Cc3ccccc3)cc2Cl)c(=O)c2ncsc21]

The title compound was obtained as a light yellow solid, MS: m/e=394.1/396.1 (M+H$^+$), using chemistry similar to that described in Example 10, step 1 from 2-chloro-4-(2-phenylethynyl)aniline (Example 4, step 1) and ethyl 5-(methylamino)thiazole-4-carboxylate.

Example 68

3-[2,6-Difluoro-4-(2-phenylethynyl)phenyl]-1-isopropyl-pteridine-2,4-dione

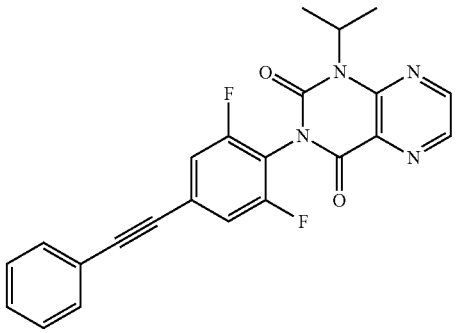 [SMILES: CC(C)n1c(=O)n(-c2c(F)cc(C#Cc3ccccc3)cc2F)c(=O)c2nccnc21]

Step 1: 3-[2,6-Difluoro-4-(2-phenylethynyl)phenyl]-1H-pteridine-2,4-dione

The title compound was obtained as a white solid, MS: m/e=377.1 (M+H$^+$), using chemistry similar to that described in Example 10, step 1 from 2,6-difluoro-4-phenylethynyl-phenylamine (Example 25, step 1) and methyl 3-aminopyrazine-2-carboxylate.

Step 2: 3-[2,6-Difluoro-4-(2-phenylethynyl)phenyl]-1-isopropyl-pteridine-2,4-dione The title compound was obtained as a white solid, MS: m/e=419.3 (M+H$^+$), using chemistry similar to that described in Example 1, step 4 from 3-[2,6-difluoro-4-(2-phenylethynyl)phenyl]-1H-pteridine-2,4-dione (Example 68, step 1) and 2-iodopropane.

Example 69

1-[2,6-Difluoro-4-(2-phenylethynyl)phenyl]-3,7-dimethyl-purine-2,6-dione

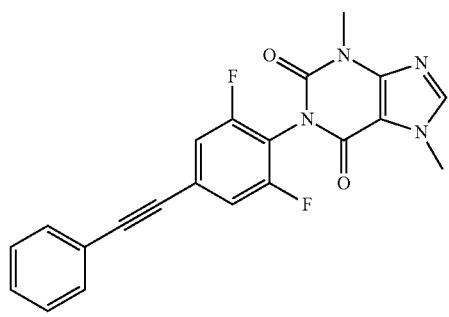 [SMILES: Cn1cnc2c1c(=O)n(-c1c(F)cc(C#Cc3ccccc3)cc1F)c(=O)n2C]

Step 1: Ethyl 5-[(2,6-difluoro-4-iodo-phenyl)carbamoylamino]-3-methyl-imidazole-4-carboxylate The title compound was obtained as a white solid, MS: m/e=425.3 (M–H$^+$), using chemistry similar to that described in Example 10, step 1 from 2,6-difluoro-4-phenylethynyl-phenylamine (Example 25, step 1) and ethyl 4-amino-1-methyl-1H-imidazole-5-carboxylate.

Step 2: 1-[2,6-Difluoro-4-(2-phenylethynyl)phenyl]-7-methyl-3H-purine-2,6-dione

The title compound was obtained as a light yellow solid, MS: m/e=379.2 (M+H$^+$), using chemistry similar to that described in Example 11, step 2 from ethyl 5-[(2,6-difluoro-4-iodo-phenyl)carbamoylamino]-3-methyl-imidazole-4-carboxylate (Example 69, step 1) and by using sodium hydride instead of KOtBu.

Step 3: 1-[2,6-Difluoro-4-(2-phenylethynyl)phenyl]-3,7-dimethyl-purine-2,6-dione The title compound was obtained as a yellow solid, MS: m/e=393.2 (M+H$^+$), using chemistry similar to that described in Example 1, step 4 from 1-[2,6-difluoro-4-(2-phenylethynyl)phenyl]-7-methyl-3H-purine-2,6-dione (Example 69, step 2) and iodomethane.

Example 70

3-[2,6-Difluoro-4-(2-phenylethynyl)phenyl]-8-methoxy-1-methyl-quinazoline-2,4-dione

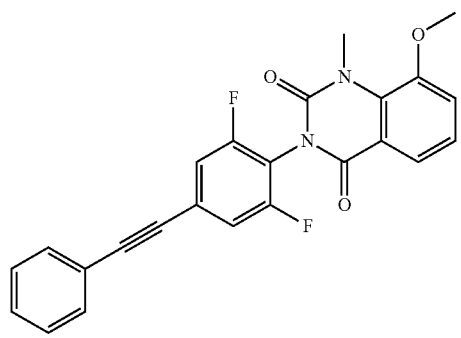 [SMILES: COc1cccc2c(=O)n(-c3c(F)cc(C#Cc4ccccc4)cc3F)c(=O)n(C)c12]

Step 1: 3-[2,6-Difluoro-4-(2-phenylethynyl)phenyl]-8-methoxy-1H-quinazoline-2,4-dione The title compound was obtained as a white solid, MS: m/e=403.2 (M−H), using chemistry similar to that described in Example 10, step 1 from 2,6-difluoro-4-phenylethynyl-phenylamine (Example 25, step 1) and methyl 2-amino-3-methoxybenzoate.

Step 2: 3-[2,6-Difluoro-4-(2-phenylethynyl)phenyl]-8-methoxy-1-methyl-quinazoline-2,4-dione The title compound was obtained as a white solid, MS: m/e=419.2 (M+H$^+$), using chemistry similar to that described in Example 1, step 4 from 3-[2,6-difluoro-4-(2-phenylethynyl)phenyl]-8-methoxy-1H-quinazoline-2,4-dione (Example 70, step 1) and iodomethane.

Example 71

3-[2-Chloro-6-fluoro-4-[2-(3-pyridyl)ethynyl]phenyl]-1-(oxetan-3-yl)quinazoline-2,4-dione

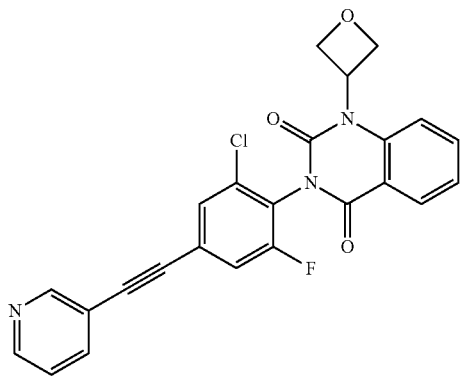 [SMILES: O=c1c2ccccc2n(C2COC2)c(=O)n1-c1c(F)cc(C#Cc2cccnc2)cc1Cl]

The title compound was obtained as a white solid, MS: m/e=448.2/450.2 (M+H$^+$), using chemistry similar to that described in Example 10, step 1 from 2-chloro-6-fluoro-4-[2-(3-pyridyl)ethynyl]aniline (Example 42, step 1) and methyl 2-(oxetan-3-ylamino)benzoate (Example 65, step 1).

Example 72

3-[2-Fluoro-4-(2-phenylethynyl)-6-(trifluoromethyl)phenyl]-1-isopropyl-quinazoline-2,4-dione

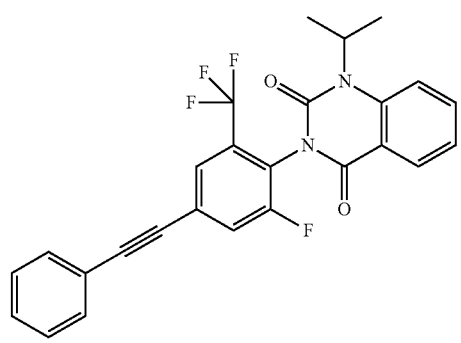 [SMILES: CC(C)n1c(=O)n(-c2c(F)cc(C#Cc3ccccc3)cc2C(F)(F)F)c(=O)c2ccccc21]

Step 1: 3-[4-Bromo-2-fluoro-6-(trifluoromethyl)phenyl]-1-isopropyl-quinazoline-2,4-dione The title compound was obtained as a colorless oil, MS: m/e=445.2/447.2 (M+H$^+$), using chemistry similar to that described in Example 10, step 1 from 4-bromo-2-fluoro-6-(trifluoromethyl)aniline and methyl 2-(isopropylamino)benzoate (Example 42, step 2).

Step 2: 3-[2-Fluoro-4-(2-phenylethynyl)-6-(trifluoromethyl)phenyl]-1-isopropyl-quinazoline-2,4-dione The title compound was obtained as a colorless oil, MS: m/e=468.3 (M+H$^+$), using chemistry similar to that described in Example 1, step 3 from 3-[4-bromo-2-fluoro-6-(trifluoromethyl)phenyl]-1-isopropyl-quinazoline-2,4-dione (Example 72, step 1) and phenylacetylene.

Example 73

3-[2,6-Difluoro-4-[2-(3-pyridyl)ethynyl]phenyl]-1,8-dimethyl-quinazoline-2,4-dione

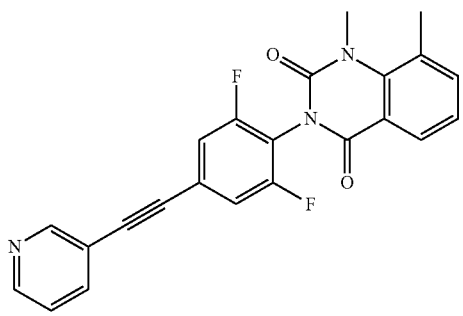

The title compound was obtained as a white solid, MS: m/e=404.2 (M+H$^+$), using chemistry similar to that described in Example 10, step 1 from 2,6-difluoro-4-pyridin-3-ylethynyl-phenylamine (Example 28, step 1) and methyl 3-methyl-2-(methylamino)benzoate.

Example 74

8-(2,2-Difluoroethoxy)-3-[2,6-difluoro-4-(2-phenylethynyl)phenyl]-1-methyl-quinazoline-2,4-dione

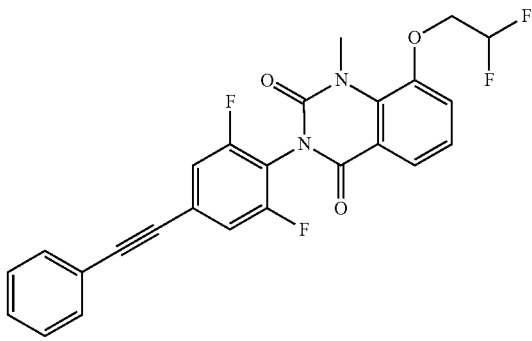 [SMILES: Cn1c(=O)n(-c2c(F)cc(C#Cc3ccccc3)cc2F)c(=O)c2cccc(OCC(F)F)c21]

Step 1: 8-(2,2-Difluoroethoxy)-3-[2,6-difluoro-4-(2-phenylethynyl)phenyl]-1H-quinazoline-2,4-dione The title compound was obtained as a yellow solid, MS: m/e=455.1 (M+H$^+$), using chemistry similar to that described in Example 10, step 1 from 2,6-difluoro-4-phenylethynyl-phenylamine (Example 25, step 1) and methyl 2-amino-3-(2,2-difluoroethoxy)benzoate.

Step 2: 8-(2,2-Difluoroethoxy)-3-[2,6-difluoro-4-(2-phenylethynyl)phenyl]-1-methyl-quinazoline-2,4-dione The title compound was obtained as a white solid, MS: m/e=469.2 (M+H$^+$), using chemistry similar to that described in Example 1, step 4 from 8-(2,2-difluoroethoxy)-3-[2,6-difluoro-4-(2-phenylethynyl)phenyl]-1H-quinazoline-2,4-dione (Example 74, step 1) and iodomethane.

The invention claimed is:

1. A compound of formula I

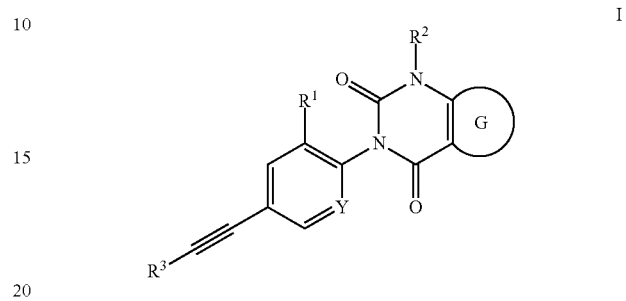

wherein

Y is N or C—R$^{1'}$;

G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

R$^1$ is hydrogen, halogen or lower alkyl substituted by halogen;

R$^{1'}$ is hydrogen, halogen or lower alkyl substituted by halogen;

R$^2$ is hydrogen, lower alkyl, lower alkoxyalkyl, cycloalkyl or heterocycloalkyl;

or R$^2$ may form together with the closest carbon atom in group G a group

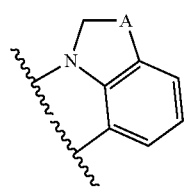

for A being —CH$_2$—, —CH$_2$CH$_2$, or —C(CH$_3$)$_2$—,

R$^3$ is phenyl or pyridinyl, wherein the N atom in the pyridinyl group may be in different positions;

or a pharmaceutically acceptable salt or acid addition salt, a racemic mixture, or its corresponding enantiomer, optical isomer, or stereoisomer thereof.

2. The compound of formula IA according to claim 1,

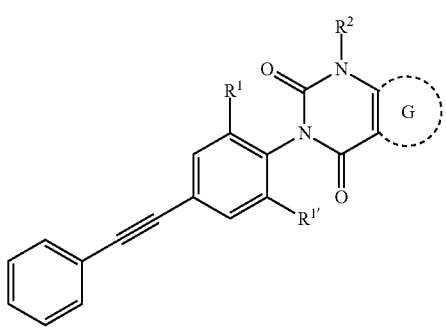

wherein
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';
R and R' are independently from each other hydrogen or lower alkyl, or may form together with the N atom to which they are attached a five or six membered saturated heterocyclic group which may contain an additional oxygen, NH, or N-lower alkyl group;
$R^1$ is hydrogen, halogen or lower alkyl substituted by halogen;
$R^{1'}$ is hydrogen, halogen or lower alkyl substituted by halogen;
$R^2$ is hydrogen, lower alkyl, lower alkoxyalkyl, cycloalkyl or heterocycloalkyl;
or $R^2$ may form together with the closest carbon atom in group G a group

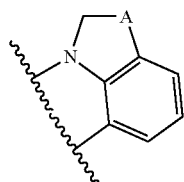

for A being —$CH_2$—, —$CH_2CH_2$—, or —$C(CH_3)_2$—,
or a pharmaceutically acceptable salt or acid addition salt, a racemic mixture, or its corresponding enantiomer, optical isomer, or stereoisomer thereof.

3. The compound of formula IA according to claim 2, wherein the compound is selected from the group consisting of
3-[2-Chloro-4-(2-phenylethynyl)phenyl]-1-methyl-quinazoline-2,4-dione
3-[2-Chloro-4-(2-phenylethynyl)phenyl]-1,8-dimethyl-quinazoline-2,4-dione
8-Chloro-3-[2-chloro-4-(2-phenylethynyl)phenyl]-1-methyl-quinazoline-2,4-dione
7-Chloro-3-[2-chloro-4-(2-phenylethynyl)phenyl]-1-methyl-quinazoline-2,4-dione
3-[2-Chloro-4-(2-phenylethynyl)phenyl]-1,7-dimethyl-quinazoline-2,4-dione
3-[2-Chloro-4-(2-phenylethynyl)phenyl]-1H-pyrido[2,3-d]pyrimidine-2,4-dione
3-[2-Chloro-4-(2-phenylethynyl)phenyl]-1-methyl-pyrido[2,3-d]pyrimidine-2,4-dione
3-[2-Chloro-4-(2-phenylethynyl)phenyl]-8-ethyl-1-methyl-quinazoline-2,4-dione
3-[2-Chloro-4-(2-phenylethynyl)phenyl]-1-methyl-pyrido[3,2-d]pyrimidine-2,4-dione
3-[2-Chloro-4-(2-phenylethynyl)phenyl]-1-methyl-pyrido[4,3-d]pyrimidine-2,4-dione
1-[2-Chloro-4-(2-phenylethynyl)phenyl]-3,7-dimethyl-purine-2,6-dione
2-(2-Chloro-4-(phenylethynyl)phenyl)-5,6-dihydro-1H-pyrrolo[3,2,1-ij]quinazoline-1,3(2H)-dione
3-[2-Chloro-4-(2-phenylethynyl)phenyl]-1-isopropyl-quinazoline-2,4-dione
3-[2-Chloro-4-(2-phenylethynyl)phenyl]-1-ethyl-quinazoline-2,4-dione
3-[2-Chloro-4-(2-phenylethynyl)phenyl]-1-methyl-pteridine-2,4-dione
3-[2-Chloro-4-(2-phenylethynyl)phenyl]-1H-pyrimido[4,5-d]pyrimidine-2,4-dione
3-[2-Chloro-4-(2-phenylethynyl)phenyl]-1-methyl-pyrimido[4,5-d]pyrimidine-2,4-dione
3-[2-Chloro-4-(2-phenylethynyl)phenyl]-6-fluoro-1-methyl-quinazoline-2,4-dione
3-[2-Chloro-4-(2-phenylethynyl)phenyl]-7, 8-difluoro-1-methyl-quinazoline-2,4-dione
3-[2-Chloro-4-(2-phenylethynyl)phenyl]-1,7-dimethyl-thieno[3,2-d]pyrimidine-2,4-dione
3-[2-Chloro-4-(2-phenylethynyl)phenyl]-1-isopropyl-pteridine-2,4-dione
3-[2,6-Difluoro-4-(2-phenylethynyl)phenyl]-1-methyl-quinazoline-2,4-dione
3-[2,6-Difluoro-4-(2-phenylethynyl)phenyl]-1,8-dimethyl-quinazoline-2,4-dione
3-(2, 6-Difluoro-4-phenylethynyl-phenyl)-1-methyl-1H-pyrido[2,3-d]pyrimidine-2,4-dione
3-[2,6-Difluoro-4-(2-phenylethynyl)phenyl]-1,7-dimethyl-quinazoline-2,4-dione
3-[2,6-Difluoro-4-(2-phenylethynyl)phenyl]-1,7-dimethyl-thieno[3,2-d]pyrimidine-2,4-dione
2-(2,6-Difluoro-4-(phenylethynyl)phenyl)-5,6-dihydro-1H-pyrrolo[3,2,1-ij]quinazoline-1,3(2H)-dione
6-[2,6-Difluoro-4-(2-phenylethynyl)phenyl]-4H-thiazolo[4,5-d]pyrimidine-5,7-dione
6-[2,6-Difluoro-4-(2-phenylethynyl)phenyl]-4-methyl-thiazolo[4, 5-d]pyrimidine-5,7-dione
6-[2,6-Difluoro-4-(2-phenylethynyl)phenyl]-2,4-dimethyl-pyrazolo[4,3-d]pyrimidine-5,7-dione
6-[2,6-Difluoro-4-(2-phenylethynyl)phenyl]-1,4-dimethyl-pyrazolo[4,3-d]pyrimidine-5,7-dione
6-[2,6-Difluoro-4-(2-phenylethynyl)phenyl]-4-isopropyl-2-methyl-pyrazolo[4,3-d]pyrimidine-5,7-dione
6-[2,6-Difluoro-4-(2-phenylethynyl)phenyl]-4-isopropyl-1-methyl-pyrazolo[4,3-d]pyrimidine-5,7-dione
3-[2,6-Difluoro-4-(2-phenylethynyl)phenyl]-1-isopropyl-pyrido[2,3-d]pyrimidine-2,4-dione
3-[2,6-Difluoro-4-(2-phenylethynyl)phenyl]-1,8-dimethyl-pyrido[3,2-d]pyrimidine-2,4-dione
6-[2,6-Difluoro-4-(2-phenylethynyl)phenyl]-4-methyl-[1,2,5]thiadiazolo[3,4-d]pyrimidine-5,7-dione
6-[2,6-Difluoro-4-(2-phenylethynyl)phenyl]-4-isopropyl-[1,2,5]thiadiazolo[3,4-d]pyrimidine-5,7-dione 3-[2-Chloro-4-(2-phenylethynyl)phenyl]-1,5-dimethyl-quinazoline-2,4-dione
3-[2-Chloro-4-(2-phenylethynyl)phenyl]-1-(2-methoxy-ethyl)quinazoline-2,4-dione
6-[2-Chloro-4-(2-phenylethynyl)phenyl]-4-methyl-2-morpholino-thiazolo[4,5-d]pyrimidine-5,7-dione
6-(2-Chloro-4-phenylethynyl-phenyl)-4-methyl-4H-thiazolo[4,5-d]pyrimidine-5,7-dione
3-[2-Chloro-4-(2-phenylethynyl)phenyl]-1-cyclobutyl-quinazoline-2,4-dione
3-[2-Chloro-4-(2-phenylethynyl)phenyl]-8-isopropyl-1-methyl-quinazoline-2,4-dione
8-Chloro-3-[2,6-difluoro-4-(2-phenylethynyl)phenyl]-1-methyl-pyrido[3,2-d]pyrimidine-2,4-dione
5-[2,6-Difluoro-4-(2-phenylethynyl)phenyl]-2,7-dimethyl-pyrazolo[3,4-d]pyrimidine-4,6-dione
5-[2,6-Difluoro-4-(2-phenylethynyl)phenyl]-1,7-dimethyl-pyrazolo[3,4-d]pyrimidine-4,6-dione
5-[2,6-Difluoro-4-(2-phenylethynyl)phenyl]-7-isopropyl-2H-pyrazolo[3,4-d]pyrimidine-4,6-dione
3-[2-Chloro-4-(2-phenylethynyl)phenyl]-8-methoxy-1-methyl-quinazoline-2,4-dione
3-[2,6-Difluoro-4-(2-phenylethynyl)phenyl]-1-(oxetan-3-yl)quinazoline-2,4-dione
6-[2-Chloro-4-(2-phenylethynyl)phenyl]-4-methyl-thiazolo[5,4-d]pyrimidine-5,7-dione
3-[2,6-Difluoro-4-(2-phenylethynyl)phenyl]-1-isopropyl-pteridine-2,4-dione
1-[2,6-Difluoro-4-(2-phenylethynyl)phenyl]-3,7-dimethyl-purine-2,6-dione
3-[2,6-Difluoro-4-(2-phenylethynyl)phenyl]-8-methoxy-1-methyl-quinazoline-2,4-dione
3-[2-Fluoro-4-(2-phenylethynyl)-6-(trifluoromethyl)phenyl]-1-isopropyl-quinazoline-2,4-dione and
8-(2,2-Difluoroethoxy)-3-[2,6-difluoro-4-(2-phenylethynyl)phenyl]-1-methyl-quinazoline-2,4-dione.

4. The compound of formula IB according to claim 1

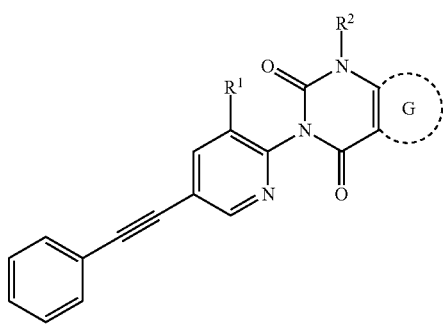

IB wherein
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';
R and R' are independently from each other hydrogen or lower alkyl, or may form together with the N atom to which they are attached a five or six membered saturated heterocyclic group which may contain an additional oxygen, NH, or N-lower alkyl group;
$R^1$ is hydrogen, halogen or lower alkyl substituted by halogen;
$R^2$ is hydrogen, lower alkyl, lower alkoxyalkyl, cycloalkyl or heterocycloalkyl;
or $R^2$ may form together with the closest carbon atom in group G a group

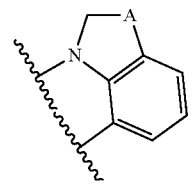

for A being —$CH_2$—, —$CH_2CH_2$, or —$C(CH_3)_2$—,
or a pharmaceutically acceptable salt or acid addition salt, a racemic mixture, or its corresponding enantiomer, optical isomer, or stereoisomer thereof.

5. The compound of formula IB according to claim 4, which compound is selected from the group consisting of
3-[3-Chloro-5-(2-phenylethynyl)-2-pyridyl]-1-methyl-quinazoline-2,4-dione
3-[3-Chloro-5-(2-phenylethynyl)-2-pyridyl]-1-isopropyl-quinazoline-2,4-dione
3-[3-Chloro-5-(2-phenylethynyl)-2-pyridyl]-1,8-dimethyl-quinazoline-2,4-dione
2-(3-Chloro-5-(phenylethynyl)pyridin-2-yl)-5, 6-dihydro-1H-pyrrolo[3,2,1-ij]quinazoline-1,3(2H)-dione
1-Methyl-3-[5-(2-phenylethynyl)-3-(trifluoromethyl)-2-pyridyl]quinazoline-2,4-dione
3-[3-Fluoro-5-(2-phenylethynyl)-2-pyridyl]-1,8-dimethyl-quinazoline-2,4-dione
1-Isopropyl-3-[5-(2-phenylethynyl)-2-pyridyl]quinazoline-2,4-dione
6-[3-Fluoro-5-(2-phenylethynyl)-2-pyridyl]-4-isopropyl-2-methyl-pyrazolo[4,3-d]pyrimidine-5,7-dione and
6-[3-Chloro-5-(2-phenylethynyl)-2-pyridyl]-4-isopropyl-2-methyl-pyrazolo[4,3-d]pyrimidine-5,7-dione.

6. The compound of formula IC according to claim 1,

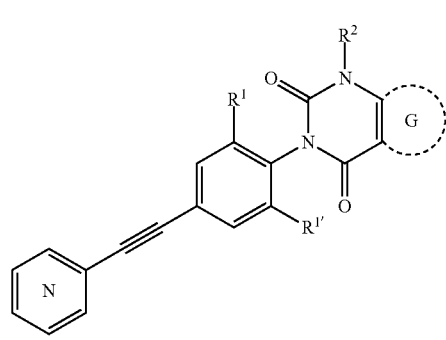

IC wherein
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

$R^1$ is hydrogen, halogen or lower alkyl substituted by halogen;

$R^{1'}$ is hydrogen, halogen or lower alkyl substituted by halogen;

$R^2$ is hydrogen, lower alkyl, lower alkoxyalkyl, cycloalkyl or heterocycloalkyl;

or $R^2$ may form together with the closest carbon atom in group G a group

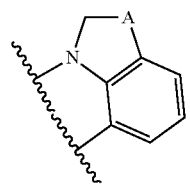

for A being —CH$_2$—, —CH$_2$CH$_2$—, or —C(CH$_3$)$_2$—,
or a pharmaceutically acceptable salt or acid addition salt, a racemic mixture, or its corresponding enantiomer, optical isomer, or stereoisomer thereof.

7. The compound of formula IC according to claim 6, wherein the compound is selected from the group consisting of 3-[2-Chloro-4-[2-(3-pyridyl)ethynyl]phenyl]-1-isopropyl-pteridine-2,4-dione 3-[2,6-Difluoro-4-[2-(3-pyridyl)ethynyl]phenyl]-1,7-dimethyl-thieno[3,2-d]pyrimidine-2,4-dione 2-(2,6-Difluoro-4-(pyridin-3-ylethynyl)phenyl)-5,6-dihydro-1H-pyrrolo[3,2,1-ij]quinazoline-1,3(2H)-dione 3-[2-Chloro-6-fluoro-4-[2-(3-pyridyl)ethynyl]phenyl]-1-isopropyl-quinazoline-2,4-dione 3-[2-Chloro-6-fluoro-4-[2-(3-pyridyl)ethynyl]phenyl]-1,8-dimethyl-quinazoline-2,4-dione 6-[2,6-Difluoro-4-[2-(3-pyridyl)ethynyl]phenyl]-4-isopropyl-2-methy-pyrazol o[4,3-d]pyrimidine-5,7-dione 6-[2-Chloro-6-fluoro-4-[2-(3-pyridyl)ethynyl]phenyl]-4-isopropyl-2-methyl-pyrazolo[4,3-d]pyrimidine-5,7-dione 3-[2-Chloro-6-fluoro-4-[2-(3-pyridyl)ethynyl]phenyl]-1-(oxetan-3-yl)quinazoline-2,4-dione and 3-[2,6-Difluoro-4-[2-(3-pyridyl)ethynyl]phenyl]-1,8-dimethyl-quinazoline-2,4-dione.

8. The compound of formula ID according to claim 1,

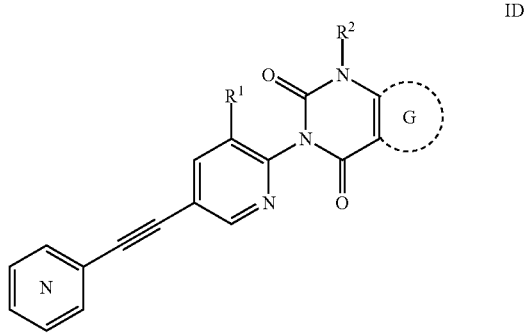

wherein
G is a 5 or 6-membered aromatic or heteroaromatic ring containing 0, 1, 2 or 3 heteroatoms, selected from the group consisting of phenyl, pyridinyl with different N-positions, imidazolyl, pyrazinyl, pyrimidinyl, thiophenyl, thiazolyl, pyrazolyl or thiadiazolyl, which are optionally substituted by 1, 2 or 3 substituents, selected from the group consisting of halogen, lower alkyl, lower alkoxy, lower alkoxy substituted by halogen or NRR';

R and R' are independently from each other hydrogen or lower alkyl, or may form together with the N atom to which they are attached a five or six membered saturated heterocyclic group which may contain an additional oxygen, NH, or N-lower alkyl group;

$R^1$ is hydrogen, halogen or lower alkyl substituted by halogen;

$R^2$ is hydrogen, lower alkyl, lower alkoxyalkyl, cycloalkyl or heterocycloalkyl;

or $R^2$ may form together with the closest carbon atom in group G a group

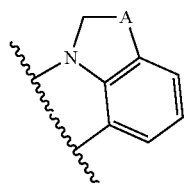

for A being —CH$_2$—, —CH$_2$CH$_2$—, or —C(CH$_3$)$_2$—,
or a pharmaceutically acceptable salt or acid addition salt, a racemic mixture, or its corresponding enantiomer, optical isomer, or stereoisomer thereof.

9. The compound of formula ID according to claim 8, wherein the compound is

6-[3-Chloro-5-[2-(3-pyridyl)ethynyl]-2-pyridyl]-4-isopropyl-2-methyl-pyrazolo[4,3-d]pyrimidine-5,7-dione.

10. A process for the manufacture of a compound of formula I as defined in claim 1, which process comprises reacting a compound of formula 3

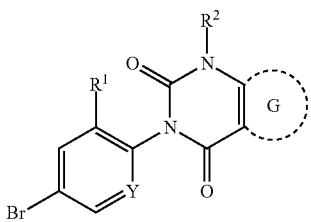

with a compound of formula

to form a compound of formula I

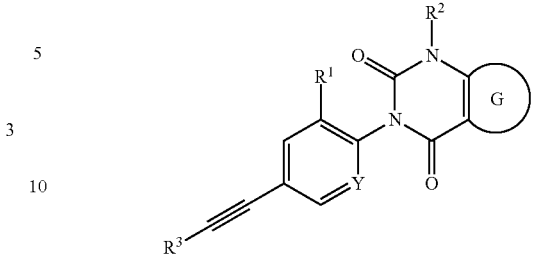

wherein the substituents are described in claim 1, or
if desired, converting the compound obtained into a pharmaceutically acceptable acid addition salt.

11. A pharmaceutical composition comprising a compound of formula I of claim 1, and a pharmaceutically acceptable excipient.

12. A method for the treatment of Parkinson's disease, anxiety, emesis, obsessive compulsive disorder, autism, neuroprotection, cancer, depression and diabetes type 2, which method comprises administering an effective amount of a compound of formula I as in claim 1 to a patient in need thereof.

* * * * *